United States Patent
Aoki

(10) Patent No.: US 11,473,089 B2
(45) Date of Patent: Oct. 18, 2022

(54) APTAMER FOR ADAMTS5 AND USE FOR APTAMER FOR ADAMTS5

(71) Applicant: RIBOMIC INC., Tokyo (JP)

(72) Inventor: Kazuteru Aoki, Tokyo (JP)

(73) Assignee: RIBOMIC INC., Tokyo (JP)

( * ) Notice: Subject to any disclaimer, the term of this patent is extended or adjusted under 35 U.S.C. 154(b) by 0 days.

(21) Appl. No.: 16/761,880

(22) PCT Filed: Nov. 9, 2018

(86) PCT No.: PCT/JP2018/041746
§ 371 (c)(1),
(2) Date: May 6, 2020

(87) PCT Pub. No.: WO2019/093497
PCT Pub. Date: May 16, 2019

(65) Prior Publication Data
US 2021/0246451 A1    Aug. 12, 2021

(30) Foreign Application Priority Data
Nov. 9, 2017  (JP) .............................. JP2017-216280

(51) Int. Cl.
*C12N 15/115* (2010.01)
*G01N 33/573* (2006.01)

(52) U.S. Cl.
CPC ......... *C12N 15/115* (2013.01); *G01N 33/573* (2013.01); *C12N 2310/16* (2013.01); *G01N 2333/96486* (2013.01)

(58) Field of Classification Search
None
See application file for complete search history.

(56) References Cited

U.S. PATENT DOCUMENTS

| | | | |
|---|---|---|---|
| 2009/0170219 A1 | 7/2009 | Nakamura et al. | |
| 2012/0095193 A1 | 4/2012 | Burden et al. | |
| 2012/0165401 A1 | 6/2012 | Nakamura et al. | |
| 2017/0044545 A1 | 2/2017 | Ikeda | |
| 2018/0250323 A1 | 9/2018 | Zhang et al. | |

FOREIGN PATENT DOCUMENTS

| | | |
|---|---|---|
| JP | 2012-531902 A | 12/2012 |
| WO | WO 1991/019813 A1 | 12/1991 |
| WO | WO 1994/008050 A1 | 4/1994 |
| WO | WO 1995/007364 A1 | 3/1995 |
| WO | WO 2007/004748 A1 | 1/2007 |
| WO | WO 2010/143714 A1 | 12/2010 |
| WO | WO 2015/163458 A1 | 10/2015 |
| WO | WO 2016/103042 A1 | 6/2016 |

OTHER PUBLICATIONS

Miller et al., "Therapeutic efforts of an anti-ADAMTS-5 antibody on joint damage and mechanical allodynia in a murine model of osteoarthritis," *Osteoarthritis and Cartilage*, 24(2): 299-306 (2016).
Verma et al., "ADAMTS-4 and ADAMTS-5: Key Enzymes in Osteoarthritis," *J. Cell. Biochem.*, 112(12): 3507-3514 (2011).
European Patent Office, Extended European Search Report in European Patent Application No. 18875651.4 (dated Jun. 23, 2021).
Fosang et al., "Drug Insight: aggrecanases as therapeutic targets for osteoarthritis," *Nat. Clin. Pract. Rheumatol.*, 4(8): 420-427 (2008).
Larkin et al., "Translational Development of an ADAMTS-5 Antibody for Osteoarthritis Disease Modification," *Osteoarthritis Cartilage*, 23(8): 1254-1266 (2015).
Malfait et al., "Inhibition of ADAM-TS4 and ADAM-TS5 Prevents Aggrecan Degradation in Osteoarthritic Cartilage," *J. Biol. Chem.*, 277(25): 22201-22208 (2002).
Stanton et al., "ADAMTS5 is the major aggrecanase in mouse cartilage in vivo and in vitro," *Nature*, 434(7033): 648-652 (2005).
Yu, "Development of inhibitory nucleic acid aptamers against aggrecanase for therapeutic applications," Doctor of Philosophy Thesis for University of Hong Kong, abstract and pp. 105-137 (Jun. 2015).
Japanese Patent Office, International Search Report in International Patent Application No. PCT/JP2018/041746 (dated Feb. 12, 2019).

*Primary Examiner* — Brian Whiteman
(74) *Attorney, Agent, or Firm* — Leydig, Voit & Mayer, Ltd.

(57) ABSTRACT

The present invention provides an aptamer containing a sequence shown by the following formula (1) or formula (2):

(1)
GGGGCCUCC-$N_1$-GGACYAAACC (2)
GGGGCCUCC-$N_1$-GGACWYAAACC wherein $N_1$ shows 3 to 24 bases in length, Y is C or U, and W is A or U (uracil is optionally thymine), wherein the aptamer binds to a disintegrin and metalloproteinase with thrombospondin motifs-5 (ADAMTS5).

21 Claims, 10 Drawing Sheets
Specification includes a Sequence Listing.

SEQ ID NO:1

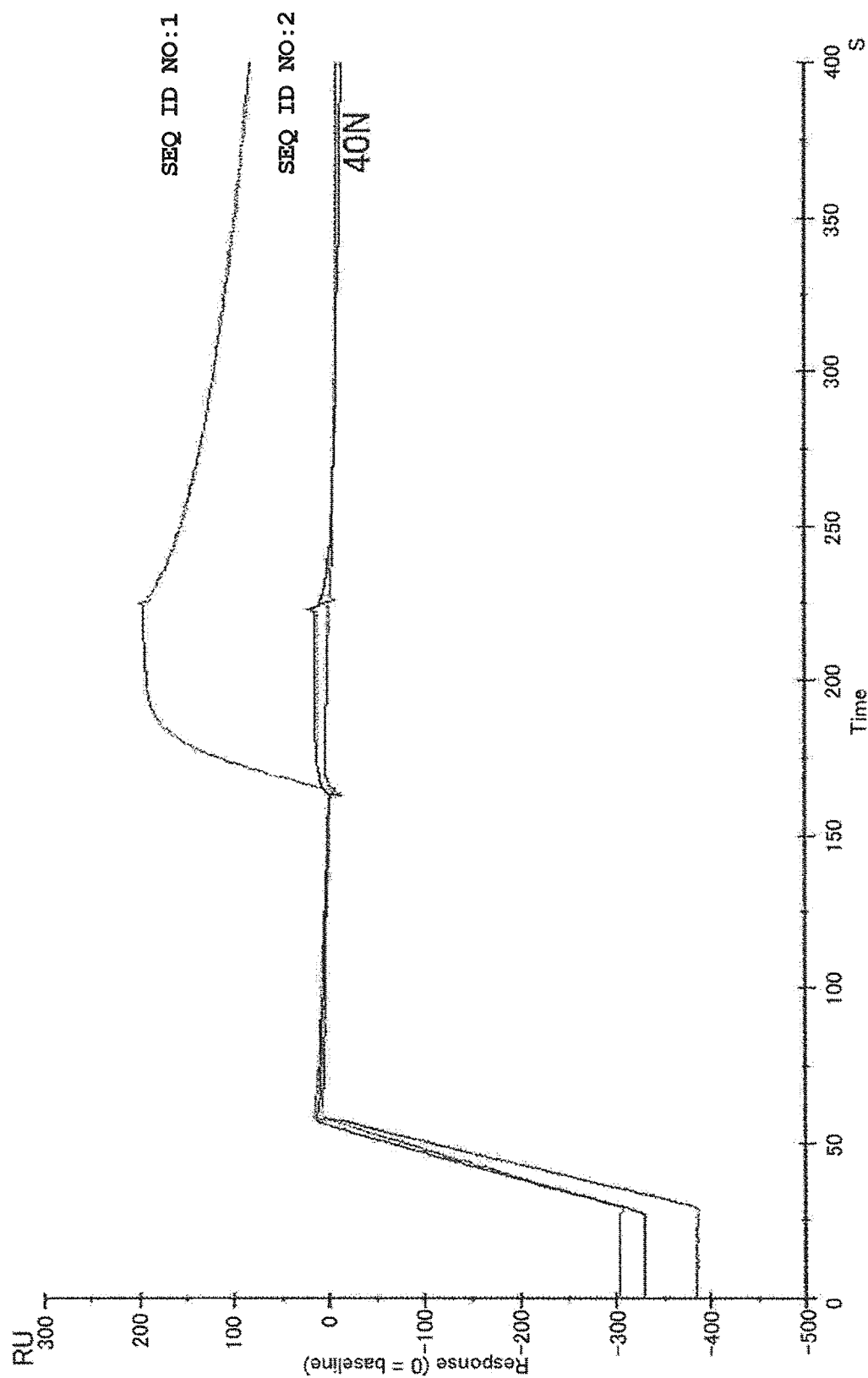

SEQ ID NO:10    SEQ ID NO:11    SEQ ID NO:12

Fig. 5-2
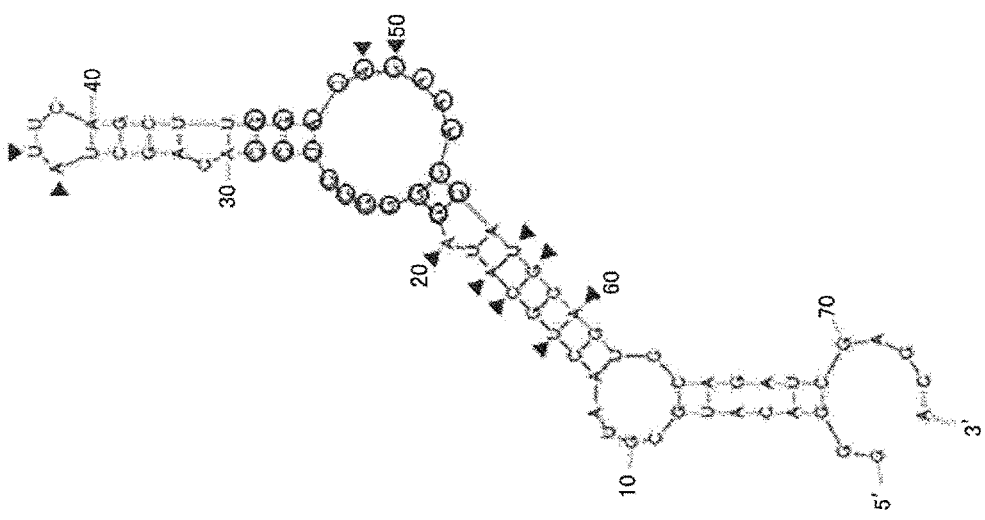
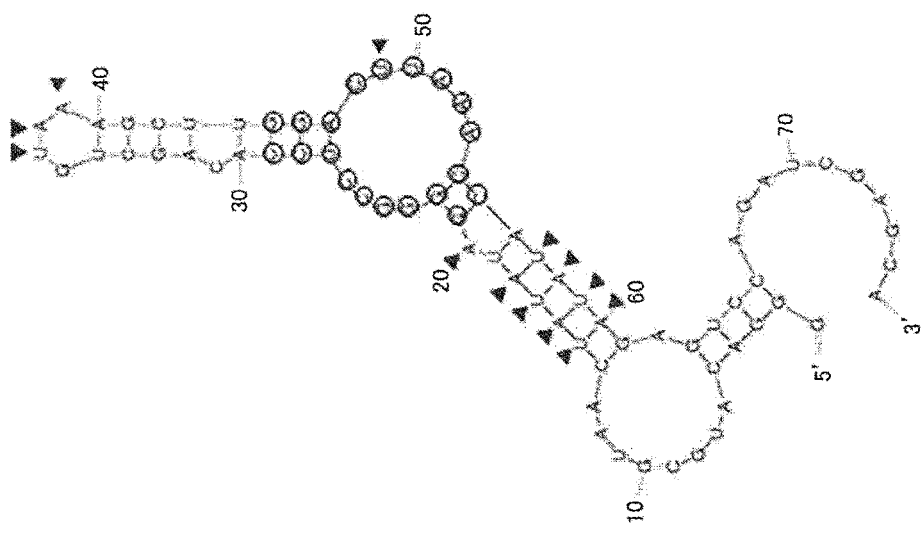
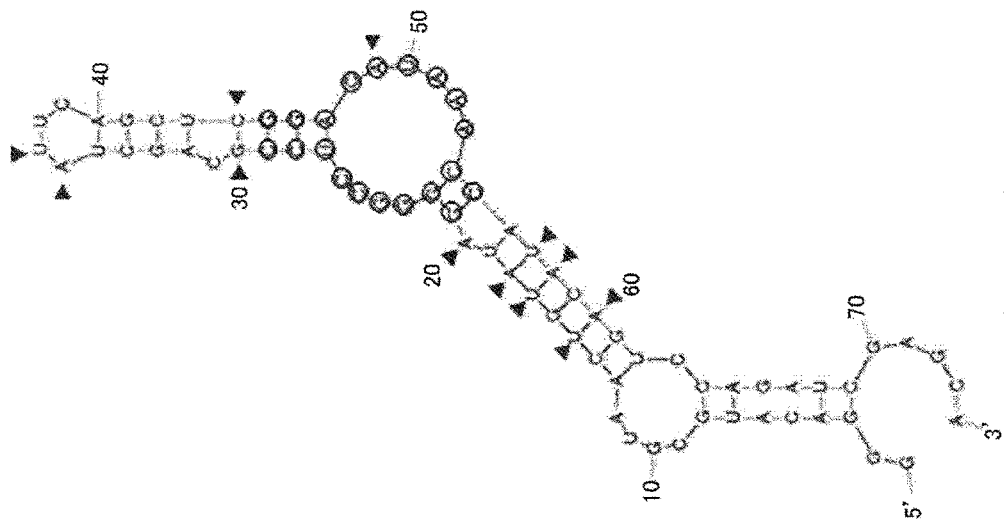

APTAMER FOR ADAMTS5 AND USE FOR APTAMER FOR ADAMTS5

CROSS-REFERENCE TO RELATED APPLICATIONS

This patent application is the U.S. national phase of International Patent Application No. PCT/JP2018/041746, filed on Nov. 9, 2018, which claims the benefit of Japanese Patent Application No. 2017-216280, filed on Nov. 9, 2017, which are incorporated by reference in their entireties herein.

INCORPORATION-BY-REFERENCE OF MATERIAL ELECTRONICALLY SUBMITTED

Incorporated by reference in its entirety herein is a computer-readable nucleotide/amino acid sequence listing submitted concurrently herewith and identified as follows: 14,948 bytes ASCII (Text) file named "748845Sequence-Listing-Replacement-2nd.txt," created Aug. 30, 2021.

TECHNICAL FIELD

The present invention relates to an aptamer for ADAMTS5, a method for utilizing same and the like.

BACKGROUND ART

ADAMTS5 (A disintegrin and metalloproteinase with thrombospondin motifs-5) is one of the ADAMTS family proteins, and is known to be expressed in chondrocytes and synovial cells, to function as an aggrecan degrading enzyme, and to be a major causative protein in cartilage lesions. Therefore, an ADAMTS5 inhibitor may be useful as a therapeutic agent for cartilage lesions including knee osteoarthritis (non-patent documents 1-4).

In recent years, application of RNA aptamers to therapeutic agents, diagnostic agents, and reagents is attracting attention, and some RNA aptamers are in the stages of clinical trial or practicalization. In December 2004, Macugen, the world's first RNA aptamer drug, was approved in the US as a therapeutic drug for age-related macular degeneration. RNA aptamer is an RNA that specifically binds to target substances such as protein and the like, and can be produced using the SELEX method (Systematic Evolution of Ligands by Exponential Enrichment) (see patent documents 1-3). The SELEX method is a method for selecting RNA that specifically binds to a target substance from a pool of about $10^{14}$ RNAs having different nucleotide sequences. The RNA to be used has a structure in which a random sequence of about 40 residues is sandwiched between primer sequences. This RNA pool is associated with the target substance, and only the RNA bound to the target substance is collected using a filter or the like. The recovered RNA is amplified by RT-PCR and used as a template for the next round. By repeating this operation about 10 times, an RNA aptamer that specifically binds to a target substance is sometimes obtained.

DOCUMENT LIST

Patent Documents patent document 1: WO 91/19813
patent document 2: WO 94/08050
patent document 3: WO 95/07364

Non-Patent Documents non-patent document 1: J Biol Chem. 2002 Jun. 21; 277(25):22201-8
non-patent document 2: Nature. 2005 Mar. 31; 434(7033):648-52
non-patent document 3: Nat Clin Pract Rheumatol. 2008 August; 4(8):420-7
non-patent document 4: Osteoarthritis Cartilage. 2015 August; 23(8):1254-66

SUMMARY OF THE INVENTION

Problems to be Solved by the Invention

The present invention aims to provide an aptamer for ADAMTS5 and a method for utilizing the same, and the like.

Means of Solving the Problems

The present inventors have conducted intensive studies in an attempt to solve the aforementioned problem and succeeded in preparing an aptamer of good quality for ADAMTS5, which resulted in the completion of the present invention.

Accordingly, the present invention is as follows.

[1] An aptamer comprising a sequence shown by the following formula (1) or formula (2):

$$(1) \quad \text{GGGGCCUCC-N}_1\text{-GGACYAAACC} \quad (\text{SEQ ID NO: 55})$$

$$(2) \quad \text{GGGGCCUCC-N}_1\text{-GGACWYAAACC} \quad (\text{SEQ ID NO: 56})$$

wherein $N_1$ shows 3 to 24 bases in length, Y is C or U, and W is A or U (uracil is optionally thymine), wherein the aptamer binds to a disintegrin and metalloproteinase with thrombospondin motifs-5 (ADAMTS5).

[2] The aptamer of [1], wherein the aptamer has a potential secondary structure shown by the following formula (1)' (SEQ ID NO: 55) or formula (2)' (SEQ ID NO: 56):

(2)'

[Structural diagram labeled SL1 showing stem-loop structure with bases C-G, C-G, U-A-C, C-W, G-Y, G-A, G-A, G-C-A, G-C, 5' 3']

wherein the part of

[Small stem-loop diagram]

in the formula (1)' and the formula (2)' shows a stem-loop structure optionally having a bulge structure and is the $N_1$ part, Y is C or U, and W is A or U.

[3] The aptamer of [1] or [2], wherein the aptamer inhibits the activity of ADAMTS5.

[4] The aptamer of any of [1] to [3], wherein the aptamer has a base length of not more than 80.

[5] The aptamer of any of [1] to [4], wherein W is U.

[6] The aptamer of any of [1] to [4], wherein Y is U.

[7] The aptamer of any of [1] to [6], wherein $N_1$ is the formula (3)

(3) $X_1CAGCN_2GCUX_2$ (SEQ ID NO: 57)

wherein $N_2$ shows nucleotides in any number of 3 to 15, and $X_1$ and $X_2$ show a combination of A/U bases or G/C bases.

[8] The aptamer of [7], wherein the number of nucleotides for $N_2$ is 4.

[9] The aptamer of [1], comprising any of the nucleotide sequences of the following (a), (b) and (c):

(a) a nucleotide sequence selected from any of SEQ ID NOs: 1, 3-6, 10-14, 16-45 (uracil is optionally thymine);

(b) a nucleotide sequence selected from any of SEQ ID NOs: 1, 3-6, 10-14, 16-45 (uracil is optionally thymine) wherein one to several nucleotides are substituted, deleted, inserted or added; and (c) a nucleotide sequence having identity of not less than 70% with a nucleotide sequence selected from any of SEQ ID NOs: 1, 3-6, 10-14, 16-45 (uracil is optionally thymine).

[10] The aptamer of [9], wherein at least one nucleotide contained in the aptamer is modified or altered.

[11] The aptamer of any of [1] to [10], wherein a hydroxyl group at the ribose 2'-position of each pyrimidine nucleotide contained in the aptamer is the same or different and unsubstituted or substituted by an atom or a group selected from the group consisting of a hydrogen atom, a fluorine atom and a methoxy group.

[12] The aptamer of any of [1] to [11], wherein the hydroxyl group at the ribose 2'-position of each purine nucleotides contained in the aptamer is the same or different and unsubstituted or substituted by an atom or a group selected from the group consisting of a hydrogen atom, a fluorine atom and a methoxy group.

[13] A complex comprising the aptamer of any of [1] to [12] and the functional substance.

[14] A medicament comprising the aptamer of any of [1] to [12] or the complex of [13].

[15] The medicament of [14], wherein the medicament is a therapeutic drug for a disease caused by excessive decomposition of Aggrecan.

[16] The medicament of [15], wherein the disease caused by excessive decomposition of Aggrecan is arthritis or knee osteoarthritis.

[17] A method for detecting ADAMTS5, comprising using the aptamer of any of [1] to [12] or the complex of [13].

[18] A method for treating a disease caused by excessive decomposition of Aggrecan, comprising administering the aptamer of any of [1] to [12] or the complex of [13], or the medicament of [14] to a target.

[19] The aptamer of any of [1] to [12], the complex of [13], or the medicament of [14] for use in treating a disease caused by excessive decomposition of Aggrecan.

[20] Use of the aptamer of any of [1] to [12] or the complex of [13] in producing a medicament for treating a disease caused by excessive decomposition of Aggrecan.

Effect of the Invention

The aptamer or complex of the present invention may be useful as a therapeutic drug for arthritis or knee osteoarthritis. The aptamer or complex of the present invention may also be useful for purification and concentration of ADAMTS5, labeling of ADAMTS5, and detection and quantification of ADAMTS5.

BRIEF DESCRIPTION OF THE DRAWINGS

FIG. 2 is a sensorgram showing that an aptamer having a nucleotide sequence shown in SEQ ID NO: 1 binds to ADAMTS5.

FIG. 5-1 shows the secondary structure of an aptamer having the nucleotide sequence shown in SEQ ID NOs: 16 to 19 as predicted from the MFOLD program.

FIG. 5-2 shows the secondary structure of an aptamer having the nucleotide sequence shown in SEQ ID NOs: 20, 21 and 25 as predicted from the MFOLD program.

FIG. 7-1 shows the secondary structure of an aptamer having the nucleotide sequence shown in SEQ ID NOs: 30 to 35 as predicted from the MFOLD program.

FIG. 7-2 shows the secondary structure of an aptamer having the nucleotide sequence shown in SEQ ID NOs: 36 to 41 as predicted from the MFOLD program.

FIG. 7-3 shows the secondary structure of an aptamer having the nucleotide sequence shown in SEQ ID NOs: 42 to 45 as predicted from the MFOLD program.

DESCRIPTION OF EMBODIMENTS

Figure 1:
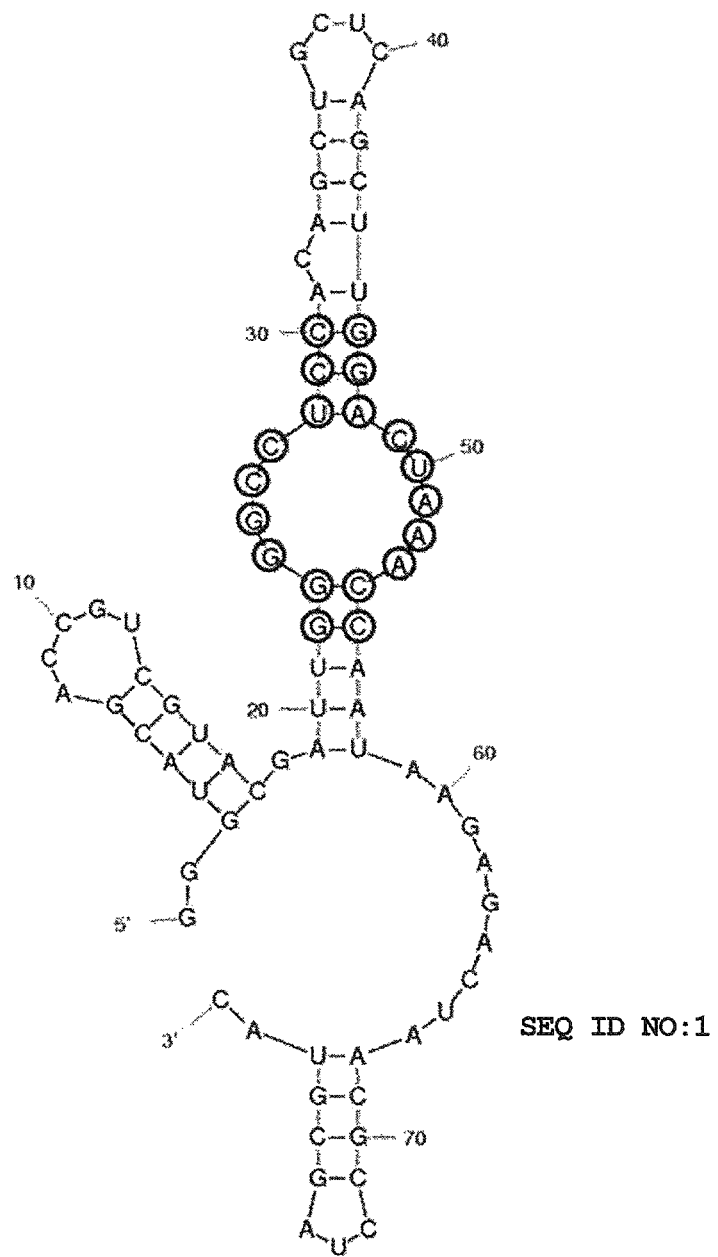
FIG. 1 shows the secondary structure of an aptamer having the nucleotide sequence shown in SEQ ID NO: 1 as predicted from the MFOLD program.

The present invention provides an aptamer having a binding activity to ADAMTS5. The aptamer of the present invention can inhibit the activities of ADAMTS5 (aggrecanase activity and the like).

An aptamer refers to a nucleic acid molecule having a binding activity to a particular target molecule. The aptamer can inhibit the activity of a particular target molecule by binding to the particular target molecule. The aptamer of the present invention may be an RNA, a DNA, a modified nucleic acid or a mixture thereof. The aptamer of the present invention can also be in a linear or circular form.

The present invention provides an aptamer having a binding activity to ADAMTS5. In one embodiment, the aptamer of the present invention can inhibit ADAMTS5 activity by binding to ADAMTS5.

ADAMTS5 is a protein expressed by chondrocytes, synovial cells and the like, and is, for example, a protein having an amino acid sequence represented by Q9UNA0 in UniprotKB. ADAMTS5 in the present invention can be produced not only in the body of animals, but also using mammalian cells of mouse and the like, insect cells, and cultured cells such as *Escherichia coli* and the like, and can be further produced by chemical synthesis. When it is produced using cultured cells or chemical synthesis, a variant can be easily produced by a method known per se. The "variant" of ADAMTS5 here means a protein or peptide in which one to several amino acids of the amino acid sequence of known ADAMTS5 are substituted, deleted, added and the like, or a protein or peptide consisting of a part of the amino acid sequence of known ADAMTS5 and having at least one of the activities that ADAMTS5 inherently has. When the amino acid is substituted or added, the amino acid may be a natural amino acid or an unnatural amino acid. The ADAMTS5 in the present invention includes these variants.

ADAMTS5 is cleaved in the prodomain and secreted as an active form. Thereafter it is cleaved in the middle of the C-terminal Cys-rich domain by self-digestion, and also exists as a truncate form. The aptamer of the present invention binds to any ADAMTS5 and can inhibit the activity of any ADAMTS5.

In one embodiment, the present invention provides an ADAMTS5-binding aptamer containing a sequence shown by the following formula (1) or formula (2):

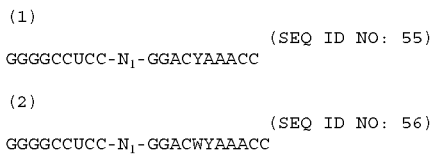

wherein $N_1$ is any number of 3 to 24 nucleotides, Y is C or U, and W is A or U (uracil is optionally thymine).

The inhibitory activity against ADAMTS5 means an inhibitory ability against any activity that ADAMTS5 has. For example, it is known that ADAMTS5 has an activity to decompose aggrecan. Therefore, the inhibitory activity against ADAMTS5 may be an activity to inhibit decomposition of aggrecan by ADAMTS5.

Therefore, when the aptamer of the present invention binds to ADAMTS5 and inhibits the aggrecan decomposition activity of ADAMTS5, the aptamer is considered to be useful for the treatment of diseases caused by excessive decomposition of aggrecan.

The aptamer of the present invention can exhibit an inhibitory activity against ADAMTS5 derived from any mammals. Such mammals include primates (e.g., human, monkey), rodents (e.g., mouse, rat, guinea pig), and companion animals, domestic animals and working animals (e.g., dog, cat, horse, bovine, goat, sheep, swine).

The aptamer of the present invention may be an aptamer having specificity to ADAMTS5 that it binds to ADAMTS5 but does not bind to ADAMTS4 having a similar aggrecan decomposition ability.

It has been reported that ADAMTS5 shows about 1000 times higher aggrecan decomposition activity than ADAMTS4 (J. Biol. Chem. 2007, 282:18294-18306), and it has also been reported that ADAMTS5 is important for the onset of arthritis (non-patent document 2). The aptamer of the present invention is useful for the treatment of diseases caused by excessive decomposition of aggrecan by ADAMTS5.

In the above-mentioned formula (1) and formula (2), $N_1$ shows any number of nucleotides. In the present specification, the "base" means any of adenine (A), guanine (G), cytosine (C), uracil (U) and thymine (T) constituting a nucleic acid.

The number of nucleotides for $N_1$ is not particularly limited as long as an aptamer containing the nucleotide sequences represented by the formula (1) and the formula (2) binds to ADAMTS5. It is preferably 3-24, 5-18, 6-15, 8-15, 11-15, 13-15 and the like. More preferably, it is 6-15, 8-15, 11-15, 13-15, and most preferably 13-15.

When the number of nucleotides for $N_1$ is less than 3, a loop structure cannot be formed at the $N_1$ part as mentioned below. When the number of nucleotides for $N_1$ exceeds 24, the sequence and structure of the $N_1$ part may influence the function of the whole aptamer and the binding activity to ADAMTS5 may be lost in some cases.

In a preferable embodiment, in the above-mentioned formula (1) and formula (2), $N_1$ has the number of bases and nucleotide sequences necessary for forming a stem-loop structure by binding to ADAMTS5. The stem part of the stem-loop structure formed by the nucleotide sequence for $N_1$ may have a bulge structure.

In the above-mentioned formula (1) and formula (2), UCC in the GGGGCCUCC part and GGA in the GGACYAAACC (SEQ IN NO: 58) or GGACWYAAACC (SEQ ID NO: 59) part form base pairs and take a stem structure. As mentioned below, it is important that $N_1$ in the above-mentioned formula (1) and formula (2), and UCC and GGA adjacent to $N_1$ form a stem-loop structure when the aptamer of the present invention binds to ADAMTS5.

Therefore, the stem-loop structure formed by the nucleotide sequences for $N_1$ may be a loop structure alone as long as the obtained aptamer binds to ADAMTS5. That is, the minimum number of bases of the loop part is 3, and the minimum number of bases of the stem part is 0 (in the formula (1) and formula (2), UCC of the GGGGCCUCC part and GGA of the GGACYAAACC (SEQ IN NO: 58) or GGACWYAAACC (SEQ IN NO: 59) part form a stem structure and N₁ forms only a loop part).

The length of the loop part is not particularly limited as long as the aptamer of the present invention binds to ADAMTS5 and may be, for example, 3-15, 3-11, 4-11 and the like. It is preferably 3-11, more preferably 3-8, further preferably 3-5, most preferably 3 or 4.

The nucleotide sequence of the loop part is variable as long as the aptamer of the present invention binds to ADAMTS5.

Alternatively, the aptamer of the present invention may be an ADAMTS5-binding aptamer containing the following (a), (b) or (c)
(a) a nucleotide sequence selected from any of SEQ ID NOs: 1, 3, 4-6, 10-44;
(b) a nucleotide sequence selected from any of SEQ ID NOs: 1, 3, 4-6, 10-44 wherein one or several nucleotides other than a sequence represented by GGGGCCUCC and GGA-CYAAACC (SEQ IN NO: 58) or GGACWYAAACC (SEQ IN NO: 59) in GGGGCCUCC-N₁-GGACYAAACC (SEQ IN NO: 55) or GGGGCCUCC-N₁-GGACWYAAACC (SEQ IN NO: 56) (wherein N₁ is any number of 3 to 24 nucleotides, Y is C or U, and W is A or U) is/are substituted, deleted, inserted or added; or
(c) a nucleotide sequence having identity of not less than 70% (preferably, not less than 80%, not less than 85%, not less than 90%, not less than 95%, not less than 96%, not less than 97%, not less than 98%, not less than 99%) with a nucleotide sequence selected from SEQ ID NOs: 1, 3, 4-6, 10-44 (wherein the sequences represented by GGGGC-CUCC and GGACYAAACC (SEQ ID NO: 58) or GGACWYAAACC (SEQ ID NO: 59) in GGGGCCUCC-N₁-GGACYAAACC (SEQ ID NO: 55) or GGGGCCUCC-N₁-GGACWYAAACC (SEQ ID NO: 56) wherein N₁, Y and W are the same as the above are the same).

In a more preferable embodiment, N₁ is represented by the formula (3)

$$X_1CAGCN_2GCUX_2 \text{ (SEQ ID NO: 57)} \quad (3)$$

wherein N₂ is any number of 3 to 15 nucleotides, and X₁ and X₂ are a combination of A/U bases or G/C bases.

In the formula (3), X₁CAGC and GCUX₂ form a stem structure (including bulge structure) and the N₂ part forms a loop structure.

The number of nucleotides for N₂ is typically 3-15, preferably 3-11, more preferably 3-8, further preferably 3-5, most preferably 4.

The sequence of the loop part for N₂ is not particularly limited as long as the formula (3) as a whole forms a stem-loop structure, and may be any combination of bases. However, in a preferable embodiment, N₂ in the formula (3) is any of GCUC, UUCG, GUAA, and AUUC.

X₁ and X₂ are a combination of A/U bases or G/C bases. It is preferably a combination of A for X₁ and U for X₂ or a combination of G for X₁ and C for X₂, more preferably, a combination of A for X₁ and U for X₂.

The sequence represented by the above-mentioned (1) or (2) can form a potential secondary structure shown by the following formula (1)' (SEQ ID NO: 55) or (2)' (SEQ ID NO: 56):

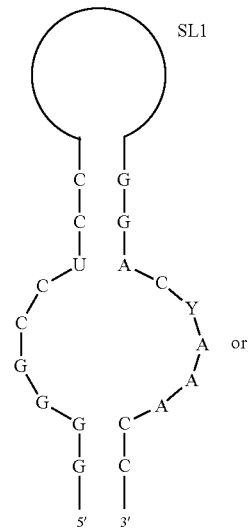

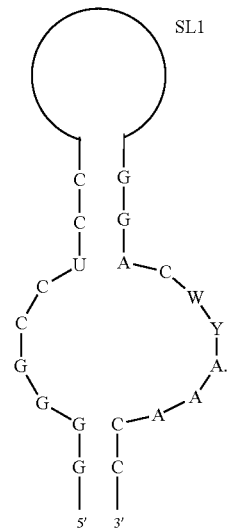

The aptamer of the present invention is considered to show various activities since it has the above-mentioned structure in the part of the sequence shown by the above-mentioned (1) or (2). The structure of the formula (1)' or (2)' corresponds to the above-mentioned formula (1) or (2), respectively.

In addition, a stem structure (including bulge structure) can be preferably formed by an interaction between the sequences following the 5'-terminus and 3'-terminus in the above-mentioned structure.

For the aptamer of the present invention to show various activities, a stem-loop structure shown by the above-mentioned potential secondary structure is desirably maintained. While a stem structure can be formed by complementary base pairs, the number of base pairs is not particularly limited. In the stem structure, even when base pairs are not formed in a part thereof, the aptamer activity is maintained as long as a stem structure is constituted as a whole.

The stem-loop part SL1 at the top of the formula (1)' or (2)' corresponds to the N₁ part in the formula (1) and the formula (2).

It is considered that the stem-loop structure represented by the formula (1)' or (2)' is more stably maintained when N₁ takes the sequence represented by the above-mentioned formula (3). That is, the stem structure (including bulge structure) formed by ACAGC and GCUU in the formula (3) forms the stem structure of the SL1 part in the formula (1)' or (2)', and N$_2$ in the formula (3) forms the loop structure of the SL1 part.

In the formula (1) and the formula (2), UCC in the GGGGCCUCC part and GGA in the GGACYAAACC (SEQ ID NO: 58) or GGACWYAAACC (SEQ ID NO: 59) part form base pairs and take a stem structure. Furthermore, the first GG in the GGGGCCUCC part and the last CC in the GGACYAAACC (SEQ ID NO: 58) or GGACWYAAACC (SEQ ID NO: 59) part form a stem structure, and the remaining sequence forms an internal loop.

The sole difference between the above-mentioned formula (1) and formula (2) is the presence or absence of W. As is clear from the formula (1)' or (2)', an internal loop is constituted around base W. As sufficiently shown in the Examples, the presence or absence of W does not cause a marked difference in the structure or activity. Therefore, all aptamers of the present invention having the sequences represented by the formula (1) and the formula (2) were invented on the basis of the same technical idea.

The length of the aptamer of the present invention is not particularly limited, and can typically be about 25-about 200 nucleotides. For example, it may be not less than about 25 nucleotides (e.g., not less than 30 nucleotides, not less than 31 nucleotides, not less than 32 nucleotides, not less than 33 nucleotides), preferably not less than 25 nucleotides, more preferably not less than 30 nucleotides, further preferably not less than 33 nucleotides. Also, for example, it may be not more than about 100 nucleotides, typically not more than about 80 nucleotides, preferably not more than about 70 nucleotides, more preferably not more than about 60 nucleotides, further preferably not more than about 50 nucleotides, further preferably not more than about 45 nucleotides (e.g., not more than 44 nucleotides, not less than 43 nucleotides, not more than 42 nucleotides, not more than 41 nucleotides, not more than 40 nucleotides). When the total number of nucleotides is smaller, chemical synthesis and mass-production will be easier, and there is a major advantage in terms of cost. It is also considered that chemical modification is easy, stability in the body is high, and toxicity is low.

The length of the aptamer of the present invention may therefore be typically about 25-about 200 nucleotides, preferably 25-80 nucleotides, more preferably 25-60 nucleotides, further preferably 25-50 nucleotides, most preferably 30-45 nucleotides.

The aptamer of the present invention may be a conjugate selected from the group consisting of a conjugate of a plurality of an aptamer containing a nucleotide sequence represented by the above-mentioned formula (1) (aptamer (A)), a conjugate of a plurality of an aptamer containing a nucleotide sequence represented by the above-mentioned formula (1) wherein 1-several nucleotides are substituted, deleted, inserted or added (aptamer (B)), and a conjugate of 1 or plural aptamers (A) and 1 or plural aptamers (B). These conjugates can also bind to ADAMTS5.

The conjugation here can be achieved by tandem binding. In the conjugation, a linker may be utilized. As the linker, nucleotide chains (e.g., 1 to about 20 nucleotides) and non-nucleotide chains (e.g., —(CH$_2$)$_n$— linker, —(CH$_2$CH$_2$O)$_n$— linker, hexaethylene glycol linker, TEG linker, peptide-containing linker, —S—S— bond-containing linker, —CONH— bond-containing linker, —OPO$_3$— bond-containing linker) can be mentioned. The plurality as mentioned in the above-described conjugate of a plurality thereof is not particularly limited, as long as it is two or more, and the plurality can be, for example, 2, 3 or 4.

The respective nucleotides contained in the aptamer of the present invention are the same or different, and may be a nucleotide containing a hydroxy group at the 2'-position of ribose (e.g., ribose of pyrimidine nucleotide, ribose of purine nucleotide) (namely, natural ribonucleotide) or a nucleotide in which a hydroxy group is substituted (modified) by any atom or group at the 2'-position of ribose (sometimes to be indicated as "modified nucleotide" in the present invention).

For example, a nucleotide substituted by such any atom or group exemplified by a hydrogen atom, a fluorine atom or an —O— alkyl group (e.g., —O-Me group), an —O-acyl group (e.g., —O—CHO group), an amino group (e.g., —NH$_2$ group) can be mentioned. The aptamer of the present invention may be a modified nucleotide in which at least one kind (e.g., 1, 2, 3 or 4 kinds) of nucleotide contains a hydroxyl group, or the above-described any atom or group, for example, at least two kinds (e.g., 2, 3 or 4 kinds) of atoms or groups selected from the group consisting of a fluorine atom, a hydroxyl group and —O-Me group, at the 2'-position of ribose.

In the aptamer of the present invention, all pyrimidine nucleotides may be a nucleotide wherein the 2'-position of ribose is a fluorine atom, or the fluorine atoms are the same or different and unsubstituted, or substituted by the aforementioned any atom or group, preferably, the same atom or group selected from the group consisting of a hydrogen atom, a hydroxyl group and a methoxy group. Particularly, when a production method using the below-mentioned DuraScribe™ T7 Transcription Kit (manufactured by Epicentre) is applied as a production method of the aptamer of the present invention, an aptamer, in which the 2'-position of the ribose of all pyrimidine nucleotides is fluorinated, is obtained. The aptamer of the present invention in which a fluorine atom is substituted by the above-mentioned other atom or group can be produced by the below-mentioned method.

In the aptamer of the present invention, all purine nucleotides may be nucleotides in which the 2'-position of ribose is a hydroxy group, or nucleotides in which the hydroxy group is the same or different, unsubstituted, or substituted by the aforementioned any atom or group, preferably, an atom or group selected from the group consisting of a hydrogen atom, a methoxy group and a fluorine atom. The aptamer of the present invention in which a hydroxy group is substituted by the above-mentioned other atom or group can be produced by the below-mentioned method.

In the aptamer of the present invention, all pyrimidine nucleotides may be nucleotides in which a fluorine atom at the 2'-position of ribose is substituted by the aforementioned any atom or group, for example, the same atom or group selected from the group consisting of a hydrogen atom, a hydroxy group and an —O-Me group.

In the aptamer of the present invention, all purine nucleotides may be nucleotides in which a hydroxy group at the 2'-position of ribose is substituted by the aforementioned any atom or group, for example, the same atom or group selected from the group consisting of a hydrogen atom, a fluorine atom, and an —O-Me group.

In a preferable embodiment, each pyrimidine nucleotide contained in the aptamer of the present invention is a nucleotide containing a fluorine atom at the 2'-position of ribose, and each purine nucleotide is a nucleotide containing a hydroxy group at the 2'-position of ribose. In another embodiment, the fluorine atom at the 2'-position of ribose of the above-mentioned each pyrimidine nucleotide is independently optionally substituted by an atom or group selected from the group consisting of a hydrogen atom, a hydroxy group and a methoxy group, and the hydroxy group at the 2'-position of ribose of the above-mentioned each purine nucleotide is each independently optionally substituted by an atom or group selected from the group consisting of a hydrogen atom, a methoxy group and a fluorine atom.

In this Description, the nucleotides constituting the aptamer are assumed to be RNAs (i.e., the sugar groups are assumed to be ribose) in describing how the sugar groups are modified in the nucleotides. However, this does not mean that DNA is exempted from the aptamer-constituting nucleotides, and a modification should read as a modification of DNA as appropriate. When the nucleotide constituting the aptamer is DNA, for example, substitution of a hydroxyl group at the 2'-position of ribose by X should read as a substitution of the hydrogen atom at the 2'-position of deoxyribose by X.

In the aptamer of the present invention, the binding property to ADAMTS5, inhibitory activity against aggrecan decomposition by ADAMTS5, aptamer stability, drug deliverability, stability in blood and the like can be enhanced by substituting uracil with thymine.

In the aptamer of the present invention, 1 or several, for example, 1-2, 1-3, 1-4, 1-5 nucleotides of phosphoric acid diester bond in the nucleotide may be modified or substituted by any substituent(s). For example, phosphoric acid diester bond may be substituted by a phosphorothioate bond, a phosphorodithioate bond, an alkylphosphonate bond, a phosphoramidate bond and the like. Here, for example, "nucleotide is substituted by a phosphorothioate bond" means that a phosphate group in a binding site between adjacent nucleotides is sulfurated, that is, a phosphodiester bond is converted to a phosphorothioate bond.

In the aptamer of the present invention, one or several, for example, 1-2, 1-3, 1-4, 1-5 nucleotides may be substituted by Bridged Nucleic Acid (BNA) or Locked Nucleic Acid (LNA) to stabilize aptamer and improve the activity thereof. As used herein, the "bridged nucleic acid" refers to one having a structure wherein the binding affinity to a complementary sequence is enhanced by restricting the degree of freedom of nucleic acid by intramolecular crosslinking, and acquire nuclease resistance. Examples thereof include, but are not limited to, 2',4'-BNA (Locked Nucleic Acid (LNA)), 2'-O,4'-C-ethylene-bridged Nucleic Acid (ENA) and the like.

The aptamer of the present invention is an aptamer that binds to ADAMTS5, further preferably an aptamer that can inhibit the activities of ADAMTS5. Whether the aptamer of the present invention binds to ADAMTS5 can be evaluated by a test utilizing, for example, the surface plasmon resonance method of Example 1 and the like. In addition, whether the aptamer of the present invention can inhibit the activities of ADAMTS5 can be evaluated by a test utilizing, for example, the aggrecan of Example 1 and the like.

The aptamer of the present invention may be one wherein a sugar residue (e.g., ribose) of each nucleotide has been modified to increase the ADAMTS5 binding activity, stability, drug deliverability and the like. As examples of the modification in a sugar residue, substitution of the oxygen atom at the 2'-position, the 3'-position and/or the 4'-position of the sugar residue with another atom, and the like can be mentioned. As the kind of the modification, fluorination, O-alkylation (e.g., O-methylation, O-ethylation), O-allylation, S-alkylation (e.g., S-methylation, S-ethylation), S-arylation, and amination (e.g., —NH$_2$) can be mentioned. In addition, examples thereof include 4'-SRNA wherein the 4'-position oxygen is replaced with sulfur, LNA (Locked Nucleic Acid) wherein the 2'-position and the 4'-position are crosslinked via methylene, 3'-N-phosphoramidate nucleic acid wherein the 3'-position hydroxyl group is replaced with an amino group and the like. The aptamer of the present invention is sometimes produced with a given modification of the oxygen atom at the 2'-position of ribose of pyrimidine nucleotide, due to the production method thereof. When a production method using the below-mentioned DuraScribe™ T7 Transcription Kit (manufactured by Epicentre) is applied as a production method of the aptamer of the present invention, an aptamer wherein the 2'-position of ribose of preferably all pyrimidine nucleotides is fluorinated is produced. Therefore, it is possible to produce various variations of aptamers having enhanced activity even though the base sequence is the same, by applying such alteration in the sugar residue to the obtained aptamer. From the above, the aptamer of the present invention can be preferably an aptamer wherein a sugar residue of at least one nucleotide is modified. Such modification of the sugar residue can be performed by a method known per se (refer to e.g. Sproat et al., (1991), Nucl. Acid. Res. 19, 733-738; Cotton et al., (1991), Nucl. Acid. Res. 19, 2629-2635; Hobbs et al., (1973), Biochemistry 12, 5138-5145). To be specific, an aptamer wherein the hydroxyl group at the 2'-position of ribose is substituted by an atom or group selected from the group consisting of a hydrogen atom, a hydroxyl group and a methoxy group can be produced by using, as a base, an aptamer wherein the hydroxyl group at the 2'-position of ribose of all pyrimidine nucleotides is substituted by a fluoro group.

The aptamer of the present invention may also have a nucleic acid base (e.g., purine or pyrimidine) altered (e.g., chemical substitution) to increase the ADAMTS5 binding activity, stability, drug deliverability and the like. As examples of such alterations, pyrimidine alteration at 5-position, purine alteration at 6- and/or 8-position(s), alteration with an extracyclic amine, substitution with 4-thiouridine, and substitution with 5-bromo or 5-iodo-uracil can be mentioned. In addition, the phosphate group contained in the aptamer of the present invention may be altered to confer resistance to nuclease and hydrolysis. For example, the P(O)O group may be substituted with P(O)S (thioate), P(S)S (dithioate), P(O)NR$_2$ (amidate), P(O)R, R(O)OR', CO or CH$_2$ (formacetal) or 3'-amine (—NH—CH$_2$—CH$_2$—) [wherein each unit of R or R' is independently H or a substituted or unsubstituted alkyl (e.g., methyl, ethyl)].

The linking group is, for example, —O—, —N— or —S—, and nucleotides can bind to an adjoining nucleotide via these linking groups.

The alterations may also include alterations such as capping at 3' and 5'.

An alteration can further be performed by adding to an end a polyethyleneglycol, amino acid, peptide, inverted dT, nucleic acid, nucleosides, myristoyl, lithocolic-oleyl, docosanyl, lauroyl, stearoyl, palmitoyl, oleoyl, linoleoyl, other lipids, steroids, cholesterol, caffeine, vitamins, dyes, fluorescent substances, anticancer agents, toxins, enzymes, radioactive substances, biotin and the like. For such alterations, see, for example, U.S. Pat. Nos. 5,660,985 and 5,756,703.

Particularly, when alteration is performed by terminus addition of PEG, the molecular weight of PEG is not particularly limited, and is preferably 1000-100000, more preferably 30000-90000. PEG may be linear or branched into two or more chains (multi-arm PEG).

Such PEG is not particularly limited, and those of ordinary skill in the art can appropriately select and use 5 commercially available or known PEG (see, e.g., www.pegdrug.com/peg_product/branched.html). Specific preferable examples of PEG to be applied to the aptamer of the present invention include 2-branched GS type PEG having a molecular weight of 40000 (SUNBRIGHT GL2-400GS2 manufactured by NOF CORPORATION), 2-branched TS type PEG having a molecular weight of 40000 (SUNBRIGHT GL2-400TS manufactured by NOF CORPORATION), 4-branched TS type PEG having a molecular weight of 40000 (SUNBRIGHT GL4-400TS manufactured by NOF CORPORATION), 2-branched TS type PEG having a molecular weight of 80000 (SUNBRIGHT GL2-800TS manufactured by NOF CORPORATION), 4-branched TS type PEG having a molecular weight of 80000 (SUNBRIGHT GL4-800TS manufactured by NOF CORPORATION), and the like. In this case, in the aptamer of the present invention, PEG may be directly added to the terminus. It is more preferable that a linker having a group bindable to PEG and the like be added to the terminus thereof, and PEG be added to the aptamer of the present invention via the linker.

The linker for PEG and the aptamer of the present invention is not particularly limited, and carbon chain number, functional group and the like can be appropriately selected according to the binding site, the species of PEG and the like. Examples of such linker include a linker having an amino group. Specifically, when added to the 5'-terminal, ssH Linker (SAFC) or DMS(O)MT-AMINO-MODIFIER (GLEN RESEARCH) can be mentioned, and when added to the 3'-terminal, TFA Amino C-6 lcaa CPG (ChemGenes) and the like can be mentioned. When this linker is selected, for example, an active group of N-hydroxysuccinimide is added to PEG, and reacted with an amino group on the linker side, whereby the aptamer of the present invention can be bound to PEG via the linker.

As PEG and linker, commercially available products can be preferably used. The reaction conditions and the like relating to the binding of PEG, a linker, and an aptamer of the present invention can be appropriately determined by those of ordinary skill in the art.

The aptamer of the present invention can be chemically synthesized as disclosed herein and by a method known per se in the art. An aptamer binds to the target substance in a wide variety of binding modes, such as ionic bonds based on the negative charge of the phosphate group, hydrophobic bonds and hydrogen bonds based on ribose, and hydrogen bonds and stacking interaction based on nucleic acid bases. In particular, ionic bonds based on the negative charge of the phosphate group, which are present in the same number as the number of constituent nucleotides, are strong, and bind to lysine and arginine being present on the surface of the positive charge of protein. For this reason, nucleic acid bases not involved in the direct binding to the target substance can be substituted. In particular, because the region of stem structure has already formed base pairs and faces the inside of the double helical structure, nucleic acid bases are unlikely to bind directly to the target substance. Therefore, even when a base pair is substituted with another base pair, the activity of the aptamer often does not decrease. In structures wherein no base pairs are formed, such as loop structures, provided that the nucleic acid base is not involved in the direct binding to the target molecule, base substitution is possible. Regarding modifications of the 2'-position of ribose, the functional group at the 2'-position of ribose infrequently interacts directly with the target molecule, but in many cases, it is of no relevance, and can be substituted by another modified molecule. Hence, an aptamer, unless the functional group involved in the direct binding to the target molecule is substituted or deleted, often retains the activity thereof. It is also important that the overall three-dimensional structure does not change substantially.

An aptamer can be prepared by utilizing DNA-SELEX method and an improved method thereof (e.g., Ellington et al., (1990), Nature, 346, 818-822; Tuerk et al., (1990), Science, 249, 505-510). In the SELEX method, by increasing the number of rounds or using a competing substance, an aptamer exhibiting a stronger binding potential for the target substance is concentrated and selected. Hence, by adjusting the number of rounds of SELEX and/or changing the competitive condition, aptamers with different binding forces, aptamers with different binding modes, and aptamers with the same binding force or binding mode but different base sequences can be obtained in some cases. The SELEX method comprises a process of amplification by PCR; by causing a mutation by using manganese ions and the like in the process, it is possible to perform SELEX with higher diversity.

The aptamers obtained by SELEX are nucleic acids that exhibit high affinity for the target substance, but this does not mean binding to the active site of the target substance. Therefore, the aptamers obtained by SELEX do not necessarily act on the function of the target substance. ADAMTS5 is a basic protein, and is considered to be likely to allow nucleic acids to bind thereto nonspecifically. It is considered that an aptamer that does not bind to an active site does not influence the activity of the target substance.

Using the active aptamer thus selected, optimized SELEX can be performed to obtain an aptamer possessing higher activity. The optimized SELEX means performing SELEX again after preparing a template wherein an aptamer with a determined sequence is partially randomized or a template doped with about 10 to 30% of random sequences.

An aptamer obtained by SELEX has a length of about 80 nucleotides, and this is difficult to prepare as a pharmaceutical as it is. Hence, it is preferable to repeat try-and-error efforts to shorten the aptamer to a length (e.g., chemical synthesis is possible for not more than about 60 nucleotides, more preferably not more than about 50 nucleotides, further preferably not more than 45 nucleotides) permitting easy chemical synthesis.

Depending on the primer design for an aptamer obtained by SELEX, the ease of the subsequent minimization operation changes. Unless the primer is designed successfully, subsequent development will be impossible even if an aptamer with activity is selected by SELEX. In view of such background, a Tailored-SELEX method capable of affording an aptamer having a shorter base length as compared to the typical SELEX method (Vater et al., Nucleic Acids Res. 31, 2003, e130; Jarosch et al. Nucleic Acids Res. 34, 2006, e86), a Primer-less SELEX method which is an improved version of the Tailored-SELEX method, and the like can also be used.

Aptamers are altered easily since they permit chemical synthesis. For aptamers, by predicting the secondary structure using the MFOLD program, or by predicting the steric structure by X-ray analysis or NMR analysis, it is possible to predict to some extent which nucleotide can be substituted or deleted, and where to insert a new nucleotide. A predicted aptamer with the new sequence can easily be chemically synthesized, and it can be determined whether or not the aptamer retains the activity using an existing assay system.

When a region important to the binding of the obtained aptamer with the target substance is identified by repeated try-and-error efforts as described above, the activity remains unchanged in many cases even when a new sequence is added to both ends of the sequence. The length of the new sequence is not particularly limited.

As already described, modifications can be highly designed or altered, like sequences.

As stated above, aptamers permit a wide range of design or alterations. The present invention also provides a production method of aptamer that enables a wide range of design or alteration of an aptamer comprising a specified sequence (e.g., a sequence corresponding to a portion selected from among stem regions, internal loop regions, hairpin loop regions and single-strand regions: hereinafter, abbreviated as fixed sequence as required).

For example, such production method of aptamer includes production of an aptamer comprising a fixed sequence by using a single kind of nucleic acid molecule consisting of a nucleotide sequence shown by:

sequence for primer (i) - (N) a-fixed sequence- (N) b- sequence for primer (ii)

wherein (N)a represents a nucleotide chain consisting of "a" units of N; (N)b represents a nucleotide chain consisting of "b" units of N; each of the units of N, whether identical or different, is a nucleotide selected from the group consisting of A, G, C, U and T (preferably, A, G, C and U). Each of "a" and "b", whether identical or different, can be any numbers, and can be, for example, 1 to about 100, preferably 1 to about 50, more preferably 1 to about 30, still more preferably 1 to about 20 or 1 to about 10], or plural kinds of nucleic acid molecules (e.g., library of nucleic acid molecule different in the number of a, b etc.) and primer pairs corresponding to the sequences for primer (i) and (ii), respectively.

The present invention also provides a complex comprising the aptamer of the present invention and a functional substance bound thereto. The binding between the aptamer and the functional substance in the complex of the present invention can be a covalent bond or a non-covalent bond. The complex of the present invention can be one wherein the aptamer of the present invention and one or more (e.g., 2 or 3) of functional substances of the same kind or different kinds are bound together. The functional substance is not particularly limited, as far as it newly confers a certain function to an aptamer of the present invention, or is capable of changing (e.g., improving) a certain characteristic which an aptamer of the present invention can possess. As examples of the functional substance, proteins, peptides, amino acids, lipids, sugars, monosaccharides, polynucleotides, and nucleotides can be mentioned. As examples of the functional substance, affinity substances (e.g., biotin, streptavidin, polynucleotides possessing affinity for target complementary sequence, antibodies, glutathione Sepharose, histidine), substances for labeling (e.g., fluorescent substances, luminescent substances, radioisotopes), enzymes (e.g., horseradish peroxidase, alkaline phosphatase), drug delivery vehicles (e.g., liposome, microspheres, peptides, polyethyleneglycols), drugs (e.g., those used in missile therapy such as calicheamycin and duocarmycin; nitrogen mustard analogues such as cyclophosphamide, melphalan, ifosfamide or trofosfamide; ethylenimines such as thiotepa; nitrosoureas such as carmustine; alkylating agents such as temozolomide or dacarbazine; folate-like metabolic antagonists such as methotrexate or raltitrexed; purine analogues such as thioguanine, cladribine or fludarabine; pyrimidine analogues such as fluorouracil, tegafur or gemcitabine; vinca alkaloids such as vinblastine, vincristine or vinorelbine and analogues thereof; podophyllotoxin derivatives such as etoposide, taxans, docetaxel or paclitaxel; anthracyclines such as doxorubicin, epirubicin, idarubicin and mitoxantrone, and analogues thereof; other cytotoxic antibiotics such as bleomycin and mitomycin; platinum compounds such as cisplatin, carboplatin and oxaliplatin; pentostatin, miltefosine, estramustine, topotecan, irinotecan and bicalutamide), and toxins (e.g., ricin toxin, liatoxin and vero toxin) can be mentioned. These functional molecules are finally removed in some cases. Furthermore, the molecules may be peptides that can be recognized and cleaved by enzymes such as thrombin, matrix metalloproteinase (MMP), and Factor X, and may be polynucleotides that can be cleaved by nucleases or restriction endonuclease.

The aptamer and the complex of the present invention can be used as, for example, medicaments, diagnostic reagents, test reagents or reagents. Particularly, they are useful as medicaments for the treatment or prophylaxis of cartilage diseases such as arthritis and knee osteoarthritis, or diagnostic agents, test reagents or reagents.

The target disease of the above-mentioned medicament includes diseases considered to be caused by excessive decomposition of aggrecan, for example, many diseases, disease states and the like such as pain, chronic pain, neuropathic pain, postoperative pain, rheumatoid arthritis, osteoarthritis (e.g., knee osteoarthritis etc.), sports trauma, arthritis (e.g., erosive arthritis etc.), askylosing spondylitis, neuralgia, neuropathy, pain sensation, nerve damage, ischemia, neurodegeneration, cartilage degeneration, cerebral apoplexy, incontinence, inflammatory diseases, irritable bowel syndrome, periodontal disease, abnormal angiogenesis, tumor infiltration, and metastasis, corneal ulcer, and complications of diabetes can be mentioned.

The medicament of the present invention can be one formulated with a pharmaceutically acceptable carrier. As examples of the pharmaceutically acceptable carrier, excipients such as sucrose, starch, mannit, sorbit, lactose, glucose, cellulose, talc, calcium phosphate, and calcium carbonate; binders such as cellulose, methylcellulose, hydroxypropylcellulose, polypropylpyrrolidone, gelatin, gum arabic, polyethylene glycol, sucrose, and starch; disintegrants such as starch, carboxymethylcellulose, hydroxypropylstarch, sodium-glycol-starch, sodium hydrogen carbonate, calcium phosphate, and calcium citrate; lubricants such as magnesium stearate, Aerosil, talc, and sodium lauryl sulfate; flavoring agents such as citric acid, menthol, glycyrrhizin-ammonium salt, glycine, and orange powder; preservatives such as sodium benzoate, sodium hydrogen sulfite, methylparaben, and propylparaben; stabilizers such as citric acid, sodium citrate, and acetic acid; suspending agents such as methylcellulose, polyvinylpyrrolidone, and aluminum stearate; dispersing agents such as surfactants; diluents such as water, physiological saline, and orange juice; base waxes such as cacao butter, polyethylene glycol, and kerosene; and the like can be mentioned, but these are not limitative.

Preparations suitable for oral administration are a solution prepared by dissolving an effective amount of ligand in a diluent such as water, physiological saline, or orange juice; capsules, sachets or tablets comprising an effective amount of ligand in solid or granular form; a suspension prepared by suspending an effective amount of active ingredient in an appropriate dispersant; an emulsion prepared by dispersing and emulsifying a solution of an effective amount of active ingredient in an appropriate dispersant, and the like.

The medicament of the present invention can be coated by a method known per se for the purpose of taste masking, enteric dissolution, sustained release and the like as necessary. As examples of coating agents used for the coating, hydroxypropylmethylcellulose, ethylcellulose, hydroxymethylcellulose, hydroxypropylcellulose, polyoxyethylene glycol, Tween 80, Pluronic F68, cellulose acetate phthalate, hydroxypropylmethylcellulose phthalate, hydroxymethylcellulose acetate succinate, Eudragit (manufactured by Rohm, Germany, methacrylic acid/acrylic acid copolymer), dyes (e.g., red iron oxide, titanium dioxide and the like) and the like are used. The medicament may be a rapid-release preparation or sustained-release preparation. Examples of the base of the sustained-release preparation include liposome, atelocollagen, gelatin, hydroxyapatite, PLGA and the like.

As preparations suitable for parenteral administration (e.g., intravenous administration, subcutaneous administration, intramuscular administration, topical administration, intraperitoneal administration, intranasal administration, pulmonary administration and the like), aqueous and nonaqueous isotonic sterile injectable liquids are available, which may comprise an antioxidant, a buffer solution, a bacteriostatic agent, an isotonizing agent and the like. Aqueous and non-aqueous sterile suspensions can also be mentioned, which may comprise a suspending agent, a solubilizer, a thickener, a stabilizer, an antiseptic and the like. The preparation can be included in a container such as an ampoule or a vial in a unit dosage volume or in several divided doses. An active ingredient and a pharmaceutically acceptable carrier can also be freeze-dried and stored in a state that may be dissolved or suspended in an appropriate sterile vehicle just before use. In addition to liquid injections, inhalants and ointments are also acceptable. In the case of an inhalant, an active ingredient in a freeze-dried state is micronized and administered by inhalation using an appropriate inhalation device. An inhalant can be formulated as appropriate with a conventionally used surfactant, oil, seasoning, cyclodextrin or derivative thereof and the like as required.

Here, as examples of the surfactant, oleic acid, lecithin, diethylene glycol dioleate, tetrahydroflufuryl oleate, ethyl oleate, isopropyl myristate, glyceryl trioleate, glyceryl monolaurate, glyceryl monooleate, glyceryl monostearate, glyceryl monolysinoate, cetyl alcohol, stearyl alcohol, polyethyleneglycol 400, cetylpyridinium chloride, sorbitan trioleate (trade name, Span 85), sorbitan monooleate (trade name, Span 80), sorbitan monolaurate (trade name, Span 20), polyoxyethylene hydrogenated castor oil (trade name, HCO-60), polyoxyethylene (20) sorbitan monolaurate (trade name, Tween 20), polyoxyethylene (20) sorbitan monooleate (trade name, Tween 80), lecithin of natural resource origin (trade name, Epiclon), oleylpolyoxyethylene (2) ether (trade name, Brij 92), stearyl polyoxyethylene (2) ether (trade name, Brij 72), lauryl polyoxyethylene (4) ether (trade name, Brij 30), oleylpolyoxyethylene (2) ether (trade name, Genapol 0-020), block copolymer of oxyethylene and oxypropylene (trade name, Synperonic) and the like can be mentioned. Span, Tween, Epiclon, Brij, Genapol and Synperonic are trade marks.

As examples of the oil, corn oil, olive oil, cottonseed oil, sunflower oil and the like can be mentioned. In the case of an ointment, an appropriate pharmaceutically acceptable base (yellow petrolatum, white petrolatum, paraffin, plastibase, silicone, white ointment, beeswax, lard, vegetable oils, hydrophilic ointment, hydrophilic petrolatum, purified lanolin, hydrous lanolin, water-absorbing ointment, hydrophilic plastibase, macrogol ointment and the like) is blended with an active ingredient, and used as a preparation.

An inhalant can be produced according to a conventional method. Specifically, an inhalant can be produced by powdering or liquefying the above-described aptamer or complex of the present invention, blending it in an inhalation propellant and/or carrier, and filling them in an appropriate inhalation vessel. When the above-described aptamer or complex of the present invention is a powder, an ordinary mechanical powder inhalator can be used; in the case of a liquid, an inhalator such as a nebulizer can be used. Here, as the propellant, conventionally known one can be widely used; chlorofluorocarbon-series compounds such as chlorofluorocarbon-11, chlorofluorocarbon-12, chlorofluorocarbon-21, chlorofluorocarbon-22, chlorofluorocarbon-113, chlorofluorocarbon-114, chlorofluorocarbon-123, chlorofluorocarbon-142c, chlorofluorocarbon-134a, chlorofluorocarbon-227, chlorofluorocarbon-C318, and 1,1,1,2-tetrafluoroethane, hydrocarbons such as propane, isobutane, and n-butane, ethers such as diethyl ether, compressed gases such as nitrogen gas and carbon dioxide gas and the like can be mentioned.

When the medicament of the present invention is used as a medicament for the prophylaxis or treatment of cartilage diseases, the medicament of the present invention can be directly administered to an articular inflammatory site, or administered according to the above-mentioned other methods.

Since the aptamer of the present invention is a single strand nucleic acid, detoxification by the administration of a nucleotide containing a complementary sequence is possible, and has a high possibility of making a pharmaceutical product with higher safety than a neutralizing antibody which is difficult to control dynamically after administration. This is an extremely advantageous aspect in view of the problem of infections possibly occurring in the antibody in the drug treatment and the like, which is caused by a long retention time of antibody in the body. Particularly, when the medicament of the present invention is used as a medicament for the prophylaxis or treatment of arthritis, it is obvious, in consideration of the severity of disease and the risk of side effects, that a medicament having higher safety can be obtained by utilizing an aptamer permitting easy control of in vivo kinetics.

The dosage of the medicament of the present invention varies depending on the kind and activity of active ingredient, seriousness of disease, animal species being the subject of administration, drug tolerability of the subject of administration, body weight, age and the like, and the usual dosage, based on the amount of active ingredient per day for an adult, can be about 0.0001 to about 100 mg/kg, for example, about 0.0001 to about 10 mg/kg, preferably about 0.005 to about 1 mg/kg.

The aptamer or complex of the present invention can also be used as a drug delivery vehicle, a probe for in vivo imaging, a probe for determination of blood concentrations of ADAMTS5, a probe for histological staining, a probe for ELISA, and a ligand for separation and purification of ADAMTS5.

The present invention also provides a solid phase carrier having the aptamer and the complex of the present invention immobilized thereon. As examples of the solid phase carrier, a substrate, a resin, a plate (e.g., multiwell plate), a filter, a cartridge, a column, and a porous material can be mentioned. The substrate can be one used in DNA chips, protein chips and the like; for example, nickel-PTFE (polytetrafluoroethylene) substrates, glass substrates, apatite substrates, silicon substrates, alumina substrates and the like, and substrates prepared by coating these substrates with a polymer and the like can be mentioned. As examples of the resin, agarose particles, silica particles, a copolymer of acrylamide and N,N'-methylenebisacrylamide, polystyrene-crosslinked divinylbenzene particles, particles of dextran crosslinked with epichlorohydrin, cellulose fiber, crosslinked polymers of aryldextran and N,N'-methylenebisacrylamide, monodispersed synthetic polymers, monodispersed hydrophilic polymers, Sepharose, Toyopearl and the like can be mentioned, and also resins prepared by binding various functional groups to these resins were included. The solid phase carrier of the present invention can be useful in, for example, purifying, detecting and quantifying ADAMTS5.

The aptamer and the complex of the present invention can be immobilized onto a solid phase carrier by a method known per se. For example, a method that introduces an affinity substance (e.g., those described above) or a predetermined functional group into the aptamer or the complex of the present invention, and then immobilizes the aptamer and complex onto a solid phase carrier via the affinity substance or predetermined functional group can be mentioned. The present invention also provides a method for immobilizing the aptamer or complex of the present invention on a solid phase carrier, and a solid phase carrier obtained thereby. The predetermined functional group can be a functional group that can be subjected to a coupling reaction; for example, an amino group, a thiol group, a hydroxy group, and a carboxyl group can be mentioned. The present invention also provides an aptamer having such a functional group introduced thereinto.

The present invention also provides a method for purifying and concentrating ADAMTS5. In particular, the purification method of the present invention makes it possible to separate ADAMTS5 from other ADAMTS family proteins. The method of purification and concentration of the present invention can comprise adsorbing ADAMTS5 to the solid phase carrier of the present invention, and eluting the adsorbed ADAMTS5 with an eluent. Adsorption of ADAMTS5 to the solid phase carrier of the present invention can be achieved by a method known per se. For example, an ADAMTS5-containing sample (e.g., bacterial or cell culture or culture supernatant, blood) is introduced into the solid phase carrier of the present invention or a composition containing the same. ADAMTS5 can be eluted using an eluent such as a neutral solution. There is no limitation on the neutral eluent, which can have a pH of, for example, about 6 to about 9, preferably about 6.5 to about 8.5, and more preferably about 7 to about 8. The neutral solution can also contain, for example, a potassium salt (e.g., KCl), a magnesium salt (e.g., $MgCl_2$), a surfactant (e.g., Tween 20, Triton, NP40), and glycerin.

The method of purification and concentration of the present invention can further comprise washing the solid phase carrier using a washing solution after ADAMTS5 adsorption. Examples of the washing solution include those containing urea, a chelating agent (e.g., EDTA), Tris, an acid, an alkali, Transfer RNA, DNA, surfactants such as Tween 20, salts such as NaCl and the like. The method of purification and concentration of the present invention can still further comprise heating the solid phase carrier. This step enables the regeneration and sterilization of the solid phase carrier.

The aptamer or complex of the present invention can be utilized as a detection probe, particularly as a probe for detection of ADAMTS5. The method for labeling the aptamer is not particularly limited; methods known per se can be applied. Such methods include, for example, labeling with a radioisotope, labeling with a fluorescent dye or fluorescent protein, and the like.

The present invention also provides a method for detecting and quantifying ADAMTS5. In particular, the present invention makes it possible to detect and quantify ADAMTS5 separately from the proteins of other ADAMTS family proteins. The method of detection and quantitation of the present invention can comprise measuring ADAMTS5 by utilizing the aptamer of the present invention (e.g., by the use of the complex and solid phase carrier of the present invention). The method for detecting and quantifying ADAMTS5 can be performed in the same manner as an immunological method, except that the aptamer of the present invention is used in place of an antibody. Therefore, by using the aptamer of the present invention in place of an antibody, in the same manner as such methods as enzyme immunoassay (EIA) (e.g., direct competitive ELISA, indirect competitive ELISA, sandwich ELISA), radioimmunoassay (RIA), fluorescent immunoassay (FIA), Western blot method (e.g., use instead of secondary antibody in Western blot method), immunohistochemical staining method, and cell sorting method, detection and quantitation can be performed. These methods can be useful in, for example, measuring ADAMTS5 contents in living organisms or biological samples, and in diagnosing a disease associated with ADAMTS5.

The disclosures in all publications mentioned herein, including patents and patent application specifications, are incorporated by reference herein in the present invention to the extent that all of them have been given expressly.

The following shows examples of particular embodiments to practice the present invention. The Examples are provided for illustrative purposes only, and do not intend to limit the scope of the present invention in any way.

EXAMPLE

Example 1: Preparation of RNA Aptamer Specifically Binding to ADAMTS5 (1)

An RNA aptamer that specifically binds to ADAMTS5 was prepared using the SELEX method. SELEX was performed by reference to the method of Ellington et al. (Ellington and Szostak, Nature 346, 818-822, 1990) and the method of Tuerk et al. (Tuerk and Gold, Science 249, 505-510, 1990). As the target substance, ADAMTS5 (manufactured by R&D systems) immobilized on a carrier of NHS-activated Sepharose 4 Fast Flow (manufactured by GE healthcare) was used. The immobilization method of ADAMTS5 onto the carrier was performed according to the manual of GE healthcare. The amount of immobilization was confirmed by examining the ADAMTS5 solution before immobilization and the supernatant immediately after immobilization by SDS-PAGE. As a result of SDS-PAGE, ADAMTS5 band was not detected from the supernatant, which confirmed that almost all ADAMTS5 used was coupled. About 73.2 pmol of ADAMTS5 was immobilized on about 3 μL of resin.

The RNA used in the first round (40N) was obtained by transcribing a chemically synthesized DNA using the DuraScribe™ T7 Transcription Kit (manufactured by Epicentre). In the RNA obtained by this method, the 2'-position of the ribose of the pyrimidine nucleotide was fluorinated. A 80 nucleotide long DNA shown below, having a primer sequence at each end of a 40-nucleotide random sequence, was used as a DNA template. The DNA template and the primers were prepared by chemical synthesis.

```
DNA template:
                                          (SEQ ID NO: 46)
5'-GTACGCTAGGCGTTAGTCTCNNNNNNNNNNNNNNNNNNNNNNNNNNNNNN
NNNNNNNNNNNNNNNNATCGTACGACGGTCGTACCC-3' primer Fwd:
                                          (SEQ ID NO: 47)
5'-TAATACGACTCACTATAGGGTACGACCGTCGTACGAT-3' primer Rev:
                                          (SEQ ID NO: 48)
5'-GTACGCTAGGCGTTAGTCTC-3'
```

The continuous Ns in the DNA template (SEQ ID NO: 46) are any combination of 40 nucleotides (40N: each N is A, C, G or T), and form a sequence region distinct to the obtained aptamer. The primer Fwd comprises a promoter sequence of T7 RNA polymerase. The variation of the RNA pool used in the first round was theoretically $10^{13}$.

The RNA pool was added to the carrier on which ADAMTS5 was immobilized, and the mixture was maintained at room temperature for 30 min. The resin was washed with solution A to remove RNA not bound to ADAMTS5. Here, solution A is a mixed solution of 145 mM sodium chloride, 5.4 mM potassium chloride, 1.8 mM calcium chloride, 0.8 mM magnesium chloride, 20 mM tris (pH 7.6), 0.05% Tween 20. The RNA bound to ADAMTS5 was obtained by adding solution B as an eluate, heat treating the mixture at 95° C. for 3 min and recovering from the supernatant thereof. Here, solution B is a mixed solution of 7 M Urea, 5 mM EDTA, 20 mM tris (pH 7.6). The recovered RNA was amplified by reverse transcription PCR and the amplified DNA was transcribed using DuraScribe™ T7 Transcription Kit to prepare an RNA pool for the next round. With the above as 1 round, a similar operation was repeated plural times. After completion of SELEX, the nucleotide sequence was analyzed using a next generation sequencer. As the next generation sequencer, Ion PGM™ system (manufactured by Thermo) was used and the analysis was performed according to the manual of Thermo.

After 7 rounds of SELEX, 78889 kinds of clone sequences were determined by the next generation sequencer, and they were confirmed to converge to 10068 kinds of sequence. Some sequences of those clones are shown in SEQ ID NOs: 1-2. There existed 6,711 sequences shown in SEQ ID NO: 1. There existed 1,305 sequences shown in SEQ ID NO: 2. The sequences shown in SEQ ID NO: 1 contained consensus sequence 1. SEQ ID NOs: 1 and 2 are different only in one base in the sequences, and one of the 4 continuous G bases in the consensus sequence was deleted in SEQ ID NO: 2. There were 138 kinds of sequences having consensus sequence 1 among the 10,068 kinds of sequences. The secondary structures of these sequences were predicted by the MFOLD program (M. Zuker, Nucleic Acids Res. 31(13), 3406-3415, 2003). As a result, the consensus sequence portion had a similar loop structure. The secondary structure of an aptamer having the nucleotide sequence shown in SEQ ID NO: 1 is presented in FIG. 1.

Respective nucleotide sequences are shown below. Unless particularly indicated, the sequences shown below are in the 5' to 3' direction, purine bases (A and G) are 2'-OH compounds and pyrimidine bases (U and C) are 2'-fluoro modified compounds. $N_1$ in the sequences shows 3-24 nucleotides with any length, and Y is C or U.

```
SEQ ID NO: 1:
GGGUACGACCGUCGUACGAUUGGGGCCUCCACAGCUGCUCAGCUUGGAC
UAAACCAAUAAGAGACUAACGCCUAGCGUAC

SEQ ID NO: 2:
GGGUACGACCGUCGUACGAUUGGGCCUCCACAGCUGCUCAGCUUGGACU
AAACCAAUAAGAGACUAACGCCUAGCGUAC consensus sequence 1
                                          (SEQ ID NO: 55)
GGGGCCUCC-N₁-GGACYAAAC
```

The binding activity of aptamers having the nucleotide sequences shown in SEQ ID NOs: 1 and 2 to ADAMTS5 was evaluated by the surface plasmon resonance method. Biacore T100 manufactured by GE Healthcare was used for the measurement. The SA chip was used as the sensor chip, which had streptavidin immobilized thereon. About 800 RU of a 16-nucleotide Poly dT with biotin at the 5'-terminal was bound on the chip. The ligand nucleic acid had a 16-nucleotide Poly A at the 3'-terminal thereof, and was immobilized on the SA chip by annealing of T and A. The nucleic acids were injected at a flow rate of 10 μL/min for 30 sec to immobilize about 300 RU of the nucleic acids. ADAMTS5 for analyte was prepared at 0.1 μM, and injected at a flow rate of 30 μL/min for 60 sec. As the running buffer, solution C was used. The solution C is a mixed solution of 300 mM sodium chloride, 5.4 mM potassium chloride, 1.8 mM calcium chloride, 0.8 mM magnesium chloride, 20 mM tris (pH 7.6), and 0.05% Tween20.

As a result of the measurement, it was found that an aptamer having the nucleotide sequence shown in SEQ ID NO: 1 binds to ADAMTS5 (Table 1). The nucleic acid pool (40N) used as a negative control for the first round and containing a 40-nucleotide random sequence did not bind to ADAMTS5. The aptamer having the nucleotide sequence shown in SEQ ID NO: 2 did not bind to ADAMTS5, and was of the same level as 40N. SEQ ID NO: 2 has a sequence with one base deletion from the continuous 4 G bases in the consensus sequence, and it was shown from the measurement results of the binding activity that the continuous 4 G bases in the consensus sequence are important for the activity of aptamers. Sensorgram showing the binding of an aptamer having the nucleotide sequence shown in SEQ ID NO: 1 to ADAMTS5 is presented in FIG. 2. In Table 1, "++" indicates those with the proportion of ADAMTS5 binding amount (RU value) to the amount of aptamer immobilized on the SA chip (RU value) of not less than 40%, "+" indicates those with the proportion of not less than 10% and less than 40%, and "−" indicates those with the proportion of less than 10%.

TABLE 1

| | binding activity to ADAMTS5 | |
|---|---|---|
| SEQ ID NO: | length | binding activity by Biacore |
| 1 | 80 | ++ |
| 2 | 79 | − |

Whether an aptamer having the nucleotide sequence shown in SEQ ID NO: 1 inhibits the enzyme activity of ADAMTS5 was evaluated by the following method. As a substrate of ADAMTS5, the G1-IGD-G2 domain of aggrecan (manufactured by R&D systems) was used. ADAMTS5 specifically cleaves in between the 392nd glutamic acid and the 393rd alanine in the G1-IGD-G2 domain and produces two fragments. These fragments have faster electrophoretic mobility than uncleaved G1-IGD-G2. Thus, the enzyme activity of ADAMTS5 can be measured by quantifying the band intensity of G1-IGD-G2 by SDS-PAGE electrophoresis. The assay was performed in a solution A buffer with a reaction mixture volume of 10 μL. First, a mixture (10 μL) of a nucleic acid and ADAMTS5 was prepared and incubated at 25° C. for 15 min. To a substrate solution (5 μL) diluted with solution A was added a mixture (5 μL) of the nucleic acid and ADAMTS5 to start the enzyme reaction. The final concentration of ADAMTS5 in the reaction solution was 5 nM, and the final substrate concentration was 50 μg/mL. The reaction solution was incubated at 37° C. for 2 hr, 2 μL of solution D was added, and the mixture was heated at 95° C. for 2 min to stop the enzyme reaction of ADAMTS5. Solution D contains 0.25 M tris (pH 6.8), 10% SDS, 50% glycerol, 0.25% bromo phenolblue, and 20% 2-mercaptoethanol. The heat-treated reaction solution was electrophoresed by 7.5% SDS-PAGE and stained with SYPRO Orange (manufactured by Sigma-Aldrich). The staining was performed according to the manual of Sigma-Aldrich and detected using STORM840 manufactured by GE Healthcare. For analytical curves, uncleaved substrates 1000 ng, 400 ng, 160 ng, 64 ng, 25.6 ng, 10.24 ng, and 4.1 ng were electrophoresed, and staining and detection were performed in the same manner. The amount of uncleaved substrate in each reaction solution was quantified from the band intensity and the standard curve. The substrate cleavage efficiency of ADAMTS5 under these reaction conditions was 80-100%. The inhibition rate of the test substance was calculated using the following equation.

inhibition rate (%)=$(S_{apt}-S_E)/(S_0-S_E) \times 100$ wherein $S_{apt}$ is the amount of an uncleaved substrate with the addition of a test substance, $S_E$ is the residual amount of an uncleaved substrate with the addition of ADAMTS5, and $S_0$ is the residual amount of an uncleaved substrate without the addition of ADAMTS5.

The concentration of an inhibitor necessary for inhibiting 50% of the enzyme activity ($IC_{50}$) was determined. The results thereof are shown in Table 2. $IC_{50}$ is a mean of four measurements.

TABLE 2

| inhibitory activity against ADAMTS5 ($IC_{50}$) | |
|---|---|
| SEQ ID NO: | $IC_{50}$ [nM] |
| 1 | 16.8 ± 2.8 |

The negative control 40N did not show an inhibitory activity under the condition of final nucleic acid concentration of 30 nM (inhibition rate 5.6±4.7%). The $IC_{50}$ value of the positive control, ADAMTS5 low-molecular-weight inhibitor (CAS929634-33-3) (manufactured by Merck), was 90.5 μM.

From the above results, it suggests that an aptamer having the nucleotide sequence shown in SEQ ID NO: 1 shows a superior inhibitory effect on ADAMTS5.

Example 2: Strand-Shortening of Aptamer-1

Figure 3:
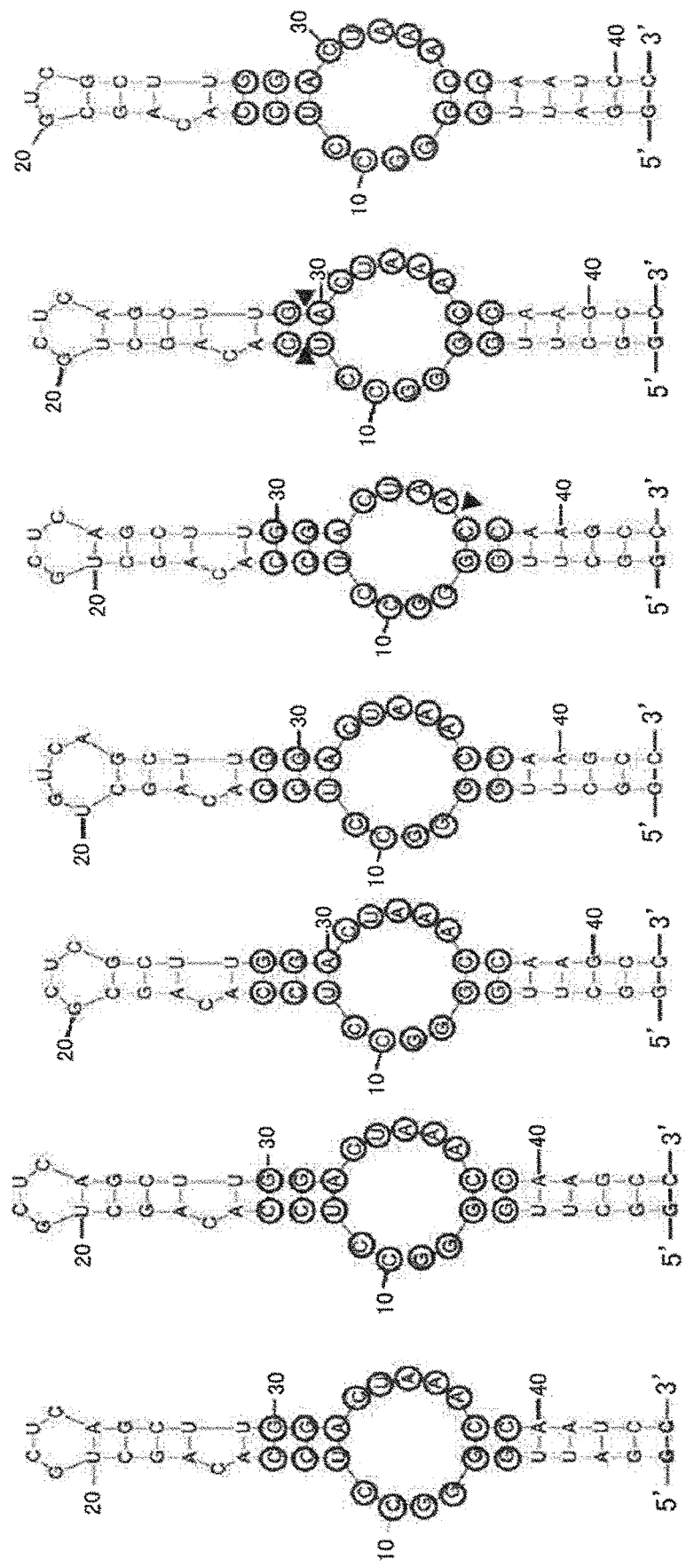
FIG. 3 shows the secondary structure of an aptamer having the nucleotide sequence shown in SEQ ID NOs: 3 to 9 as predicted from the MFOLD program.

An aptamer having the nucleotide sequence shown in SEQ ID NO: 1 was strand-shortened. The sequences after strand-shortening are shown in SEQ ID NOs: 3-9. The predicted secondary structures of the aptamers shown in SEQ ID NOs: 3-9 are presented in FIG. 3. In FIG. 3, the consensus sequences are enclosed with a circle (◯). For the sequence with a partially deleted consensus sequence, the deleted positions are indicated by an arrow (black triangle).

The nucleotide sequences of the aptamers shown in the following SEQ ID NOs: 3-9 are shown below. Unless particularly indicated, each sequence shown below is in the 5' to 3' direction, the purine bases (A and G) are 2'-OH compounds, and the pyrimidine bases (U and C) are 2'-fluoro modified compounds.

SEQ ID NO: 3:
(sequence obtained by shortening the sequence shown in SEQ ID NO: 1 to a length of 44 nucleotides including the consensus sequence)

GGAUUGGGGCCUCCACAGCUGCUCAGCUUGGACUAAACCAAUCC

SEQ ID NO: 4:
(sequence obtained by shortening the sequence shown in SEQ ID NO: 1 to a length of 44 nucleotides including the consensus sequence and further substituting AU base pairs consisting of 3rd and 42nd with CG base pairs)

GGCUUGGGGCCUCCACAGCUGCUCAGCUUGGACUAAACCAAGCC

SEQ ID NO: 5:
(sequence obtained by shortening the sequence shown in SEQ ID NO: 4 to a length of 42 nucleotides including the consensus sequence)

GGCUUGGGGCCUCCACAGCGCUCGCUUGGACUAAACCAAGCC

SEQ ID NO: 6:
(sequence obtained by shortening the sequence shown in SEQ ID NO: 4 to a length of 43 nucleotides including the consensus sequence)

GGCUUGGGGCCUCCACAGCUGUCAGCUUGGACUAAACCAAGCC

SEQ ID NO: 7:
(sequence consisting of 43 nucleotides obtained by deleting one of the three continuous A bases of the consensus sequence in the sequence shown in SEQ ID NO: 4)

GGCUUGGGGCCUCCACAGOUGCUCAGCUUGGACUAACCAAGCC

SEQ ID NO: 8:
(sequence consisting of 42 nucleotides obtained by deleting CG base pairs (13th and 31st bases) of the consensus sequence in the sequence shown in SEQ ID NO: 4)

GGCUUGGGGCCUCACAGCUGCUCAGCUUGACUAAACCAAGCC

SEQ ID NO: 9:
(sequence obtained by shortening a combination of the sequences shown in SEQ ID NOs: 3, 5, 6 to a length of 41 nucleotides including the consensus sequence)

GGAUUGGGGCCUCCACAGCGUCGCUUGGACUAAACCAAUCC

Whether these aptamers inhibit the enzyme activity of ADAMTS5 was tested by a method similar to that in Example 1. The final concentration of the nucleic acid was fixed to 30 nM in the test. The results thereof are shown in Table 3.

TABLE 3

| | inhibitory activity against ADAMTS5 | |
|---|---|---|
| SEQ ID NO: | length | % inhibitory activity |
| 3 | 44 | 36.4 |
| 4 | 44 | 23 |
| 5 | 42 | 27 |
| 6 | 43 | 33.7 |
| 7 | 43 | −2.3 |
| 8 | 42 | −8.6 |
| 9 | 41 | 5.9 |

It was found from the results of the aptamers having the nucleotide sequences shown in SEQ ID NOs: 3 and 4 that AU base pair consisting of the 3rd and the 42nd also functions with CG base pair. It was found from the results of the aptamers having the nucleotide sequences shown in SEQ ID NOs: 5, 6, 9 that the activity is not influenced by strand-shortening the stem region of $N_1$ (stem-loop structure) in the consensus sequence to 9 bases and the loop region to 3 bases, but these in combination remarkably influences the activity. From the above results, it is shown that $N_1$ in the consensus sequence can be strand-shortened to at least 13 bases.

Example 3: Alteration of Aptamer-1

To enhance the nuclease resistance of an aptamer having the nucleotide sequence shown in SEQ ID NO: 3 (2′-position of ribose of pyrimidine nucleotide is fluorinated), variants incorporating a 2′-O-methyl group were produced. The modified sequences are shown in SEQ ID NOs: 3(1)-3(16).

The nucleotide sequences of the aptamers having the nucleotide sequences shown in SEQ ID NOs: 3(1)-3(16) are shown below together with the modifications. Unless particularly indicated, the sequences shown below are in the 5′ to 3′ direction, and capital letters indicate RNA. The parentheses in the nucleotides indicate the modification of the 2′-position of ribose, F is a fluorine atom, and M is an O-methyl group.

SEQ ID NO: 3(1):
(sequence obtained by introducing 2′-O-methyl modification into 6 positions of the sequence other than the consensus sequence of the sequence shown in SEQ ID NO: 3)

G(M)G(M)A(M)U(F)U(F)GGGGC(F)C(F)U(F)C(F)C(F)AC(F)AGC(F)U(F)GC(F)U(F)C(F)AGC(F)U(F)U(F)GGAC(F)U(F)AAAC(F)C(F)AAU(M)C(M)C(M)

SEQ ID NO: 3(2):
(sequence obtained by introducing 2′-O-methyl modification into 6 positions of the sequence containing the consensus sequence of the sequence shown in SEQ ID NO: 3)

GGAU(M)U(M)G(M)GGGC(F)C(F)U(F)C(F)C(F)AC(F)AGC(F)U(F)GC(F)U(F)C(F)AGC(F)U(F)U(F)GGAC(F)U(F)AAAC(F)C(M)A(M)A(M)U(F)C(F)C(F)

SEQ ID NO: 3(3):
(sequence obtained by introducing 2′-O-methyl modification into 6 positions of the sequence other than the consensus sequence of the sequence shown in SEQ ID NO: 3)

GGAU(F)U(F)GGGGC(F)C(F)U(F)C(F)C(F)AC(F)AG(M)C(M)U(M)GC(F)U(F)C(F)A(M)G(M)C(M)U(F)U(F)GGAC(F)U(F)AAAC(F)C(F)AAU(F)C(F)C(F)

SEQ ID NO: 3(4):
(sequence obtained by introducing 2′-O-methyl modification into one position of the consensus sequence of the sequence shown in SEQ ID NO: 3)

GGAU(F)U(F)GGGGC(F)C(F)U(F)C(F)C(F)AC(F)AGC(F)U(F)GC(F)U(F)C(F)AGC(F)U(F)U(F)GGAC(F)U(F)AA(M)AC(F)C(F)AAU(F)C(F)C(F)

SEQ ID NO: 3(5):
(sequence obtained by introducing a combination of all 2′-O-methyl modifications of the sequences shown in SEQ ID NOs: 3(1)-3(4))

G(M)G(M)A(M)U(M)U(M)G(M)GGGC(F)C(F)U(F)C(F)C(F)AC(F)AG(M)C(M)U(M)GC(F)U(F)C(F)A(M)G(M)C(M)U(F)U(F)GGAC(F)U(F)AA(M)AC(F)C(M)A(M)A(M)U(M)C(M)C(M)

SEQ ID NO: 3(6):
(sequence obtained by applying 2′-O-methyl modification to 2 positions of the consensus sequence of the sequence shown in SEQ ID NO: 3(5))

G(M)G(M)A(M)U(M)U(M)G(M)G(M)GGC(F)C(F)U(F)C(F)C(F)AC(F)AG(M)C(M)U(M)GC(F)U(F)C(F)A(M)G(M)C(M)U(F)U(F)(F)GGAC(F)U(F)AA(M)AC(F)C(M)A(M)A(M)U(M)C(M)C(M)

SEQ ID NO: 3(7):
(sequence obtained by applying 2′-O-methyl modification to one position of the sequence other than the consensus sequence of the sequence shown in SEQ ID NO: 3(5))

G(M)G(M)A(M)U(M)U(M)G(M)GGGC(F)C(F)U(F)C(F)C(F)AC(M)AG(M)C(M)U(M)GC(F)U(F)C(F)A(M)G(M)C(M)U(F)U(F)GGAC(F)U(F)AA(M)AC(F)C(M)A(M)A(M)U(M)C(M)C(M)

SEQ ID NO: 3(8):
(sequence obtained by introducing 2′-O-methyl modification into 6 positions of the sequence other than the consensus sequence of the sequence shown in SEQ ID NO: 3(5))

G(M)G(M)A(M)U(M)U(M)G(M)G(M)GGC(F)C(F)U(F)C(F)C(F)AC(F)A(M)G(M)C(M)U(M)G(M)C(M)U(M)C(M)A(M)G(M)C(M)U(M)U(F)GGAC(F)U(F)AA(M)AC(M)C(M)A(M)A(M)U(M)C(M)C(M)

SEQ ID NO: 3(9):
(sequence obtained by applying 2′-O-methyl modification to one position of the consensus sequence of the sequence shown in SEQ ID NO: 3(8))

G(M)G(M)A(M)U(M)U(M)G(M)G(M)G(M)GC(F)C(F)U(F)C(F)C(F)AC(F)A(M)G(M)C(M)U(M)G(M)C(M)U(M)C(M)A(M)G(M)C(M)U(M)U(F)GGAC(F)U(F)AA(M)AC(M)C(M)A(M)A(M)U(M)C(M)C(M)

SEQ ID NO: 3(10):
(sequence obtained by applying 2′-O-methyl modification to one position of the consensus sequence of the sequence shown in SEQ ID NO: 3(8))

G(M)G(M)A(M)U(M)U(M)G(M)G(M)G(M)GG(M)C(F)C(F)U(F)C(F)C(F)AC(F)A(M)G(M)C(M)U(M)G(M)C(M))U(M)C(M)A(M)G(M)C(M)

-continued (M)U(M)U(F)GGAC(F)U(F)AA(M)AC(M)C(M)A(M)A(M)U(M)C
(M)C(M)

SEQ ID NO: 3(11):
(sequence obtained by applying 2'-O-methyl modification to one position of the sequence other than the consensus sequence of the sequence shown in SEQ ID NO: 3(8))

G(M)G(M)A(M)U(M)U(M)G(M)G(M)GGC(F)C(F)U(F)C(F)C(F)
A(M)C(F)A(M)G(M)C(M)U(M)G(M)C(M)U(M)C(M)A(M)G(M)C
(M)U(M)U(F)GGAC(F)U(F)AA(M)AC(M)C(M)A(M)A(M)U(M)C
(M)C(M)

SEQ ID NO: 3(12):
(sequence obtained by applying 2'-O-methyl modification to one position of the consensus sequence of the sequence shown in SEQ ID NO: 3(8))

G(M)G(M)A(M)U(M)U(M)G(M)G(M)GGC(F)C(F)U(F)C(F)C(F)
AC(F)A(M)G(M)C(M)U(M)G(M)C(M)U(M)C(M)A(M)G(M)C(M)U
(M)U(F)G(M)GAC(F)U(F)AA(M)AC(M)C(M)A(M)A(M)U(M)C
(M)C(M)

SEQ ID NO: 3(13):
(sequence obtained by applying 2'-O-methyl modification to one position of the consensus sequence of the sequence shown in SEQ ID NO: 3(8))

G(M)G(M)A(M)U(M)U(M)G(M)G(M)GGC(F)C(F)U(F)C(F)C(F)
AC(F)A(M)G(M)C(M)U(M)G(M)C(M)U(M)C(M)A(M)G(M)C(M)U
(M)U(F)GG(M)AC(F)U(F)AA(M)AC(M)C(M)A(M)A(M)U(M)C
(M)C(M)

SEQ ID NO: 3(14):
(sequence obtained by applying 2'-O-methyl modification to one position of the consensus sequence of the sequence shown in SEQ ID NO: 3(8))

G(M)G(M)A(M)U(M)U(M)G(M)G(M)GGC(F)C(F)U(F)C(F)C(F)
AC(F)A(M)G(M)C(M)U(M)G(M)C(M)U(M)C(M)A(M)G(M)C(M)U
(M)U(F)GGA(M)C(F)U(F)AA(M)AC(M)C(M)A(M)A(M)U(M)C
(M)C(M)

SEQ ID NO: 3(15):
(sequence obtained by applying 2'-O-methyl modification to one position of the consensus sequence of the sequence shown in SEQ ID NO: 3(8))

G(M)G(M)A(M)U(M)U(M)G(M)G(M)GGC(F)C(F)U(F)C(F)C(F)
AC(F)A(M)G(M)C(M)U(M)G(M)C(M)U(M)C(M)A(M)G(M)C(M)U
(M)U(F)GGAC(F)U(F)A(M)A(M)AC(M)C(M)A(M)A(M)U(M)C
(M)C(M)

SEQ ID NO: 3(16):
(sequence obtained by applying 2'-O-methyl modification to one position of the consensus sequence of the sequence shown in SEQ ID NO: 3(8))

G(M)G(M)A(M)U(M)U(M)G(M)G(M)GGC(F)C(F)U(F)C(F)C(F)
AC(F)A(M)G(M)C(M)U(M)G(M)C(M)U(M)C(M)A(M)G(M)C(M)U
(M)U(F)GGAC(F)U(F)AA(M)A(M)C(M)C(M)A(M)A(M)U(M)C
(M)C(M)

The nucleic acids shown in SEQ ID NOs: 3(1)-3(16) were all produced by chemical synthesis. Whether these nucleic acids inhibit the enzyme activity of ADAMTS5 was determined by a method similar to that in Example 1. The final concentrations of the nucleic acids in the evaluation were 10 nM and 30 nM. The results are shown in Table 4. In the Table, "n.d." means not determined.

TABLE 4

Inhibitory activity against ADAMTS5

| | nucleic acid concentration | |
|---|---|---|
| SEQ ID NO: | 30 nM | 10 nM |
| 3 | 58.4 | 33.9 |
| 3(1) | 49.8 | n.d. |
| 3(2) | 53.6 | n.d. |
| 3(3) | 48.6 | n.d. |
| 3(4) | 53.1 | n.d. |
| 3(5) | 75 | 41.7 |
| 3(6) | 82.6 | 46.9 |
| 3(7) | 59.6 | 23.9 |
| 3(8) | n.d. | 52.8 |
| 3(9) | n.d. | 25.8 |
| 3(10) | n.d. | 25.6 |
| 3(11) | n.d. | 48.1 |
| 3(12) | n.d. | 57.5 |
| 3(13) | n.d. | 37 |
| 3(14) | n.d. | 1.2 |
| 3(15) | n.d. | 27.6 |
| 3(16) | n.d. | 53.6 |

It was found that each aptamer shows an inhibitory activity, albeit with varying strength. The inhibitory activity of the aptamers having the nucleotide sequences shown in SEQ ID NOs: 3(1)-3(4) was maintained generally at the same level as in SEQ ID NO: 3, and it was shown that the inhibitory activity of the aptamer having the nucleotide sequence shown in SEQ ID NO: 3(5) containing all modifications of SEQ ID NOs: 3(1)-3(4) in combination is improved more than that of the aptamer having the nucleotide sequence shown in SEQ ID NO: 3. In addition, it was shown that the aptamers having the nucleotide sequences shown in SEQ ID NOs: 3(6) and 3(8), which are obtained by further introducing modification into SEQ ID NO: 3(5) showed further improved inhibitory activity but the aptamer having the nucleotide sequence shown in SEQ ID NO: 3(7) shows a lower inhibitory activity. It was shown that the inhibitory activity of the aptamer having the nucleotide sequence shown in SEQ ID NO: 3(11), 3(12), or 3(16), which is obtained by further introducing modification into SEQ ID NO: 3(8), was maintained, but the inhibitory activity decreased in SEQ ID NOs: 3(9), 3(10), 3(13), 3(14), 3(15).

From the above results, it was found that an aptamer having the nucleotide sequence shown in SEQ ID NO: 3 into which modification is introduced into various sites (at least 28) of nucleotides to improve stability also functions. In addition, it was found that the 5'-side 2 bases (G, G) and 3'-side 4 bases (A, A, C, C) in the consensus sequence are able to function even when the modification of 2'-O-methyl or the like is introduced. As the modification of nucleotide, for example, 2'-amino modification and the like can be mentioned besides the 2'-O-methyl modification.

Example 4: Strand-Shortening of Aptamer-2

Figure 4:
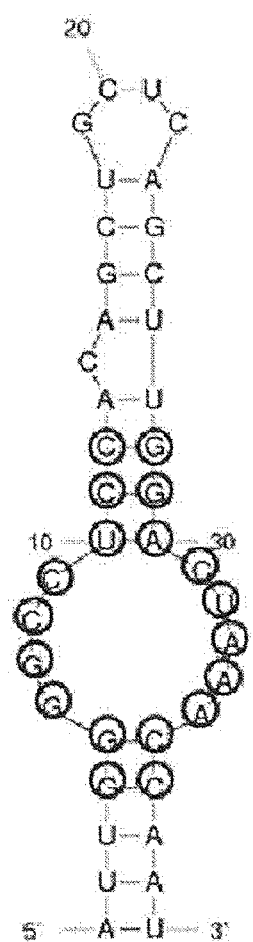
FIG. 4 shows the secondary structure of an aptamer having the nucleotide sequence shown in SEQ ID NOs: 10 to 12 as predicted from the MFOLD program.
Figure 4:
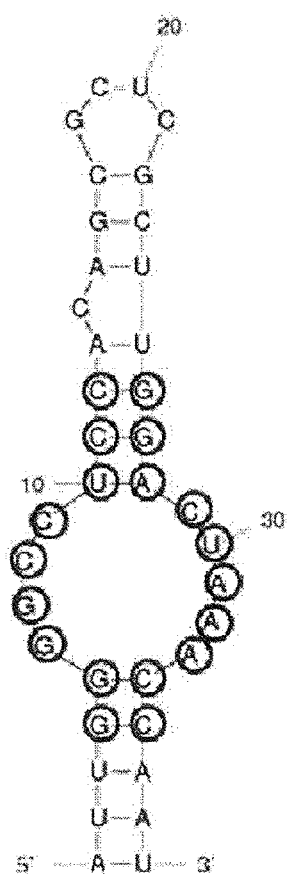
Figure 4:
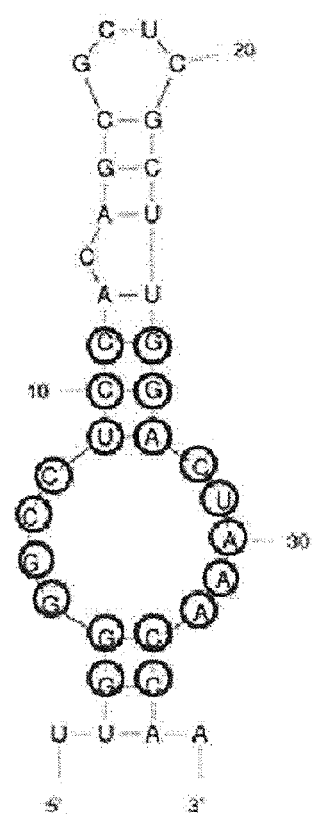

The aptamer having the nucleotide sequence shown in SEQ ID NO: 3(16) was further strand-shortened. The sequences after shorting and modification are shown in SEQ ID NOs: 10-12. The predicted secondary structures of the aptamers shown in SEQ ID NOs: 10-12 are presented in FIG. 4. In FIG. 4, the consensus sequences are enclosed with a circle (○).

The respective nucleotide sequences of the aptamers having the nucleotide sequences shown in the following SEQ ID NOs: 10-12 are presented below. Unless particularly indicated, each sequence shown below is in the 5' to 3' direction, and capital letters indicate RNA. The parentheses in the nucleotides indicate modification of the 2'-position of ribose, F is a fluorine atom, and M is an O-methyl group.

SEQ ID NO: 10:
(sequence obtained by shortening to a length of 40 nucleotides including the consensus sequence by combining 2'-O-methyl modification of the sequences shown in SEQ ID NO: 3(12) and SEQ ID NO: 3(16))

A(M)U(M)U(M)G(M)G(M)GGC(F)C(F)U(F)C(F)C(F)AC(F)A
(M)G(M)C(M)U(M)G(M)C(M)U(M)C(M)A(M)G(M)C(M)U(M)U
(F)G(M)GAC(F)U(F)AA(M)A(M)C(M)C(M)A(M)A(M)U(M)

SEQ ID NO: 11:
(sequence obtained by shortening the sequence shown in SEQ ID NO: 10 to a length of 38 nucleotides including the consensus sequence)

A(M)U(M)U(M)G(M)G(M)GGC(F)C(F)U(F)C(F)C(F)AC(F)A
(M)G(M)C(M)G(M)C(M)U(M)C(M)G(M)C(M)U(M)U(F)G(M)GAC
(F)U(F)AA(M)A(M)C(M)C(M)A(M)A(M)U(M)

SEQ ID NO: 12:
(sequence obtained by shortening the sequence shown in SEQ ID NO: 10 to a length of 36 nucleotides including the consensus sequence)

U(M)U(M)G(M)G(M)GGC(F)C(F)U(F)C(F)C(F)AC(F)A(M)G
(M)C(M)G(M)C(M)U(M)C(M)G(M)C(M)U(M)U(F)G(M)GAC(F)U
(F)AA(M)A(M)C(M)C(M)A(M)A(M)

The nucleic acids of SEQ ID NOs: 10-12 were all produced by chemical synthesis. Whether aptamers having the nucleotide sequences shown by these nucleic acids inhibit the enzyme activity of ADAMTS5 was determined by a method similar to that in Example 1. The final concentration of the nucleic acids in the evaluation was 10 nM. The results are shown in Table 5. The strand-shortened compounds of SEQ ID NOs: 10-12 all maintained the inhibitory activity.

TABLE 5

Inhibitory activity against ADAMTS5

| SEQ ID NO: | length | inhibition rate % (10 nM aptamer) |
|---|---|---|
| 3(12) | 44 | 57.5 |
| 3(16) | 44 | 53.6 |
| 10 | 40 | 65 |
| 11 | 38 | 59.8 |
| 12 | 36 | 71.1 | s From the above results, it was found that an aptamer having the nucleotide sequence shown in SEQ ID NO: 3 functions even with a length of 36 nucleotides including the consensus sequence.

Example 5: Alteration of Aptamer-2

To enhance the nuclease resistance of the aptamers having the nucleotide sequences shown in SEQ ID NOs: 10, 11 produced in Example 4, a variant with terminal modification, variant with 2'-O-methyl group introduction, a variant with DNA introduction, and a variant with phosphorothioate introduction were produced. The modified sequences are shown in SEQ ID NOs: 10(1)-10(8) (SEQ ID NO: 10 lineage), 11(1)-11(35) (SEQ ID NO: 11 lineage). To optimize the sequence, a variant in which a part of the sequence is substituted was produced. The sequences that received sequence substitution are shown in SEQ ID NOs: 13-14. As a negative control, one with random substitution of a part of the consensus sequence was produced. The sequence is shown in SEQ ID NO: 15.

The following shows respective nucleotide sequences shown in SEQ ID NO: 10(1)-10(8), 11(1)-11(35), 13-15. Unless particularly indicated, the sequences shown below are in the 5' to 3' direction, capital letters indicate RNA, and small letters indicate DNA. The parentheses in the nucleotides indicate modification of the 2'-position of ribose, F is a fluorine atom, and M is an O-methyl group. In addition, idT at the sequence terminal indicates modification with inverted-dT, and PEG indicates modification with 40 kDa branched-type polyethylene glycol. In the sequences, s indicates that the phosphoric acid group connecting nucleotides has been phosphorothioated.

SEQ ID NO: 10(1):
(sequence obtained by introducing 2'-O-methyl modification into one position of the consensus sequence of the sequence shown in SEQ ID NO: 10)

A(M)U(M)U(M)G(M)G(M)GGC(M)C(F)U(F)C(F)C(F)AC(F)A
(M)G(M)C(M)U(M)G(M)C(M)U(M)C(M)A(M)G(M)C(M)U(M)U
(F)G(M)GAC(F)U(F)AA(M)A(M)C(M)C(M)A(M)A(M)U(M)

SEQ ID NO: 10(2):
(sequence obtained by introducing 2'-O-methyl modification into one position of the consensus sequence of the sequence shown in SEQ ID NO: 10)

A(M)U(M)U(M)G(M)G(M)GGC(F)C(M)U(F)C(F)C(F)AC(F)A
(M)G(M)C(M)U(M)G(M)C(M)U(M)C(M)A(M)G(M)C(M)U(M)U
(F)G(M)GAC(F)U(F)AA(M)A(M)C(M)C(M)A(M)A(M)U(M)

SEQ ID NO: 10(3):
(sequence obtained by introducing 2'-O-methyl modification into one position of the consensus sequence of the sequence shown in SEQ ID NO: 10)

A(M)U(M)U(M)G(M)G(M)GGC(F)C(F)U(M)C(F)C(F)AC(F)A
(M)G(M)C(M)U(M)G(M)C(M)U(M)C(M)A(M)G(M)C(M)U(M)U
(F)G(M)GAC(F)U(F)AA(M)A(M)C(M)C(M)A(M)A(M)U(M)

SEQ ID NO: 10(4):
(sequence obtained by introducing 2'-O-methyl modification into one position of the consensus sequence of the sequence shown in SEQ ID NO: 10)

A(M)U(M)U(M)G(M)G(M)GGC(F)C(F)U(F)C(M)C(F)AC(F)A
(M)G(M)C(M)U(M)G(M)C(M)U(M)C(M)A(M)G(M)C(M)U(M)U
(F)G(M)GAC(F)U(F)AA(M)A(M)C(M)C(M)A(M)A(M)U(M)

SEQ ID NO: 10(5):
(sequence obtained by introducing 2'-O-methyl modification into one position of the consensus sequence of the sequence shown in SEQ ID NO: 10)

A(M)U(M)U(M)G(M)G(M)G(M)GGC(F)C(F)U(F)C(F)C(F)AC(F)A
(M)G(M)C(M)U(M)G(M)C(M)U(M)C(M)A(M)G(M)C(M)U(M)U
(F)G(M)GAC(F)U(F)AA(M)A(M)C(M)C(M)A(M)A(M)U(M)

SEQ ID NO: 10(6):
(sequence obtained by introducing 2'-O-methyl modification into one position of the sequence other than the consensus sequence of the sequence shown in SEQ ID NO: 10)

A(M)U(M)U(M)G(M)G(M)GGC(F)C(F)U(F)C(F)C(F)AC(F)A
(M)G(M)C(M)U(M)G(M)C(M)U(M)C(M)A(M)G(M)C(M)U(M)U
(M)G(M)GAC(F)U(F)AA(M)A(M)C(M)C(M)A(M)A(M)U(M)

SEQ ID NO: 10(7):
(sequence obtained by introducing 2'-O-methyl modification into one position of the consensus sequence of the sequence shown in SEQ ID NO: 10)

A(M)U(M)U(M)G(M)G(M)GGC(F)C(F)U(F)C(F)C(F)AC(F)A
(M)G(M)C(M)U(M)G(M)C(M)U(M)C(M)A(M)G(M)C(M)U(M)U
(F)G(M)GAC(M)U(F)AA(M)A(M)C(M)C(M)A(M)A(M)U(M)

SEQ ID NO: 10(8):
(sequence obtained by introducing 2'-O-methyl modification into one position of the consensus sequence of the sequence shown in SEQ ID NO: 10)

A(M)U(M)U(M)G(M)G(M)GGC(F)C(F)U(F)C(F)C(F)AC(F)A
(M)G(M)C(M)U(M)G(M)C(M)U(M)C(M)A(M)G(M)C(M)U(M)U
(F)G(M)GAC(F)U(M)AA(M)A(M)C(M)C(M)A(M)A(M)U(M)

SEQ ID NO: 11(1):
(sequence obtained by introducing 2'-O-methyl modification into one position of the sequence other than the consensus sequence of the sequence shown in SEQ ID NO: 11)

A(M)U(M)U(M)G(M)G(M)G(M)GGC(F)C(F)U(F)C(F)C(F)AC(F)A
(M)G(M)C(M)G(M)C(M)U(M)C(M)G(M)C(M)U(M)U(M)G(M)
GAC(F)U(F)AA(M)A(M)C(M)C(M)A(M)A(M)U(M)

SEQ ID NO: 11(2):
(sequence obtained by introducing DNA into one position of the consensus sequence of the sequence shown in SEQ ID NO: 11(1))

A(M)U(M)U(M)G(M)G(M)G(M)gGC(F)C(F)U(F)C(F)C(F)AC(F)A
(M)G(M)C(M)G(M)C(M)U(M)C(M)G(M)C(M)U(M)U(M)G(M)
GAC(F)U(F)AA(M)A(M)C(M)C(M)A(M)A(M)U(M)

SEQ ID NO: 11(3):
(sequence obtained by introducing DNA into one position of the consensus sequence of the sequence shown in SEQ ID NO: 11(1))

A(M)U(M)U(M)G(M)G(M)G(M)GgC(F)C(F)U(F)C(F)C(F)AC(F)A
(M)G(M)C(M)G(M)C(M)U(M)C(M)G(M)C(M)U(M)U(M)G(M)
GAC(F)U(F)AA(M)A(M)C(M)C(M)A(M)A(M)U(M)

SEQ ID NO: 11(4):
(sequence obtained by introducing DNA into one position of the consensus sequence of the sequence shown in SEQ ID NO: 11(1))

A(M)U(M)U(M)G(M)G(M)G(M)GGcC(F)U(F)C(F)C(F)AC(F)A(M)
G(M)C(M)G(M)C(M)U(M)C(M)G(M)C(M)U(M)U(M)G(M)GAC
(F)U(F)AA(M)A(M)C(M)C(M)A(M)A(M)U(M)

SEQ ID NO: 11(5):
(sequence obtained by introducing DNA into one position of the consensus sequence of the sequence shown in SEQ ID NO: 11(1))

A(M)U(M)U(M)G(M)G(M)G(M)GGC(F)cU(F)C(F)C(F)AC(F)A(M)
G(M)C(M)G(M)C(M)U(M)C(M)G(M)C(M)U(M)U(M)G(M)GAC
(F)U(F)AA(M)A(M)C(M)C(M)A(M)A(M)U(M)

SEQ ID NO: 11(6):
(sequence obtained by introducing DNA into one position of the consensus sequence of the sequence shown in SEQ ID NO: 11(1))

A(M)U(M)U(M)G(M)G(M)G(M)GGC(F)C(F)tC(F)C(F)AC(F)A(M)
G(M)C(M)G(M)C(M)U(M)C(M)G(M)C(M)U(M)U(M)G(M)GAC
(F)U(F)AA(M)A(M)C(M)C(M)A(M)A(M)U(M)

SEQ ID NO: 11(7):
(sequence obtained by introducing DNA into one position of the consensus sequence of the sequence shown in SEQ ID NO: 11(1))

A(M)U(M)U(M)G(M)G(M)G(M)GGC(F)C(F)U(F)cC(F)AC(F)A(M)
G(M)C(M)G(M)C(M)U(M)C(M)G(M)C(M)U(M)U(M)G(M)GAC
(F)U(F)AA(M)A(M)C(M)C(M)A(M)A(M)U(M)

SEQ ID NO: 11(8):
(sequence obtained by introducing DNA into one position of the consensus sequence of the sequence shown in SEQ ID NO: 11(1))

A(M)U(M)U(M)G(M)G(M)G(M)GGC(F)C(F)U(F)C(F)cAC(F)A(M)
G(M)C(M)G(M)C(M)U(M)C(M)G(M)C(M)U(M)U(M)G(M)GAC
(F)U(F)AA(M)A(M)C(M)C(M)A(M)A(M)U(M)

SEQ ID NO: 11(9):
(sequence obtained by introducing DNA into one position of the sequence other than the consensus sequence of the sequence shown in SEQ ID NO: 11(1))

A(M)U(M)U(M)G(M)G(M)G(M)GGC(F)C(F)U(F)C(F)C(F)AcA(M)G
(M)C(M)G(M)C(M)U(M)C(M)G(M)C(M)U(M)U(M)G(M)GAC(F)
U(F)AA(M)A(M)C(M)C(M)A(M)A(M)U(M)

SEQ ID NO: 11(10):
(sequence obtained by introducing DNA into one position of the consensus sequence of the sequence shown in SEQ ID NO: 11(1))

A(M)U(M)U(M)G(M)G(M)G(M)GGC(F)C(F)U(F)C(F)C(F)AC(F)A
(M)G(M)C(M)G(M)C(M)U(M)C(M)G(M)C(M)U(M)U(M)G(M)
gAC(F)U(F)AA(M)A(M)C(M)C(M)A(M)A(M)U(M)

SEQ ID NO: 11(11):
(sequence obtained by introducing DNA into one position of the consensus sequence of the sequence shown in SEQ ID NO: 11(1))

A(M)U(M)U(M)G(M)G(M)G(M)GGC(F)C(F)U(F)C(F)C(F)AC(F)A
(M)G(M)C(M)G(M)C(M)U(M)C(M)G(M)C(M)U(M)U(M)G(M)
GaC(F)U(F)AA(M)A(M)C(M)C(M)A(M)A(M)U(M)

SEQ ID NO: 11(12):
(sequence obtained by introducing DNA into one position of the consensus sequence of the sequence shown in SEQ ID NO: 11(1))

A(M)U(M)U(M)G(M)G(M)GGC(F)C(F)U(F)C(F)C(F)AC(F)A
(M)G(M)C(M)G(M)C(M)U(M)C(M)G(M)C(M)U(M)U(M)G(M)
GAcU(F)AA(M)A(M)C(M)C(M)A(M)A(M)U(M)

SEQ ID NO: 11(13):

(sequence obtained by introducing DNA into one position of the consensus sequence of the sequence shown in SEQ ID NO: 11(1))

A(M)U(M)U(M)G(M)G(M)GGC(F)C(F)U(F)C(F)C(F)AC(F)A
(M)G(M)C(M)G(M)C(M)U(M)C(M)G(M)C(M)U(M)U(M)G(M)
GAC(F)tAA(M)A(M)C(M)C(M)A(M)A(M)U(M)

SEQ ID NO: 11(14):

(sequence obtained by introducing DNA into one position of the consensus sequence of the sequence shown in SEQ ID NO: 11(1))

A(M)U(M)U(M)G(M)G(M)GGC(F)C(F)U(F)C(F)C(F)AC(F)A
(M)G(M)C(M)G(M)C(M)U(M)C(M)G(M)C(M)U(M)U(M)G(M)
GAC(F)U(F)aA(M)A(M)C(M)C(M)A(M)A(M)U(M)

SEQ ID NO: 11(15):

(sequence obtained by introducing DNA into one position of the sequence other than the consensus sequence of the sequence shown in SEQ ID NO: 11(1))

A(M)U(M)U(M)G(M)G(M)GGC(F)C(F)U(F)C(F)C(F)aC(F)A
(M)G(M)C(M)G(M)C(M)U(M)C(M)G(M)C(M)U(M)U(M)G(M)
GAC(F)U(F)AA(M)A(M)C(M)C(M)A(M)A(M)U(M)

SEQ ID NO: 11(16):

(sequence obtained by introducing phosphorothioate modification into one position of the sequence shown in SEQ ID NO: 11(1))

A(M)U(M)U(M)G(M)G(M)sGGC(F)C(F)U(F)C(F)C(F)AC(F)A
(M)G(M)C(M)G(M)C(M)U(M)C(M)G(M)C(M)U(M)U(M)G(M)
GAC(F)U(F)AA(M)A(M)C(M)C(M)A(M)A(M)U(M)

SEQ ID NO: 11(17):

(sequence obtained by introducing phosphorothioate modification into one position of the sequence shown in SEQ ID NO: 11(1))

A(M)U(M)U(M)G(M)G(M)GsGC(F)C(F)U(F)C(F)C(F)AC(F)A
(M)G(M)C(M)G(M)C(M)U(M)C(M)G(M)C(M)U(M)U(M)G(M)
GAC(F)U(F)AA(M)A(M)C(M)C(M)A(M)A(M)U(M)

SEQ ID NO: 11(18):

(sequence obtained by introducing phosphorothioate modification into one position of the sequence shown in SEQ ID NO: 11(1))

A(M)U(M)U(M)G(M)G(M)GGsC(F)C(F)U(F)C(F)C(F)AC(F)A
(M)G(M)C(M)G(M)C(M)U(M)C(M)G(M)C(M)U(M)U(M)G(M)
GAC(F)U(F)AA(M)A(M)C(M)C(M)A(M)A(M)U(M)

SEQ ID NO: 11(19):

(sequence obtained by introducing phosphorothioate modification into one position of the sequence shown in SEQ ID NO: 11(1))

A(M)U(M)U(M)G(M)G(M)GGC(F)sC(F)U(F)C(F)C(F)AC(F)A
(M)G(M)C(M)G(M)C(M)U(M)C(M)G(M)C(M)U(M)U(M)G(M)
GAC(F)U(F)AA(M)A(M)C(M)C(M)A(M)A(M)U(M)

SEQ ID NO: 11(20):

(sequence obtained by introducing phosphorothioate modification into one position of the sequence shown in SEQ ID NO: 11(1))

A(M)U(M)U(M)G(M)G(M)GGC(F)C(F)sU(F)C(F)C(F)AC(F)A
(M)G(M)C(M)G(M)C(M)U(M)C(M)G(M)C(M)U(M)U(M)G(M)
GAC(F)U(F)AA(M)A(M)C(M)C(M)A(M)A(M)U(M)

SEQ ID NO: 11(21):

(sequence obtained by introducing phosphorothioate modification into one position of the sequence shown in SEQ ID NO: 11(1))

A(M)U(M)U(M)G(M)G(M)GGC(F)C(F)U(F)sC(F)C(F)AC(F)A
(M)G(M)C(M)G(M)C(M)U(M)C(M)G(M)C(M)U(M)U(M)G(M)
GAC(F)U(F)AA(M)A(M)C(M)C(M)A(M)A(M)U(M)

SEQ ID NO: 11(22):

(sequence obtained by introducing phosphorothioate modification into one position of the sequence shown in SEQ ID NO: 11(1))

A(M)U(M)U(M)G(M)G(M)GGC(F)C(F)U(F)C(F)sC(F)AC(F)A
(M)G(M)C(M)G(M)C(M)U(M)C(M)G(M)C(M)U(M)U(M)G(M)
GAC(F)U(F)AA(M)A(M)C(M)C(M)A(M)A(M)U(M)

SEQ ID NO: 11(23):

(sequence obtained by introducing phosphorothioate modification into one position of the sequence shown in SEQ ID NO: 11(1))

A(M)U(M)U(M)G(M)G(M)GGC(F)C(F)U(F)C(F)C(F)sAC(F)A
(M)G(M)C(M)G(M)C(M)U(M)C(M)G(M)C(M)U(M)U(M)G(M)
GAC(F)U(F)AA(M)A(M)C(M)C(M)A(M)A(M)U(M)

SEQ ID NO: 11(24):

(sequence obtained by introducing phosphorothioate modification into one position of the sequence shown in SEQ ID NO: 11(1))

A(M)U(M)U(M)G(M)G(M)GGC(F)C(F)U(F)C(F)C(F)AsC(F)A
(M)G(M)C(M)G(M)C(M)U(M)C(M)G(M)C(M)U(M)U(M)G(M)
GAC(F)U(F)AA(M)A(M)C(M)C(M)A(M)A(M)U(M)

SEQ ID NO: 11(25):

(sequence obtained by introducing phosphorothioate modification into one position of the sequence shown in SEQ ID NO: 11(1))

A(M)U(M)U(M)G(M)G(M)G(M)GGC(F)C(F)U(F)C(F)C(F)AC(F)sA
(M)G(M)C(M)G(M)C(M)U(M)C(M)G(M)C(M)U(M)U(M)G(M)
GAC(F)U(F)AA(M)A(M)C(M)C(M)A(M)A(M)U(M)

SEQ ID NO: 11(26):
(sequence obtained by introducing phosphorothioate modification into one position of the sequence shown in SEQ ID NO: 11(1))

A(M)U(M)U(M)G(M)G(M)G(M)GGC(F)C(F)U(F)C(F)C(F)AC(F)A
(M)G(M)C(M)G(M)C(M)U(M)C(M)G(M)C(M)U(M)U(M)G(M)
sGAC(F)U(F)AA(M)A(M)C(M)C(M)A(M)A(M)U(M)

SEQ ID NO: 11(27):
(sequence obtained by introducing phosphorothioate modification into one position of the sequence shown in SEQ ID NO: 11(1))

A(M)U(M)U(M)G(M)G(M)G(M)GGC(F)C(F)U(F)C(F)C(F)AC(F)A
(M)G(M)C(M)G(M)C(M)U(M)C(M)G(M)C(M)U(M)U(M)G(M)
GsAC(F)U(F)AA(M)A(M)C(M)C(M)A(M)A(M)U(M)

SEQ ID NO: 11(28):
(sequence obtained by introducing phosphorothioate modification into one position of the sequence shown in SEQ ID NO: 11(1))

A(M)U(M)U(M)G(M)G(M)G(M)GGC(F)C(F)U(F)C(F)C(F)AC(F)A
(M)G(M)C(M)G(M)C(M)U(M)C(M)G(M)C(M)U(M)U(M)G(M)
GAsC(F)U(F)AA(M)A(M)C(M)C(M)A(M)A(M)U(M)

SEQ ID NO: 11(29):
(sequence obtained by introducing phosphorothioate modification into one position of the sequence shown in SEQ ID NO: 11(1))

A(M)U(M)U(M)G(M)G(M)G(M)GGC(F)C(F)U(F)C(F)C(F)AC(F)A
(M)G(M)C(M)G(M)C(M)U(M)C(M)G(M)C(M)U(M)U(M)G(M)
GAC(F)sU(F)AA(M)A(M)C(M)C(M)A(M)A(M)U(M)

SEQ ID NO: 11(30):
(sequence obtained by introducing phosphorothioate modification into one position of the sequence shown in SEQ ID NO: 11(1))

A(M)U(M)U(M)G(M)G(M)G(M)GGC(F)C(F)U(F)C(F)C(F)AC(F)A
(M)G(M)C(M)G(M)C(M)U(M)C(M)G(M)C(M)U(M)U(M)G(M)
GAC(F)U(F)sAA(M)A(M)C(M)C(M)A(M)A(M)U(M)

SEQ ID NO: 11(31):
(sequence obtained by introducing phosphorothioate modification into one position of the sequence shown in SEQ ID NO: 11(1))

A(M)U(M)U(M)G(M)G(M)G(M)GGC(F)C(F)U(F)C(F)C(F)AC(F)A
(M)G(M)C(M)G(M)C(M)U(M)C(M)G(M)C(M)U(M)U(M)G(M)
GAC(F)U(F)AsA(M)A(M)C(M)C(M)A(M)A(M)U(M)

SEQ ID NO: 13:
(sequence obtained by substituting 2 nucleotides on the both terminals of the sequence shown in SEQ ID NO: 11(1) with other sequence)

G(M)C(M)U(M)G(M)G(M)GGC(F)C(F)U(F)C(F)C(F)AC(F)A
(M)G(M)C(M)G(M)C(M)U(M)C(M)G(M)C(M)U(M)U(M)G(M)
GAC(F)U(F)AA(M)A(M)C(M)C(M)A(M)G(M)C(M)

SEQ ID NO: 14:
(sequence obtained by substituting 4 nucleotides of the loop region of the sequence shown in SEQ ID NO: 11(1) with other sequence)

A(M)U(M)U(M)G(M)G(M)G(M)GGC(F)C(F)U(F)C(F)C(F)AC(F)A
(M)G(M)C(M)U(M)U(M)C(M)G(M)G(M)C(M)U(M)U(M)G(M)
GAC(F)U(F)AA(M)A(M)C(M)C(M)A(M)A(M)U(M)

SEQ ID NO: 11(32):
(sequence obtained by introducing phosphorothioate modification into 4 positions of the sequence shown in SEQ ID NO: 11(1) and adding idT to 3'-terminal)

A(M)U(M)U(M)G(M)G(M)G(M)GGC(F)sC(F)sU(F)sC(F)C(F)AC
(F)sA(M)G(M)C(M)G(M)C(M)U(M)C(M)G(M)C(M)U(M)U(M)
G(M)GAC(F)U(F)AA(M)A(M)C(M)C(M)A(M)A(M)U(M)-idT

SEQ ID NO: 11(33):
(sequence obtained by adding 40 kDa polyethylene glycol to 5'-terminal and idT to 3'-terminal of the sequence shown in SEQ ID NO: 11(1))

PEG-

A(M)U(M)U(M)G(M)G(M)G(M)GGC(F)C(F)U(F)C(F)C(F)AC(F)A (M)G(M)C(M)G(M)C(M)U(M)C(M)G(M)C(M)U(M)U(M)G(M)

GAC(F)U(F)AA(M)A(M)C(M)C(M)A(M)A(M)U(M)-idT

SEQ ID NO: 11(34):
(sequence obtained by adding idT to 3'-terminal of the sequence shown in SEQ ID NO: 11(19))

A(M)U(M)U(M)G(M)G(M)G(M)GGC(F)sC(F)U(F)C(F)C(F)AC(F)A
(M)G(M)C(M)G(M)C(M)U(M)C(M)G(M)C(M)U(M)U(M)G(M)
GAC(F)U(F)AA(M)A(M)C(M)C(M)A(M)A(M)U(M)-idT

SEQ ID NO: 11(35):
(sequence obtained by adding 40 kDa polyethylene glycol to 5'-terminal and idT to 3'-terminal of the sequence shown in SEQ ID NO: 11(19))

PEG-

A(M)U(M)U(M)G(M)G(M)G(M)GGC(F)sC(F)U(F)C(F)C(F)AC(F)A (M)G(M)C(M)G(M)C(M)U(M)C(M)G(M)C(M)U(M)U(M)G(M)

GAC(F)U(F)AA(M)A(M)C(M)C(M)A(M)A(M)U(M)-idT

SEQ ID NO: 15:
(sequence obtained by randomly rearranging the consensus sequence in the sequence shown in SEQ ID NO: 11(34))

A(M)U(M)U(M)G(M)G(M)C(F)sA(M)C(F)GGAG(M)AC(F)A(M)
G(M)C(M)G(M)C(M)U(M)C(M)G(M)C(M)U(M)U(M)C(F)U(F)C
(F)GA(M)U(F)C(F)AC(M)C(M)A(M)A(M)U(M)-idT

The aptamers having the sequences shown in SEQ ID NOs: 10(1)-10(8) and 11(1)-11(35), SEQ ID NO: 13-15 were all produced by chemical synthesis. Whether these aptamers inhibit the enzyme activity of ADAMTS5 was determined by a method similar to that in Example 1 (evaluation method 1) for the aptamers having the sequences shown by the sequences of SEQ ID NOs: 10(1)-10(8) and 11(1)-11(33), SEQ ID NOs: 13 and 14. The final concentration of the nucleic acids in the evaluation was 10 nM. The results are shown in evaluation method 1 of Table 6.

On the other hand, the aptamers having the sequences shown by the sequences of SEQ ID NOs: 11(34)-11(35) and SEQ ID NO: 15 were evaluated by the following method (evaluation method 2). The cleavage reaction of the substrate (aggrecan G1-IGD-G2) by ADAMTS5 was performed in the same manner as in Example 1 except the following points. The differences are that the final concentrations of ADAMTS5 and the substrate were respectively 0.2 nM and 400 nM (48 µg/mL), and that the enzyme reaction time was 30 min. After the reaction, the reaction was stopped by adding an excess amount of an ADAMTS5 small molecule inhibitor. The cleaved substrate was quantified by a sandwich ELISA method using two kinds of anti-aggrecan antibodies. As the anti-aggrecan antibodies, MAB6489 manufactured by R&D Systems and biotinylated MAB1220 were used. MAB6489 is an antibody that specifically recognizes the cleavage surface of aggrecan cleaved by ADAMTS5. Using this, the amount of cleaved substrate can be quantified. Detection was performed by a standard ELISA detection method using horseradish peroxidase-labeled streptavidin. The substrate cleavage efficiency of ADAMTS5 under these reaction conditions was about 7%. The inhibition rate of the test substance was calculated using the following equation.

inhibition rate (%)=$(P_E-P_{apt})/(P_E-P_0)\times 100$ wherein $P_E$ is the amount of a cleaved substrate with the addition of ADAMTS5, $P_{apt}$ is the amount of a cleaved substrate with the addition of a test substance, and $P_0$ is the residual amount of a cleaved substrate without the addition of ADAMTS5.

The measurement results of the inhibitory activity of the aptamers having the sequences shown in SEQ ID NOs: 11(34)-11(35) and SEQ ID NO: 15 are shown in Table 6, evaluation method 2. In the Table, "evaluation method 1", shows inhibitory activity under 10 nM aptamer concentration condition. The "evaluation method 2" shows inhibitory activity under 2 nM aptamer concentration condition. "n.d." means not determined.

TABLE 6

Inhibitory activity against ADAMTS5

| SEQ ID NO: | inhibitory activity (%) | |
|---|---|---|
| | evaluation method 1 | evaluation method 2 |
| 10 | 65 | n.d. |
| 10(1) | 41.3 | n.d. |
| 10(2) | 12.6 | n.d. |
| 10(3) | 2 | n.d. |
| 10(4) | 3.6 | n.d. |
| 10(5) | 8.5 | n.d. |
| 10(6) | 61.8 | n.d. |
| 10(7) | 10.4 | n.d. |
| 10(8) | 12.8 | n.d. |
| 11 | 59.8 | n.d. |
| 11(1) | 62.8 | n.d. |
| 11(2) | 60.6 | n.d. |
| 11(3) | 19.5 | n.d. |
| 11(4) | 50.9 | n.d. |
| 11(5) | 34.2 | n.d. |
| 11(6) | 9.2 | n.d. |

TABLE 6-continued

Inhibitory activity against ADAMTS5

| SEQ ID NO: | inhibitory activity (%) | |
|---|---|---|
| | evaluation method 1 | evaluation method 2 |
| 11(7) | 23 | n.d. |
| 11(8) | 43.2 | n.d. |
| 11(9) | 60.8 | n.d. |
| 11(10) | 59.1 | n.d. |
| 11(11) | 32 | n.d. |
| 11(12) | 62.5 | n.d. |
| 11(13) | 20.3 | n.d. |
| 11(14) | 45.1 | n.d. |
| 11(15) | 50.4 | n.d. |
| 11(16) | 50.9 | n.d. |
| 11(17) | 70 | n.d. |
| 11(18) | 60.3 | n.d. |
| 11(19) | 81.1 | n.d. |
| 11(20) | 74.7 | n.d. |
| 11(21) | 80.3 | n.d. |
| 11(22) | 49.8 | n.d. |
| 11(23) | 47.9 | n.d. |
| 11(24) | 46.3 | n.d. |
| 11(25) | 76.4 | n.d. |
| 11(26) | 47.2 | n.d. |
| 11(27) | 48.2 | n.d. |
| 11(28) | 44.8 | n.d. |
| 11(29) | 56.5 | n.d. |
| 11(30) | 38.3 | n.d. |
| 11(31) | 56.3 | n.d. |
| 13 | 58.4 | n.d. |
| 14 | 60.5 | n.d. |
| 11(32) | 58.8 | n.d. |
| 11(33) | 55.5 | n.d. |
| 11(34) | n.d. | 84.1 |
| 11(35) | n.d. | 56 |
| 15 | n.d. | 16.5 |

Among the variants with introduction of 2'-O-methylation modification, the aptamers having the sequences shown in SEQ ID NOs: 10(1), 10(6) (SEQ ID NO: 10 lineage) and SEQ ID NO: 11(1) (SEQ ID NO: 11 lineage) maintained the inhibitory activity, albeit with varying strength. On the other hand, the aptamers having the sequences shown in SEQ ID NOs: 10(2)-10(5) and 10(7), 10(8) showed markedly reduced inhibitory activity. From the above results, it was found that an aptamer having 2'-O-methylation modification introduced into the 5th C from the 5'-terminal and the 10th G from the 3'-terminal of the consensus sequence also functions. In addition, the 2'-O-methylation modification significantly reduced the aptamer inhibitory activity in most of the internal loops in the consensus sequence, which suggests that this region may be important for aptamer activity.

Among the variants introduced with DNA (SEQ ID NO: 11 lineage), aptamers having the sequences shown in SEQ ID NOs: 11(2), 11(4), 11(8), 11(9), 11(10), 11(12), 11(14), 11(15) maintained the inhibitory activity, albeit with varying strength. From the above results, it was found that an aptamer having DNA for the 3rd G, the 5th C, and the 9th C from the 5'-terminal and the 9th G, the 7th C, and the 5th A from the 3'-terminal of the consensus sequence also functions. As the modification of nucleotide, for example, 2'-amino modification and the like can be mentioned besides the 2'-O-methyl modification and DNA. Among SEQ ID NOs: 11(16)-11(32) with phosphorothioate modification introduced into a phosphoric acid group, all sequences except the aptamer having the sequence shown in SEQ ID NO: 11(30) maintained the inhibitory activity, albeit with varying strength. Among others, the aptamers having the sequences shown in SEQ ID NOs: 11(19)-11(21), 11(25) showed improved inhibitory activity. From the results of the aptamer having the sequence shown in SEQ ID NO: 13, it was found that the substitution of the two base pairs, AU pair and UA pair, on the terminal respectively with GC pair and CG pair does not affect the inhibitory activity. From the results of the aptamer having the sequence shown in SEQ ID NO: 14, it was found that the substitution of a loop sequence constituted of the 18th to 21st bases with GCUC to UUCG does not affect the inhibitory activity.

From the results of the aptamers having the sequences shown in SEQ ID NOs: 11(33)-(35), it was found that addition of PEG to the 5'-terminal and idT to the 3'-terminal does not affect the inhibitory activity. As the terminal modification, for example, peptide, amino acid, sugar, glycosaminoglycan, biotin and the like can be mentioned besides PEG and idT. From the above, it was found that the aptamer of the present invention containing the formula (1) or the formula (1)' can be modified in various ways.

Example 6: Production of RNA Aptamer that Specifically Binds to ADAMTS5-(2)

Using a random sequence having a primer sequence different from that in Example 1 as a template, SELEX was performed in the same manner as in Example 1. As a target substance of SELEX, ADAMTS5 (manufactured by R&D systems) immobilized on NHS-activated Sepharose 4 Fast Flow (manufactured by GE Healthcare) as a carrier was used. The sequences of the templates and primers used are shown below. A mutation is introduced into the template DNA based on the sequence of SEQ ID NO: 3.

```
DNA template:
                                        (SEQ ID NO: 49)
5'-TGCTCGATCTGGACT(G)(G)(A)(T)(T)(G)(G)(T)(T)(T)

(A)(G)(T)(C)(C)(A)(A)(G)(C)(T)(G)(A)(G)(C)(A)(G)

(C)(T)(G)(T)(G)(G)(A)(G)(G)(C)(C)(C)(C)(A)(A)(T)

(C)(C)AGTTACGCATGTCCC-3' primer Fwd:
                                        (SEQ ID NO: 50)
5'-TAATACGACTCACTATAGGGACATGCGTAACT-3' primer Rev:
                                        (SEQ ID NO: 51)
5'-TGCTCGATCTGGACT-3'
```

The parentheses in the DNA template (SEQ ID NO: 49) indicate introduction of modification, and the template is designed to contain 76% of the nucleotides indicated in the parentheses, and 8% each of other 3 kinds of nucleotides. The primer Fwd comprises a promoter sequence of T7 RNA polymerase. The variation of the RNA pool used in the first round was theoretically $10^{13}$.

RNA pool was added to the carrier on which ADAMTS5 was immobilized, and the mixture was maintained at room temperature for 30 min. The resin was washed with solution A to remove RNA not bound to ADAMTS5. Here, solution A is a mixed solution of 145 mM sodium chloride, 5.4 mM potassium chloride, 1.8 mM calcium chloride, 0.8 mM magnesium chloride, 20 mM tris (pH 7.6), and 0.05% Tween 20. The RNA bound to ADAMTS5 was obtained by adding solution B as an eluate, heat treating the mixture at 95° C. for 3 min and collecting from the supernatant thereof. Here, solution B is a mixed solution of 7 M Urea, 5 mM EDTA, and 20 mM tris (pH 7.6). The recovered RNA was amplified by reverse transcription PCR, transcribed using DuraScribe™ T7 Transcription Kit and used as a pool for the next round. With the above as 1 round, a similar operation was repeated plural times. After completion of SELEX, the PCR product was cloned to pGEM-T Easy vector (manufactured by Promega), and *Escherichia coli* strain DH5 (manufactured by Toyobo) was transformed. After extraction of plasmid from a single colony, the base sequence of the clone was examined by a capillary DNA sequencer (3130xl Genetic Analyzer, manufactured by ABI). A large-scale analysis of the base sequence was also performed using a next generation sequencer. As the next generation sequencer, Ion PGM™ system (manufactured by Thermo) was used and the analysis was performed according to the manual of Thermo.

After 7 rounds of SELEX, the sequences of 48 clones were determined by a capillary DNA sequencer to find that the sequences of 26 clones contained the consensus sequence 1 or 2 shown below. A part of the sequences of these clones is shown in SEQ ID NOs: 16-20.

Figures 1, 5:
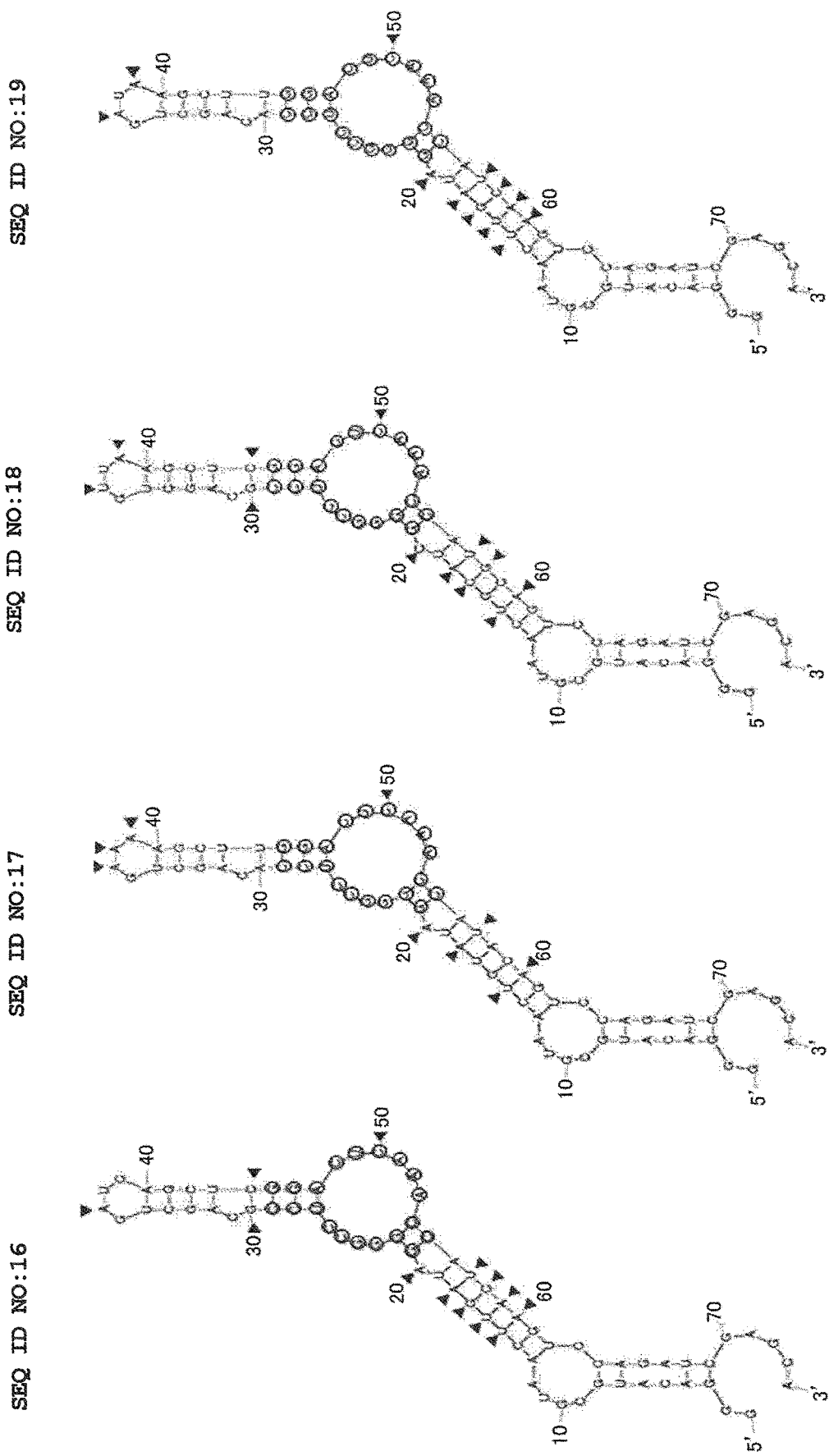
Figures 1, 7:
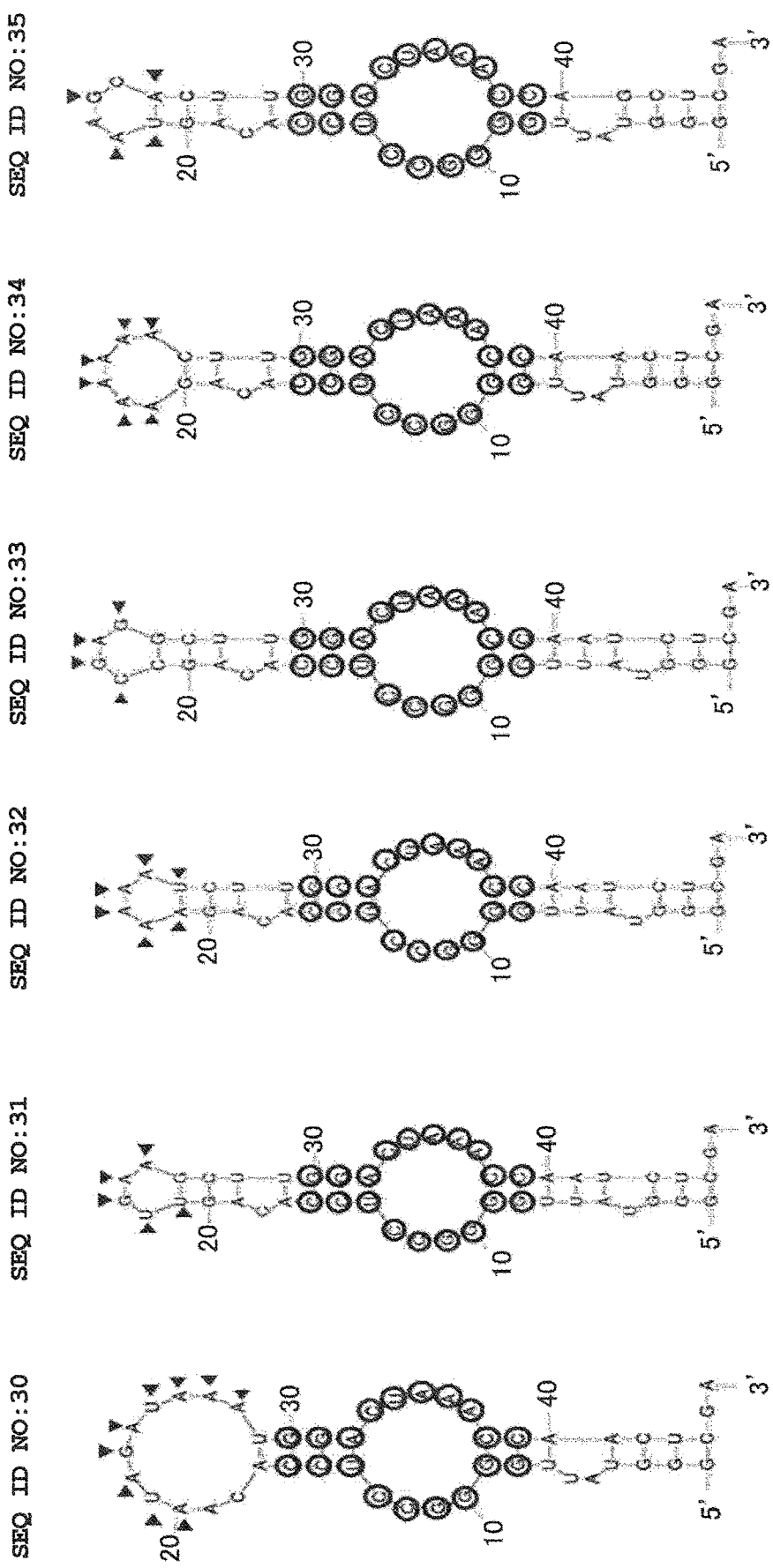
Figures 2, 7:
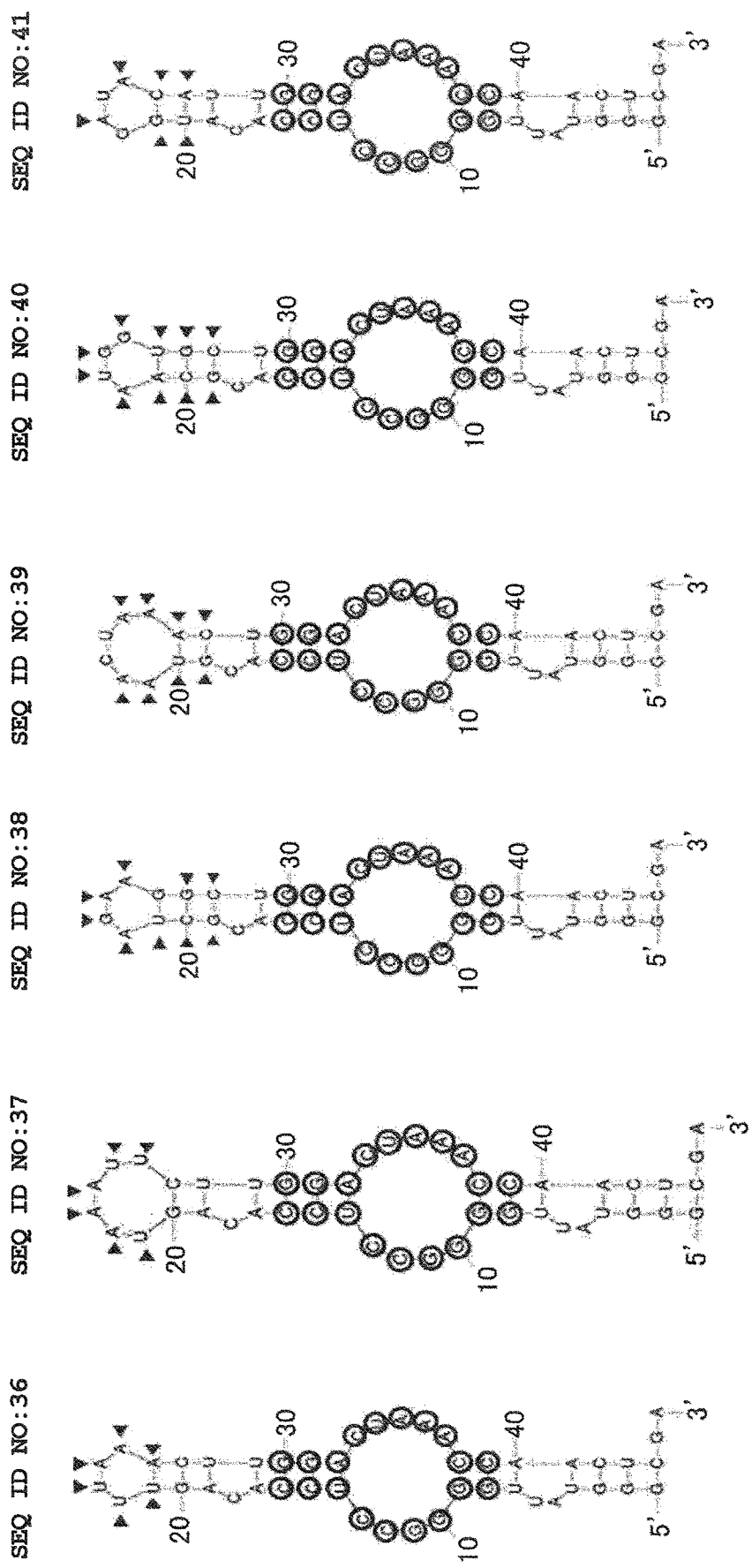
Figures 3, 7:
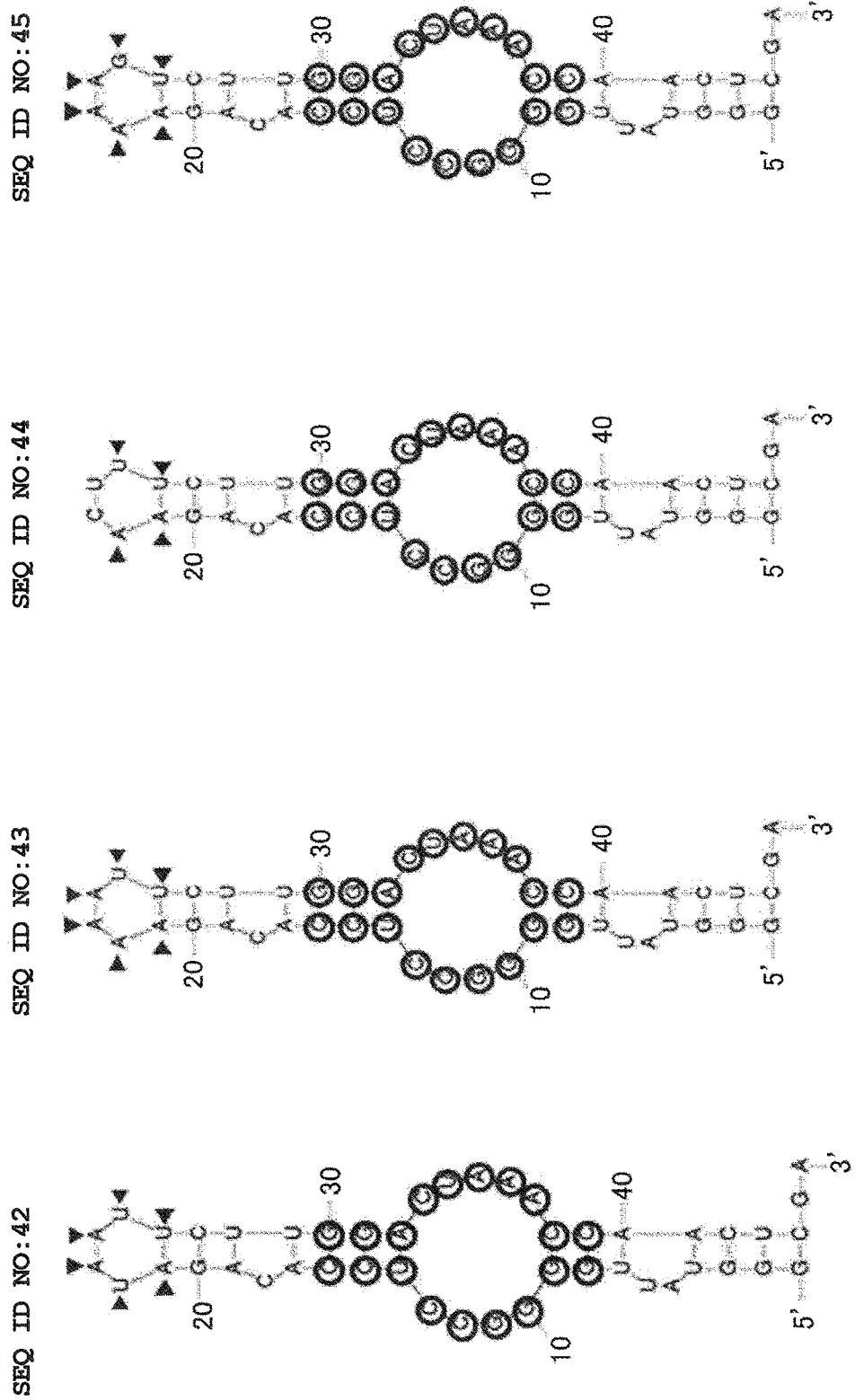

In addition, 47623 kinds of clone sequences were determined by the next generation sequencer, and they were confirmed to converge to 12728 kinds of sequence. Some sequences of those clones are shown in SEQ ID NOs: 21-25. There existed 1,045 sequences shown in SEQ ID NO: 21. There existed 595 sequences shown in SEQ ID NO: 22. There existed 557 sequences shown in SEQ ID NO: 23. There existed 442 sequences shown in SEQ ID NO: 24. There existed 288 sequences shown in SEQ ID NO: 25. The secondary structures of these sequences were predicted by the MFOLD program (M. Zuker, Nucleic Acids Res. 31(13), 3406-3415, 2003). As a result, the consensus sequence portion had a similar loop structure. The secondary structures of these sequences are presented in FIG. 5-1 and FIG. 5-2. In FIG. 5-1 and FIG. 5-2, the consensus sequences are enclosed with a circle (○). In addition, sequences different from SEQ ID NO: 3 are indicated by an arrow (black triangle).

Respective nucleotide sequences shown in SEQ ID NOs: 16-25 are presented below. Unless particularly indicated, the sequences shown below are in the 5' to 3' direction, purine bases (A and G) are 2'-OH compounds and pyrimidine bases (U and C) are 2'-fluoro modified compounds. $N_1$ in the sequences shows 6-15 nucleotides with any length, W is A or U, and Y is C or U.

```
SEQ ID NO: 16:
GGGACAUGCGUAACUUGAUAGGGGCCUCCGCAGCUGAUCAGCUCGGACU
CAAACCAUCAAGUCCAGAUCGAGCA

SEQ ID NO: 17:
GGGACAUGCGUAACUGUAUAGGGGCCUCCACAGCUGAAAAGCUUGGACU
CAAACCAUACAGUCCAGAUCGAGCA

SEQ ID NO: 18:
GGGACAUGCGUAACUGCAUCGGGGCCUCCGCAGCUGUUAAGCUCGGACU
CAAACCAUGCAGUCCAGAUCGAGCA

SEQ ID NO: 19:
GGGACAUGCGUAACUUGAUAGGGGCCUCCACAGCUGAUAAGCUUGGACU
CAAACCAUCAAGUCCAGAUCGAGCA

SEQ ID NO: 20:
GGGACAUGCGUAACUGUAUAGGGGCCUCCGCAGCUAUUCAGCUCGGACA
UAAACCAUACAGUCCAGAUCGAGCA
```

-continued

SEQ ID NO: 21:
GGGACAUGCGUAACUAUAUAGGGGCCUCCACAGCUGUAAAGCUUGGACU
UAAACCAUAUAGAGUCCAGAUCGAGCA

SEQ ID NO: 22:
GGGACAUGCGUAACUGCAUAGGGGCCUCCACAGCUAUUCAGCUUGGACA
CAAACCAUGCAGUCCAGAUCGAGCA

SEQ ID NO: 23:
GGGACAUGCGUAACUGUAUAGGGGCCUCCACAGCUGAAAAGCUUGGACU
CAAACCAUACAGUCCAGAUCGAGCA

SEQ ID NO: 24:
GGGACAUGCGUAACUUGAUAGGGGCCUCCACAGCCGGUAGGCUUGGACU
CAAACCAUCAAGUCCAGAUCGAGCA

SEQ ID NO: 25:
GGGACAUGCGUAACUGCAUAGGGGCCUCCACAGCUAUUCAGCUUGGACA
CAAACCAUGCAGUCCAGAUCGAGCA consensus sequence 1:
(SEQ ID NO: 55)
GGGGCCUCC-N$_1$-GGACYAAAC consensus sequence 2:
(SEQ ID NO: 56)
GGGGCCUCC-N$_1$-GGACWYAAAC The binding activity and enzyme inhibitory activity of aptamers having nucleotide sequences shown in SEQ ID NOs: 16-25 to ADAMTS5 were measured. The binding activity was evaluated by the surface plasmon resonance method. For the measurement, a method similar to that in Example 1 was used. The enzyme inhibitory activity was measured by a method similar to that in Example 1. The measurement results are shown in Table 7. In the Table, "++" and "+" show those that bind to ADAMTS5 more significantly than the negative control nucleic acid. The negative control nucleic acid refers to the nucleic acid pool used in the first round of the SELEX method. The "++" indicates those with the proportion of ADAMTS5 binding amount (RU value) to the amount of aptamer immobilized on the SA chip (RU value) of not less than 40%, and "+" indicates those with the proportion of less than 40%. The numerical value of the inhibitory activity shows the enzyme inhibitory activity at each aptamer concentration shown in the Table. "n.d." means not determined.

TABLE 7 binding activity to and inhibitory activity against ADAMTS5

| SEQ ID NO: | length | binding activity | inhibitory activity % | | |
|---|---|---|---|---|---|
| | | | 30 nM aptamer | 20 nM aptamer | 10 nM aptamer |
| 16 | 74 | + | 93.6 | n.d. | 46.3 |
| 17 | 74 | + | 88.2 | n.d. | 12.3 |
| 18 | 74 | + | 90.4 | n.d. | 2.9 |
| 19 | 74 | + | 93.5 | n.d. | 2.9 |
| 20 | 74 | + | 111.1 | n.d. | 15.5 |
| 21 | 76 | ++ | n.d. | n.d. | 56.9 |
| 22 | 74 | ++ | n.d. | n.d. | 14.8 |
| 23 | 74 | ++ | n.d. | n.d. | 14.5 |
| 24 | 74 | ++ | n.d. | n.d. | 20.2 |
| 25 | 74 | ++ | n.d. | 72.1 | n.d. |

It was shown that the aptamers having the sequences shown in SEQ ID NOs: 16-25 bind to ADAMTS5 more significantly than the negative control nucleic acid. It was also found that all nucleic acids showed an inhibitory activity, albeit with varying strength.

Also, from the results of the prediction of the secondary structure, the binding activity, and the inhibitory activity of the aptamers having the sequences shown in SEQ ID NOs: 16-25, it was found that the terminal stem sequence adjacent to the consensus sequence functions even if it contains a bulge structure. The bulge structure refers to a structure having a protruding nucleotide sequence that does not form a base pair within the stem structure. The bulge structure was contained in the stem structure of the aptamers having the sequences shown in SEQ ID NOs: 16-25.

Example 7: Strand-Shortening of Aptamer-(3)

Strand-shortening and base substitution of the aptamers having the sequences shown in SEQ ID NOs: 21 and 25 were performed. The sequences of the aptamers are shown in SEQ ID NO: 26-29.

Figure 6:
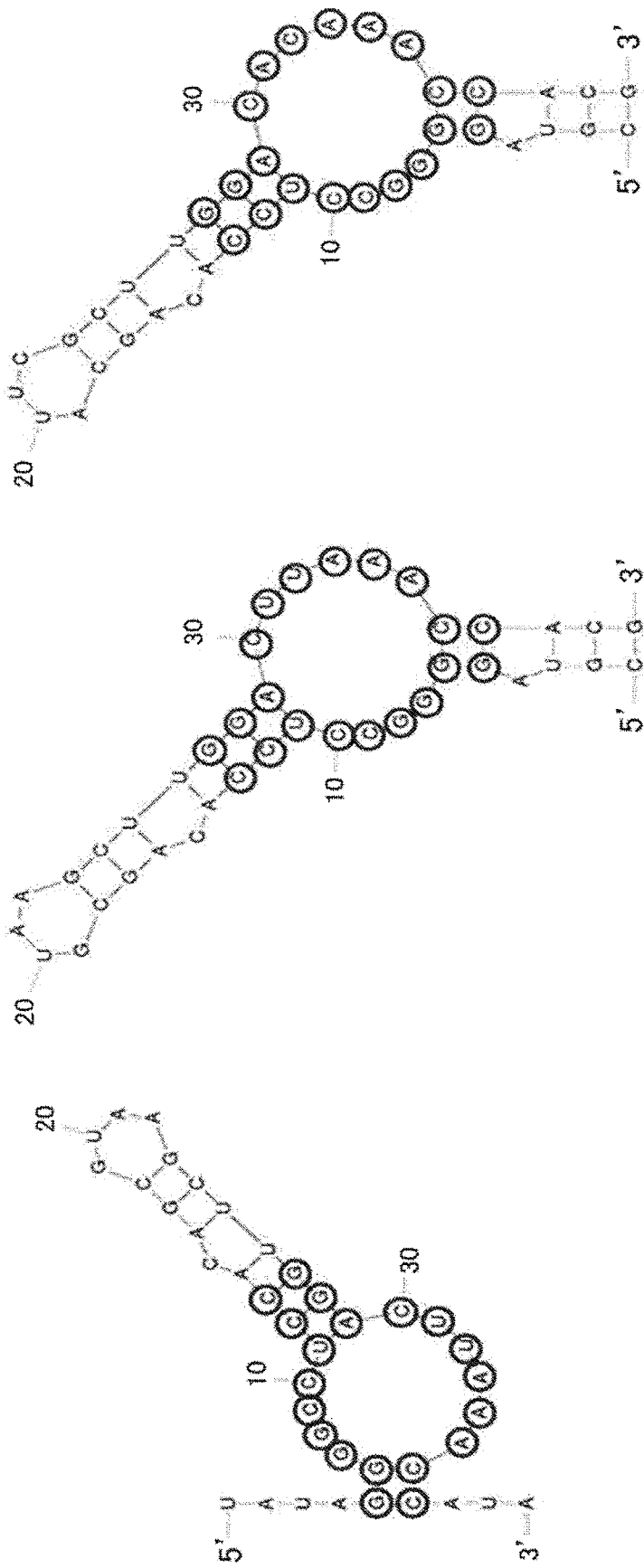
FIG. 6 shows the secondary structure of an aptamer having the nucleotide sequence shown in SEQ ID NOs: 27 to 29 as predicted from the MFOLD program.

As for SEQ ID NOs: 27, 28 and 29, based on the results of the introduction of the modification of SEQ ID NO: 11(1), 2'-O-methyl modification was introduced and then the strands were shortened. The predicted secondary structures of the aptamers having the sequences shown in SEQ ID NOs: 27-29 are presented in FIG. 6. In FIG. 6, the consensus sequences are enclosed with a circle (0). The nucleotide sequences of the nucleotide sequences shown in the following SEQ ID NOs: 26-29 are presented below. Unless particularly indicated, each sequence shown below is in the 5' to 3' direction, and capital letters indicate RNA. The parentheses in the nucleotides indicate modification of the 2'-position of ribose, F is a fluorine atom, and M is an O-methyl group. The "idT" is an inverted dT.

SEQ ID NO: 26:
(sequence obtained by shortening the sequence shown in SEQ ID NO: 21 to a length of 46 nucleotides including the consensus sequence)

GGGU(F)AU(F)AGGGGC(F)C(F)U(F)C(F)C(F)AC(F)AGC(F)
GU(F)AAGC(F)U(F)U(F)GGAC(F)U(F)AAAC(F)C(F)AU
(F)AC(F)C(F)C(F)

SEQ ID NO: 27:
(sequence obtained by introducing 2'-O-methyl modification into the sequence shown in SEQ ID NO: 21 to reflect modification of the 2'-position of SEQ ID NO: 11(1), and shortening to a length of 40 nucleotides containing the consensus sequence)

U(M)A(M)U(M)AG(M)G(M)GGC(F)C(F)U(F)C(F)C(F)AC(F)
A(M)G(M)C(M)G(M)U(F)AAG(M)C(M)U(M)U(M)G(M)GAC(F)
U(F)U(F)AA(M)A(M)C(M)C(M)A(M)U(M)A(M)

SEQ ID NO: 28:
(sequence obtained by substituting two nucleotides on both terminals of the sequence shown in SEQ ID NO: 27 with other sequence)

C(M)G(M)U(M)AG(M)G(M)GGC(F)C(F)U(F)C(F)C(F)AC(F)
A(M)G(M)C(M)G(M)U(F)AAG(M)C(M)U(M)U(M)G(M)GAC(F)
U(F)U(F)AA(M)A(M)C(M)C(M)A(M)C(M)G(M)

SEQ ID NO: 29:
(sequence obtained by introducing 2'-O-methyl modification into the sequence shown in SEQ ID NO: 25 to reflect modification of the 2'-position of SEQ ID NO: 11(1), shortening to a length of 40 nucleotides containing the consensus sequence, and adding idT to 3'-terminal)

C(M)G(M)U(M)A(M)G(M)G(M)GGC(F)C(F)U(F)C(F)C(F)AC
(F)A(M)G(M)C(M)A(M)U(M)U(M)C(M)G(M)C(M)U(M)U(M)G
(M)GAC(F)AC(F)AA(M)A(M)C(M)C(M)A(M)C(M)G(M)-idT

The aptamer having the sequence shown in SEQ ID NO: 26 was prepared by transcription by T7RNA polymerase, and the aptamers having the sequences shown in SEQ ID NOs: 27-29 were prepared by chemical synthesis. Whether these aptamers inhibit the enzyme activity of ADAMTS5 was evaluated by a method similar to that in Example 1. The measurement results are shown in Table 8. In the Table, "n.d." means not determined.

TABLE 8

| | | | inhibitory activity against ADAMTS5 | | |
|---|---|---|---|---|---|
| | | | inhibitory activity % | | |
| SEQ ID NO: | preparation method | length | 30 nM aptamer | 10 nM aptamer | IC$_{50}$ (nM) |
| 21 | transcription | 74 | 78.8 | n.d. | n.d. |
| 26 | transcription | 46 | 63.5 | n.d. | n.d. |
| 27 | chemical synthesis | 40 | n.d. | n.d. | 5.9 |
| 28 | chemical synthesis | 40 | n.d. | n.d. | 3.4 |
| 29 | chemical synthesis | 40 | n.d. | 84 | n.d |

The aptamers having the sequences shown in SEQ ID NOs: 26-29 all maintained the inhibitory activity. From the above results, it was found that the aptamers shown in SEQ ID NOs: 21 and 25 function with a length of 40 nucleotides including the consensus sequence. From the results of the aptamers having the sequences shown in SEQ ID NOs: 27 and 28, it was found that the substitution of the two base pairs on the terminal, UA pair and AU pair, with CG pair and GC pair respectively does not affect the activity.

Example 8: Alteration of Aptamer-3

To enhance the nuclease resistance of aptamers having the nucleotide sequences shown in SEQ ID NOs: 28, 29, a variant with terminal modification, a variant with fluoro group introduction, and a variant with 2'-O-methyl group introduction were produced. The modified sequences are shown in SEQ ID NOs: 28(1)-28(18) (SEQ ID NO: 28 lineage), 29(1)-29(3) (SEQ ID NO: 29 lineage).

The nucleotide sequences shown in SEQ ID NOs: 28(1)-28(18), 29(1)-29(3) are presented below. Unless particularly indicated, each sequence shown below is in the 5' to 3' direction, and capital letters indicate RNA. The parentheses in the nucleotides indicate modification of the 2'-position of ribose, F is a fluorine atom, and M is an O-methyl group. The idT at the sequence terminal shows modification with inverted-dT, and PEG shows modification with 40 kDa branched-type polyethylene glycol.

SEQ ID NO: 28(1):
(sequence obtained by introducing 2'-O-methyl modification into 3 positions of the sequence other than the consensus sequence of the sequence shown in SEQ ID NO: 28)

C(M)G(M)U(M)AG(M)G(M)GGC(F)C(F)U(F)C(F)C(F)AC(F)
A(M)G(M)C(M)G(M)U(M)A(M)A(M)G(M)C(M)U(M)U(M)G(M)
GAC(F)U(F)U(F)AA(M)A(M)C(M)C(M)A(M)C(M)G(M)

SEQ ID NO: 28(2):
(sequence obtained by introducing 2'-O-methyl modification into one position other than the consensus sequence of the sequence shown in SEQ ID NO: 28)

C(M)G(M)U(M)A(M)G(M)G(M)GGC(F)C(F)U(F)C(F)C(F)AC
(F)A(M)G(M)C(M)G(M)U(F)AAG(M)C(M)U(M)U(M)G(M)GAC
(F)U(F)U(F)AA(M)A(M)C(M)C(M)A(M)C(M)G(M)

SEQ ID NO: 28(3):
(sequence obtained by introducing 2'-O-methyl modification into one position of the consensus sequence of the sequence shown in SEQ ID NO: 28)

C(M)G(M)U(M)AG(M)G(M)GGC(F)C(F)U(F)C(F)C(F)AC(F)
A(M)G(M)C(M)G(M)U(F)AAG(M)C(M)U(M)U(M)G(M)GAC(F)
U(M)U(F)AA(M)A(M)C(M)C(M)A(M)C(M)G(M)

SEQ ID NO: 28(4):
(sequence obtained by introducing 2'-O-methyl modification into one position of the consensus sequence of the sequence shown in SEQ ID NO: 28)

C(M)G(M)U(M)AG(M)G(M)GGC(F)C(F)U(F)C(F)C(F)AC(F)
A(M)G(M)C(M)G(M)U(F)AAG(M)C(M)U(M)U(M)G(M)GAC(F)
U(F)U(M)AA(M)A(M)C(M)C(M)A(M)C(M)G(M)

SEQ ID NO: 28(5):
(sequence obtained by introducing 2'-O-methyl modification into 4 positions of the consensus sequence of the sequence shown in SEQ ID NO: 28)

C(M)G(M)U(M)A(M)G(M)G(M)GGC(F)C(F)U(F)C(F)C(F)AC
(F)A(M)G(M)C(M)G(M)U(M)A(M)A(M)G(M)C(M)U(M)U(M)G
(M)GAC(F)U(F)U(F)AA(M)A(M)C(M)C(M)A(M)C(M)G(M)

SEQ ID NO: 28(6):
(sequence obtained by introducing 2'-fluoro modification into one position other than the consensus sequence of the sequence shown in SEQ ID NO: 28)

C(M)G(M)U(M)A(F)G(M)G(M)GGC(F)C(F)U(F)C(F)C(F)AC
(F)A(M)G(M)C(M)G(M)U(F)AAG(M)C(M)U(M)U(M)G(M)GAC
(F)U(F)U(F)AA(M)A(M)C(M)C(M)A(M)C(M)G(M)

SEQ ID NO: 28(7):
(sequence obtained by introducing 2'-fluoro modification into one position of the consensus sequence of the sequence shown in SEQ ID NO: 28)

C(M)G(M)U(M)AG(M)G(M)G(F)GC(F)C(F)U(F)C(F)C(F)AC
(F)A(M)G(M)C(M)G(M)U(F)AAG(M)C(M)U(M)U(M)G(M)GAC
(F)U(F)U(F)AA(M)A(M)C(M)C(M)A(M)C(M)G(M)

SEQ ID NO: 28(8):
(sequence obtained by introducing 2'-fluoro modification into one position of the consensus sequence of the sequence shown in SEQ ID NO: 28)

C(M)G(M)U(M)AG(M)G(M)GG(F)C(F)C(F)U(F)C(F)C(F)AC
(F)A(M)G(M)C(M)G(M)U(F)AAG(M)C(M)U(M)U(M)G(M)GAC
(F)U(F)U(F)AA(M)A(M)C(M)C(M)A(M)C(M)G(M)

SEQ ID NO: 28(9):
(sequence obtained by introducing 2'-fluoro modification into one position other than the consensus sequence of the sequence shown in SEQ ID NO: 28)

C(M)G(M)U(M)AG(M)G(M)GGC(F)C(F)U(F)C(F)C(F)A(F)C
(F)A(M)G(M)C(M)G(M)U(F)AAG(M)C(M)U(M)U(M)G(M)GAC
(F)U(F)U(F)AA(M)A(M)C(M)C(M)A(M)C(M)G(M)

SEQ ID NO: 28(10):
(sequence obtained by introducing 2'-fluoro modification into one position of the consensus sequence of the sequence shown in SEQ ID NO: 28)

C(M)G(M)U(M)AG(M)G(M)GGC(F)C(F)U(F)C(F)C(F)
AC(F)A(M)G(M)C(M)G(M)U(F)AAG(M)C(M)U(M)U(M)
G(M)G(F)AC(F)U(F)U(F)AA(M)A(M)C(M)C(M)A(M)
C(M)G(M)

SEQ ID NO: 28(11):
(sequence obtained by introducing 2'-fluoro modification into one position of the consensus sequence of the sequence shown in SEQ ID NO: 28)

C(M)G(M)U(M)AG(M)G(M)GGC(F)C(F)U(F)C(F)C(F)AC(F)
A(M)G(M)C(M)G(M)U(F)AAG(M)C(M)U(M)U(M)G(M)GA(F)
C(F)U(F)U(F)AA(M)A(M)C(M)C(M)A(M)C(M)G(M)

SEQ ID NO: 28(12):
(sequence obtained by introducing 2'-fluoro modification into one position of the consensus sequence of the sequence shown in SEQ ID NO: 28)

C(M)G(M)U(M)AG(M)G(M)GGC(F)C(F)U(F)C(F)C(F)AC(F)
A(M)G(M)C(M)G(M)U(F)AAG(M)C(M)U(M)U(M)G(M)GAC(F)
U(F)U(F)A(F)A(M)A(M)C(M)C(M)A(M)C(M)G(M)

SEQ ID NO: 28(13):
(sequence obtained by introducing 2'-O-methyl modification into 5 positions of the sequence shown in SEQ ID NO: 28 and adding idT to 3'-terminal)

C(M)G(M)U(M)A(M)G(M)G(M)GGC(F)C(F)U(F)C(F)C(F)
AC(F)A(M)G(M)C(M)G(M)U(M)A(M)A(M)G(M)C(M)U(M)
U(M)G(M)GAC(F)U(M)U(F)AA(M)A(M)C(M)C(M)A(M)C(M)
G(M)-idT

SEQ ID NO: 28(14):
(sequence obtained by introducing 2'-fluoro modification into one position of the sequence shown in SEQ ID NO: 28(13))

C(M)G(M)U(M)A(M)G(M)G(M)G(F)GC(F)C(F)U(F)C(F)C(F)
AC(F)A(M)G(M)C(M)G(M)U(M)A(M)A(M)G(M)C(M)U(M)U(M)
G(M)G(F)AO(F)U(M)U(F)AA(M)C(M)C(M)A(M)C(M)G
(M)-idT

SEQ ID NO: 28(15):
(sequence obtained by introducing 2'-O-methyl modification into 4 positions of the sequence shown in SEQ ID NO: 28 and adding idT to 3'-terminal)

C(M)G(M)U(M)AG(M)G(M)GGC(F)C(F)U(F)C(F)C(F)AC(F)
A(M)G(M)C(M)G(M)U(M)A(M)A(M)G(M)C(M)U(M)U(M)G(M)
GAC(F)U(M)U(F)AA(M)A(M)C(M)C(M)A(M)C(M)G(M)-idT

SEQ ID NO: 28(16):
(sequence obtained by introducing 2'-O-methyl modification into 4 positions of the sequence shown in SEQ ID NO: 28 and adding idT to 3'-terminal)

C(M)G(M)U(M)A(M)G(M)G(M)GGC(F)C(F)U(F)C(F)C(F)
AC(F)A(M)G(M)C(M)G(M)U(F)A(M)A(M)G(M)C(M)U(M)U
(M)G(M)GAC(F)U(M)U(F)AA(M)A(M)C(M)C(M)A(M)C(M)
G(M)-idT

SEQ ID NO: 28(17):
(sequence obtained by introducing 2'-O-methyl modification into 3 positions of the sequence shown in SEQ ID NO: 28 and adding idT to 3'-terminal)

C(M)G(M)U(M)AG(M)G(M)GGC(F)C(F)U(F)C(F)C(F)AC(F)
A(M)G(M)C(M)G(M)U(F)A(M)A(M)G(M)C(M)U(M)U(M)G(M)
GAC(F)U(M)U(F)AA(M)A(M)C(M)C(M)A(M)C(M)G(M)-idT

SEQ ID NO: 28(18):
(sequence obtained by adding PEG to 5'-terminal of the sequence shown in SEQ ID NO: 28(15))

PEG-
C(M)G(M)U(M)AG(M)G(M)GGC(F)C(F)U(F)C(F)C(F)AC(F)A
(M)G(M)C(M)G(M)U(M)A(M)A(M)G(M)C(M)U(M)U(M)G(M)GAC
(F)U(M)U(F)AA(M)A(M)C(M)C(M)A(M)C(M)G(M)-idT

SEQ ID NO: 29(1):
(sequence obtained by introducing 2'-O-methyl modification into one position of the consensus sequence of the sequence shown in SEQ ID NO: 29)

C(M)G(M)U(M)A(M)G(M)G(M)GGC(F)C(F)U(F)C(F)C(F)AC
(F)A(M)G(M)C(M)A(M)U(M)U(M)C(M)G(M)C(M)U(M)U(M)G
(M)GAC(F)A(M)C(F)AA(M)A(M)C(M)C(M)A(M)C(M)G(M)-idT

SEQ ID NO: 29(2):
(sequence obtained by introducing 2'-fluoro modification into one position of the consensus sequence of the sequence shown in SEQ ID NO: 29)

C(M)G(M)U(M)A(M)G(M)G(M)G(F)GC(F)C(F)U(F)C(F)C
(F)AC(F)A(M)G(M)C(M)A(M)U(M)U(M)C(M)G(M)C(M)U(M)
U(M)G(M)G(F)AC(F)A(M)C(F)AA(M)A(M)C(M)C(M)A(M)C
(M)G(M)-idT

SEQ ID NO: 29(3):
(sequence obtained by introducing 2'-fluoro modification into two positions of the consensus sequence of the sequence shown in SEQ ID NO: 29)

C(M)G(M)U(M)A(M)G(M)G(M)G(F)GC(F)C(F)U(F)C(F)C
(F)AC(F)A(M)G(M)C(M)A(M)U(M)U(M)C(M)G(M)C(M)U(M)
U(M)G(M)G(F)AC(F)AC(F)AA(M)A(M)C(M)C(M)A(M)C(M)G
(M)-idT

The aptamers having the sequences shown in SEQ ID NOs: 28(1)-28(18) (SEQ ID NO: 28 lineage) and SEQ ID NOs: 29(1)-29(3) (SEQ ID NO: 29 lineage) were all produced by chemical synthesis. Whether these aptamers inhibit the enzyme activity of ADAMTS5 was evaluated by a method similar to that in Example 1 and Example 5. The measurement results are shown in Table 9. In the Table, "n.d." means not determined. In the Table, the "evaluation method 1" is an enzyme inhibitory activity evaluation method using electrophoresis as the detection method, and shows the inhibitory activity at a final concentration of 10 nM nucleic acid. The "evaluation method 2" is an enzyme inhibitory activity evaluation method using ELISA method as the detection method, and shows the inhibitory activity and $IC_{50}$ value at a final concentration of 2 nM nucleic acid. "n.d." means not determined.

TABLE 9 inhibitory activity against ADAMTS5

| SEQ ID NO: | inhibitory activity (%) | | IC$_{50}$ (nM) |
| --- | --- | --- | --- |
| | evaluation method 1 | evaluation method 2 | evaluation method 2 |
| 28 | 81 | n.d. | n.d. |
| 28(1) | 76.6 | n.d. | n.d. |
| 28(2) | 68.7 | n.d. | n.d. |
| 28(3) | 77.5 | n.d. | 0.108 |
| 28(4) | 2.7 | n.d. | n.d. |
| 28(5) | 77.3 | n.d. | n.d. |
| 28(6) | 76.8 | n.d. | n.d. |
| 28(7) | 84.1 | n.d. | n.d. |
| 28(8) | 71.1 | n.d. | n.d. |
| 28(9) | 69.7 | n.d. | n.d. |
| 28(10) | 76.6 | n.d. | n.d. |
| 28(11) | 42.6 | n.d. | n.d. |
| 28(12) | 67.8 | n.d. | n.d. |
| 28(13) | 86.1 | n.d. | n.d. |
| 28(14) | 90.6 | n.d. | n.d. |
| 28(15) | n.d. | 98.1 | 0.084 |
| 28(16) | n.d. | 93.7 | n.d. |
| 28(17) | n.d. | 100 | n.d. |
| 28(18) | n.d. | 95.9 | 0.029 |
| 29 | 84 | n.d. | n.d. |
| 29(1) | 92.9 | n.d. | 0.17 |
| 29(2) | 89.8 | n.d. | n.d. |
| 29(3) | 80.9 | n.d. | n.d. |

From the results of the aptamers having the sequences shown in SEQ ID NOs: 28(2) and 28(6), it was found that A at the fourth base from the 5'-terminal (forming a bulge structure at stem 1) functions for RNA, as well as 2'-fluoro modification and 2'-O-methyl modification. From the results of the aptamers having the sequences shown in SEQ ID NOs: 28(3) and 29(1), it was found that the 7th W (A or U) from the 3'-terminal of the consensus sequence also functions for RNA, 2'-fluoro modification, and 2'-O-methyl modification. From the results of the aptamers having the sequences shown in SEQ ID NOs: 28(7), 28(8), 28(10), 28(12), 29(2)), it was found that G for the 3rd base and the 4th base from the 5'-terminal, and the 10th base G and the 5th base A from the 3'-terminal of the consensus sequence also function for RNA, as well as 2'-fluoro modification. On the other hand, from the results of the aptamers having the sequences shown in SEQ ID NOs: 28(4) and 28(11), it was found that introduction of the 2'-O-methylation modification into the 6th Y from the 3'-terminal of the consensus sequence markedly attenuates the inhibitory activity of the aptamers, and 2'-fluorination modification of the 9th A from the 3'-terminal lowers the activity of the aptamers.

From the results of the aptamers having the sequences shown in SEQ ID NOs: 28(13)-(18) (SEQ ID NO: 28 lineage), 29 and 29(1)-29(3) (SEQ ID NO: 29 lineage), it was found that the addition of PEG to the 5'-terminal and idT to the 3'-terminal does not affect the inhibitory activity. As the terminal modification, peptide, amino acid, sugar, glycosaminoglycan, biotin and the like can be mentioned besides PEG and idT.

Example 9: Production of RNA Aptamer that Specifically Binds to ADAMTS5-(3)

RNA aptamer that specifically binds to ADAMTS5 was prepared by an improved method of the SELEX method of Vater et al. (Vater et al. Nucleic Acid Research, 31, e130, 2003). As the target substance for SELEX, ADAMTS5 (manufactured by R&D systems) immobilized on a carrier of NHS-activated Sepharose 4 Fast Flow (manufactured by GE healthcare) was used. The RNA used in the first round was obtained by transcribing a chemically synthesized DNA by a method similar to that in Example 1. RNA obtained by this method is that wherein the 2'-position of the ribose of the pyrimidine nucleotide is fluorinated. The sequences of the templates and primers used are shown below. The DNA template and primers were produced by chemical synthesis. The template DNA has a design in which a mutation is introduced into the sequence of the stem-loop region other than the consensus sequence of the sequence of SEQ ID NO: 11.

```
DNA template:
                                 (SEQ ID NO: 52)
5'-ATATCTTTTGCTTATTCTCGAGAATTGGTTTAGTCCANNNNNNNN

NNNGTGGAGGCCCCAATACCCTATAGTGAGTCGTATTA-3' primer Fwd:
                                 (SEQ ID NO: 53)
5'-TAATACGACTCACTATAGGGT-3' primer Rev:
                                 (SEQ ID NO: 54)
5'-ATATCTTTTGCTTATTCTCGAG-3'
```

The continuous Ns in the DNA template (SEQ ID NO: 46) are any combination of 10 nucleotides (each N is A, C, G or T). The primer Fwd comprises a promoter sequence of T7 RNA polymerase. The variation of the RNA pool used in the first round was theoretically $10^{13}$.

RNA pool was added to the carrier on which ADAMTS5 was immobilized, and the mixture was maintained at room temperature for 30 min. The resin was washed with solution A to remove RNA not bound to ADAMTS5. Here, solution A is a mixed solution of 145 mM sodium chloride, 5.4 mM potassium chloride, 1.8 mM calcium chloride, 0.8 mM magnesium chloride, 20 mM tris (pH 7.6), and 0.05% Tween 20. The RNA bound to ADAMTS5 was obtained by adding solution B as an eluate, heat-treating the mixture at 95° C. for 3 min and collecting from the supernatant thereof. Here, solution B is a mixed solution of 7 M Urea, 5 mM EDTA, and 20 mM tris (pH 7.6). In the recovered RNA, a primer sequence was linked to the both terminals using T7 RNA Ligase 2 (manufactured by New England Biolabs) and the RNA was amplified by reverse transcription PCR. Restriction enzyme site XhoI was designed on the 3'-terminal of the Rev primer, and Rev primer sequence can be removed by digesting the PCR amplification product with XhoI (manufactured by New England Biolabs). Using the PCR amplification product digested with restriction enzyme as a template, it was transcribed using DuraScribe™ T7 Transcription Kit and used as a pool for the next round. With the above as 1 round, a similar operation was repeated plural times. After completion of SELEX, large-scale analysis of the nucleotide sequence was also performed using the next generation sequencer. As the next generation sequencer, Ion PGM™ system (manufactured by Thermo) was used and the analysis was performed according to the manual of Thermo.

After 3 rounds of SELEX, 7956 kinds of clone sequences were determined by the next generation sequencer, and they were confirmed to converge to 7676 kinds of sequence. Some sequences of such clones are shown in SEQ ID NOs: 30-45. Four sequences shown by SEQ ID NO: 30 were present. Three sequences shown by SEQ ID NOs: 31-45 were present.

The secondary structures of these sequences were predicted by the MFOLD program (M. Zuker, Nucleic Acids Res. 31(13), 3406-3415, 2003). As a result, the consensus sequence portion had a similar loop structure. The secondary structures of these sequences are presented in FIG. 7-1, FIG. 7-2, and FIG. 7-3. In FIG. 7-1, FIG. 7-2, and FIG. 7-3, the consensus sequences are enclosed with a circle (○). In addition, sequences different from SEQ ID NO: 11 are indicated by an arrow (black triangle).

Respective nucleotide sequences shown in SEQ ID NOs: 30-45 are presented below. Unless particularly indicated, the sequences shown below are in the 5' to 3' direction, purine bases (A and G) are 2'-OH compounds and pyrimidine bases (U and C) are 2'-fluoro modified compounds.

SEQ ID NO: 30:
GGGUAUUGGGGCCUCCACAAUAGAUAAAUGGACUAAACCAACUCGA

SEQ ID NO: 31:
GGGUAUUGGGGCCUCCACAGUUGAAGCUUGGACUAAACCAAUCUCGA

SEQ ID NO: 32:
GGGUAUUGGGGCCUCCACAGAAAAAUCUUGGACUAAACCAAUCUCGA

SEQ ID NO: 33:
GGGUAUUGGGGCCUCCACAGCCGAGGCUUGGACUAAACCAAUCUCGA

SEQ ID NO: 34:
GGGUAUUGGGGCCUCCACAGAAAAAACUUGGACUAAACCAACUCGA

SEQ ID NO: 35:
GGGUAUUGGGGCCUCCACAGUAAGCACUUGGACUAAACCAGCUCGA

SEQ ID NO: 36:
GGGUAUUGGGGCCUCCACAGUUUAAACUUGGACUAAACCAACUCGA

SEQ ID NO: 37:
GGGUAUUGGGGCCUCCACAGUAAAUUCUUGGACUAAACCAACUCGA

SEQ ID NO: 38:
GGGUAUUGGGGCCUCCACGCUAGAAGGCUGGACUAAACCAACUCGA

SEQ ID NO: 39:
GGGUAUUGGGGCCUCCACGUAACUAAACUGGACUAAACCAACUCGA

SEQ ID NO: 40:
GGGUAUUGGGGCCUCCACGCAAUGGUGCUGGACUAAACCAACUCGA

SEQ ID NO: 41:
GGGUAUUGGGGCCUCCACAUGGAUACAUUGGACUAAACCAACUCGA

SEQ ID NO: 42:
GGGUAUUGGGGCCUCCACAGAUAAUUCUUGGACUAAACCAACUCGA

SEQ ID NO: 43:
GGGUAUUGGGGCCUCCACAGAAAAUUCUUGGACUAAACCAACUCGA

SEQ ID NO: 44:
GGGUAUUGGGGCCUCCACAGAACUUUCUUGGACUAAACCAACUCGA

SEQ ID NO: 45:
GGGUAUUGGGGCCUCCACAGAAAAGUCUUGGACUAAACCAACUCGA

The binding activity of the nucleic acids shown in SEQ ID NOs: 30-45 to ADAMTS5 was measured. The binding activity was evaluated by the surface plasmon resonance method. The measurement results are shown in Table 10. In the Table, "++" indicates those with the proportion of ADAMTS5 binding amount (RU value) to the amount of aptamer immobilized on the SA chip (RU value) of not less than 40%, "+" indicates those with the proportion of not less than 10% and less than 40%, and "−" indicates those with the proportion of less than 10%.

TABLE 10

| binding activity to ADAMTS5 | |
|---|---|
| SEQ ID NO: | binding activity |
| 30 | ++ |
| 31 | ++ |
| 32 | ++ |
| 33 | ++ |
| 34 | ++ |
| 35 | ++ |
| 36 | ++ |
| 37 | ++ |
| 38 | ++ |
| 39 | ++ |
| 40 | ++ |
| 41 | ++ |
| 42 | ++ |
| 43 | ++ |
| 44 | ++ |
| 45 | ++ |

From the measurement results, it was found that all the tested sequences bind to ADAMTS5. From the results of SEQ ID NOs: 30-45, it was shown that the sequence from the 16th G to the 23rd C of SEQ ID NO: 11 into which a mutation was introduced by a SELEX method tends to form 2 or 3 continuous base pairs, but the nucleotide sequence is variable at random.

Example 10: Evaluation of Aggrecan Cleavage Inhibitory Activity of ADAMTS5 Aptamer in Synovial Cells The aggrecan cleavage inhibitory activity of the aptamers shown in SEQ ID NOs: 11(34), 28(13), 28(15), 28(18) in synovial cells was measured. The measurement was performed by the following method. Synovial cells (HFLS-OA cells) (manufactured by Cell Applications) derived from human knee osteoarthritis patients were seeded at $2 \times 10^4$ cells per well, and cultured for 16-24 hr. The culture method followed the manual of Cell Applications. After culturing, the medium was removed, the cells were washed with Basal Medium (manufactured by Cell Applications), and 500 ng of aggrecan G1-IGD-G2 (manufactured by R&D systems) diluted with Basal Medium as a substrate was added. The aptamer was added simultaneously with the substrate to the samples to be evaluated for inhibition by the aptamer. The cells were kept cultured and the culture supernatant was collected after 3 days. The added substrate is cleaved during culture by substrate-cleaving enzymes such as ADAMTS5 secreted from the HFLS-OA cells. The amount of the cleaved substrate fragment contained in the culture supernatant was quantified by the ELISA method described in Example 5. The substrate cleavage efficiency in this evaluation system was 1-8%. The nucleic acid shown in SEQ ID NO: 15 was used as a negative control. The measurement results are shown in Table 11.

TABLE 11

| | inhibition rate (%) | | |
|---|---|---|---|
| SEQ ID NO: | 3 nM | 30 nM | 300 nM |
| 15 negative control | 10 | 8 | 37 |
| 11(34) | −8 | 15 | 58 |
| 28(13) | 42 | 52 | 79 |
| 28(15) | 40 | 63 | 80 |
| 28(18) | 45 | 63 | 78 |

As a result of the measurement, all aptamers showed a remarkable inhibitory activity as compared to the negative control. From the above results, the aptamer of the present invention can be said to show a superior inhibitory effect against substrate cleavage in synovial cells.

INDUSTRIAL APPLICABILITY

The aptamer or complex of the present invention can be useful as a medicament, or a diagnostic agent or a reagent for cartilage diseases such as knee osteoarthritis and the like. The aptamer or complex of the present invention can also be useful for purification and concentration of ADAMTS5, labeling of ADAMTS5, and detection and quantification of ADAMTS5.

This application is based on a patent application No. 2017-216280 filed in Japan (filing date: Nov. 9, 2017), the contents of which are incorporated in full herein.

The invention claimed is:

1. An aptamer comprising a sequence shown by the following formula (1) (SEQ ID NO:55) or formula (2) (SEQ ID NO:56):

(1)
GGGGCCUCC-N$_1$-GGACYAAACC (2)
GGGGCCUCC-N$_1$-GGACWYAAACC wherein N$_1$ shows 3 to 24 bases in length, Y is C or U, and W is A or U (uracil is optionally thymine), wherein the aptamer binds to a disintegrin and metalloproteinase with thrombospondin motifs-5 (ADAMTS5).

2. The aptamer according to claim 1, wherein the aptamer has a potential secondary structure shown by the following formula (1)' (SEQ ID NO:55) or formula (2)' (SEQ ID NO:56):

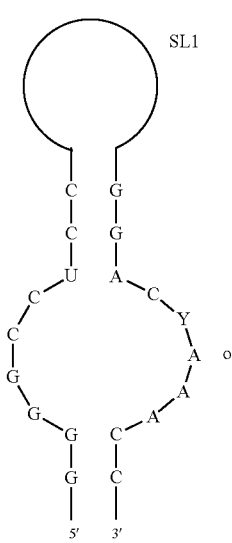

(1)' or

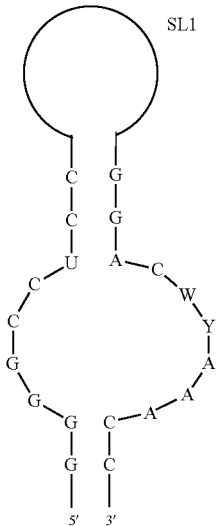

(2)' wherein the part of

in the formula (1)' and the formula (2)' shows a stem-loop structure optionally having a bulge structure and is the N$_1$ part, Y is C or U, and W is A or U.

3. The aptamer according to claim 1, wherein the aptamer inhibits the activity of ADAMTS5.

4. The aptamer according to claim 1, wherein the aptamer has a base length of not more than 80.

5. The aptamer according to claim 1, wherein W is U.

6. The aptamer according to claim 1, wherein Y is U.

7. The aptamer according to claim 1, wherein N$_1$ is the formula (3)

X$_1$CAGCN$_2$GCUX$_2$                                    (3)

wherein N$_2$ shows nucleotides in any number of 3 to 15, and X$_1$ and X$_2$ show a combination of A/U bases or G/C bases.

8. The aptamer according to claim 7, wherein the number of nucleotides for N$_2$ is 4.

9. The aptamer according to claim 1, comprising any of the nucleotide sequences of the following (a), (b) and (c):
(a) a nucleotide sequence selected from any of SEQ ID NOs: 1, 3-6, 10-14, 16-45 (uracil is optionally thymine);

(b) a nucleotide sequence selected from any of SEQ ID NOs: 1, 3-6, 10-14, 16-45 (uracil is optionally thymine) wherein one to several nucleotides are substituted, deleted, inserted or added; and (c) a nucleotide sequence having identity of not less than 70% with a nucleotide sequence selected from any of SEQ ID NOs: 1, 3-6, 10-14, 16-45 (uracil is optionally thymine).

10. The aptamer according to claim 9, wherein at least one nucleotide contained in the aptamer is modified or altered.

11. The aptamer according to claim 1, wherein a hydroxyl group at the ribose 2'-position of each pyrimidine nucleotide contained in the aptamer is the same or different and unsubstituted or substituted by an atom or a group selected from the group consisting of a hydrogen atom, a fluorine atom and a methoxy group.

12. The aptamer according to claim 1, wherein the hydroxyl group at the ribose 2'-position of each purine nucleotide contained in the aptamer is the same or different and unsubstituted or substituted by an atom or a group selected from the group consisting of a hydrogen atom, a fluorine atom and a methoxy group.

13. A complex comprising the aptamer according to claim 1 and the functional substance.

14. A medicament comprising the aptamer according to claim 1.

15. The medicament according to claim 14, wherein the medicament is a therapeutic drug for a disease caused by excessive decomposition of Aggrecan.

16. The medicament according to claim 15, wherein the disease caused by excessive decomposition of Aggrecan is arthritis or knee osteoarthritis.

17. A method for detecting ADAMTS5, comprising using the aptamer according to claim 1 in vitro.

18. A medicament comprising the complex according to claim 13.

19. The medicament according to claim 18, wherein the medicament is a therapeutic drug for a disease caused by excessive decomposition of Aggrecan.

20. The medicament according to claim 19, wherein the disease caused by excessive decomposition of Aggrecan is arthritis or knee osteoarthritis.

21. A method for detecting ADAMTS5, comprising using the complex according to claim 13 in vitro.

* * * * *

SEQUENCE LISTING

```
<160> NUMBER OF SEQ ID NOS: 59

<210> SEQ ID NO 1
<211> LENGTH: 80
<212> TYPE: RNA
<213> ORGANISM: Artificial Sequence
<220> FEATURE:
<223> OTHER INFORMATION: Synthetic Sequence - aptamer against ADAMTS5

<400> SEQUENCE: 1
ggguacgacc gucguacgau uggggccucc acagcugcuc agcuuggacu aaaccaauaa      60
gagacuaacg ccuagcguac                                                 80

<210> SEQ ID NO 2
<211> LENGTH: 79
<212> TYPE: RNA
<213> ORGANISM: Artificial Sequence
<220> FEATURE:
<223> OTHER INFORMATION: Synthetic Sequence - nucleotide sequence not
      binding to ADAMTS5

<400> SEQUENCE: 2
ggguacgacc gucguacgau ugggccucca cagcugcuca gcuuggacua aaccaauaag      60
agacuaacgc cuagcguac                                                  79

<210> SEQ ID NO 3
<211> LENGTH: 44
<212> TYPE: RNA
<213> ORGANISM: Artificial Sequence
<220> FEATURE:
<223> OTHER INFORMATION: Synthetic Sequence - aptamer against ADAMTS5

<400> SEQUENCE: 3
ggauuggggc cuccacagcu gcucagcuug gacuaaacca aucc                      44

<210> SEQ ID NO 4
<211> LENGTH: 44
<212> TYPE: RNA
<213> ORGANISM: Artificial Sequence
<220> FEATURE:
<223> OTHER INFORMATION: Synthetic Sequence - aptamer against ADAMTS5

<400> SEQUENCE: 4
ggcuuggggc cuccacagcu gcucagcuug gacuaaacca agcc                      44

<210> SEQ ID NO 5
<211> LENGTH: 42
<212> TYPE: RNA
<213> ORGANISM: Artificial Sequence
<220> FEATURE:
<223> OTHER INFORMATION: Synthetic Sequence - aptamer against ADAMTS5

<400> SEQUENCE: 5
ggcuuggggc cuccacagcg cucgcuugga cuaaaccaag cc                        42
```

<210> SEQ ID NO 6
<211> LENGTH: 43
<212> TYPE: RNA
<213> ORGANISM: Artificial Sequence
<220> FEATURE:
<223> OTHER INFORMATION: Synthetic Sequence - aptamer against ADAMTS5

<400> SEQUENCE: 6
ggcuuggggc uccacagcu gucagcuugg acuaaaccaa gcc                43

<210> SEQ ID NO 7
<211> LENGTH: 43
<212> TYPE: RNA
<213> ORGANISM: Artificial Sequence
<220> FEATURE:
<223> OTHER INFORMATION: Synthetic Sequence - nucleotide sequence not
      binding to ADAMTS5

<400> SEQUENCE: 7
ggcuuggggc uccacagcu gcucagcuug gacuaaccaa gcc                43

<210> SEQ ID NO 8
<211> LENGTH: 42
<212> TYPE: RNA
<213> ORGANISM: Artificial Sequence
<220> FEATURE:
<223> OTHER INFORMATION: Synthetic Sequence - nucleotide sequence not
      binding to ADAMTS5

<400> SEQUENCE: 8
ggcuuggggc cucacagcug cucagcuuga cuaaaccaag cc                42

<210> SEQ ID NO 9
<211> LENGTH: 41
<212> TYPE: RNA
<213> ORGANISM: Artificial Sequence
<220> FEATURE:
<223> OTHER INFORMATION: Synthetic Sequence - nucleotide sequence not
      binding to ADAMTS5

<400> SEQUENCE: 9
ggauuggggc cuccacagcg ucgcuuggac uaaaccaauc c                 41

<210> SEQ ID NO 10
<211> LENGTH: 40
<212> TYPE: RNA
<213> ORGANISM: Artificial Sequence
<220> FEATURE:
<223> OTHER INFORMATION: Synthetic Sequence - aptamer against ADAMTS5

<400> SEQUENCE: 10
auuggggccu ccacagcugc ucagcuugga cuaaaccaau                   40

<210> SEQ ID NO 11
<211> LENGTH: 38
<212> TYPE: RNA
<213> ORGANISM: Artificial Sequence
<220> FEATURE:
<223> OTHER INFORMATION: Synthetic Sequence - aptamer against ADAMTS5

<400> SEQUENCE: 11
auuggggccu ccacagcgcu cgcuuggacu aaaccaau                     38

<210> SEQ ID NO 12
<211> LENGTH: 36
<212> TYPE: RNA

```
<213> ORGANISM: Artificial Sequence
<220> FEATURE:
<223> OTHER INFORMATION: Synthetic Sequence - aptamer against ADAMTS5

<400> SEQUENCE: 12 uugggccuc cacagcgcuc gcuuggacua aaccaa                                    36

<210> SEQ ID NO 13
<211> LENGTH: 38
<212> TYPE: RNA
<213> ORGANISM: Artificial Sequence
<220> FEATURE:
<223> OTHER INFORMATION: Synthetic Sequence - aptamer against ADAMTS5

<400> SEQUENCE: 13
gcuggggccu ccacagcgcu cgcuuggacu aaaccagc                                 38

<210> SEQ ID NO 14
<211> LENGTH: 38
<212> TYPE: RNA
<213> ORGANISM: Artificial Sequence
<220> FEATURE:
<223> OTHER INFORMATION: Synthetic Sequence - aptamer against ADAMTS5

<400> SEQUENCE: 14
auuggggccu ccacagcuuc ggcuuggacu aaaccaau                                 38

<210> SEQ ID NO 15
<211> LENGTH: 38
<212> TYPE: RNA
<213> ORGANISM: Artificial Sequence
<220> FEATURE:
<223> OTHER INFORMATION: Synthetic Sequence - aptamer against ADAMTS5

<400> SEQUENCE: 15
auuggcacgg agacagcgcu cgcuucucga ucaccaau                                 38

<210> SEQ ID NO 16
<211> LENGTH: 74
<212> TYPE: RNA
<213> ORGANISM: Artificial Sequence
<220> FEATURE:
<223> OTHER INFORMATION: Synthetic Sequence - aptamer against ADAMTS5

<400> SEQUENCE: 16
gggacaugcg uaacuugaua ggggccuccg cagcugauca gcucggacuc aaaccaucaa         60
guccagaucg agca                                                           74

<210> SEQ ID NO 17
<211> LENGTH: 74
<212> TYPE: RNA
<213> ORGANISM: Artificial Sequence
<220> FEATURE:
<223> OTHER INFORMATION: Synthetic Sequence - aptamer against ADAMTS5

<400> SEQUENCE: 17
gggacaugcg uaacuguaua ggggccucca cagcugaaaa gcuggacuc aaaccauaca          60 guccagaucg agca                                                           74

<210> SEQ ID NO 18
<211> LENGTH: 74
<212> TYPE: RNA
<213> ORGANISM: Artificial Sequence
<220> FEATURE:
<223> OTHER INFORMATION: Synthetic Sequence - aptamer against ADAMTS5
```

```
<400> SEQUENCE: 18
gggacaugcg uaacugcauc ggggccuccg cagcuguuaa gcucggacuc aaaccaugca      60
guccagaucg agca                                                       74

<210> SEQ ID NO 19
<211> LENGTH: 74
<212> TYPE: RNA
<213> ORGANISM: Artificial Sequence
<220> FEATURE:
<223> OTHER INFORMATION: Synthetic Sequence - aptamer against ADAMTS5

<400> SEQUENCE: 19
gggacaugcg uaacuugaua ggggccucca cagcugauaa gcuuggacuc aaaccaucaa      60
guccagaucg agca                                                       74

<210> SEQ ID NO 20
<211> LENGTH: 74
<212> TYPE: RNA
<213> ORGANISM: Artificial Sequence
<220> FEATURE:
<223> OTHER INFORMATION: Synthetic Sequence - aptamer against ADAMTS5

<400> SEQUENCE: 20
gggacaugcg uaacuguaua ggggccuccg cagcuauuca gcucggacau aaaccauaca      60
guccagaucg agca                                                       74

<210> SEQ ID NO 21
<211> LENGTH: 76
<212> TYPE: RNA
<213> ORGANISM: Artificial Sequence
<220> FEATURE:
<223> OTHER INFORMATION: Synthetic Sequence - aptamer against ADAMTS5

<400> SEQUENCE: 21
gggacaugcg uaacuauaua ggggccucca cagcuguaaa gcuuggacuu aaaccauaua      60
gaguccagau cgagca                                                     76

<210> SEQ ID NO 22
<211> LENGTH: 74
<212> TYPE: RNA
<213> ORGANISM: Artificial Sequence
<220> FEATURE:
<223> OTHER INFORMATION: Synthetic Sequence - aptamer against ADAMTS5

<400> SEQUENCE: 22
gggacaugcg uaacugcaua ggggccucca cagcuauuca gcuuggacac aaaccaugca      60
guccagaucg agca                                                       74

<210> SEQ ID NO 23
<211> LENGTH: 74
<212> TYPE: RNA
<213> ORGANISM: Artificial Sequence
<220> FEATURE:
<223> OTHER INFORMATION: Synthetic Sequence - aptamer against ADAMTS5

<400> SEQUENCE: 23
gggacaugcg uaacuguaua ggggccucca cagcugaaaa gcuuggacuc aaaccauaca      60
guccagaucg agca                                                       74

<210> SEQ ID NO 24
```

```
<211> LENGTH: 74
<212> TYPE: RNA
<213> ORGANISM: Artificial Sequence
<220> FEATURE:
<223> OTHER INFORMATION: Synthetic Sequence - aptamer against ADAMTS5

<400> SEQUENCE: 24
gggacaugcg uaacuugaua ggggccucca cagccgguag gcuuggacuc aaaccaucaa    60
guccagaucg agca                                                     74

<210> SEQ ID NO 25
<211> LENGTH: 74
<212> TYPE: RNA
<213> ORGANISM: Artificial Sequence
<220> FEATURE:
<223> OTHER INFORMATION: Synthetic Sequence - aptamer against ADAMTS5

<400> SEQUENCE: 25
gggacaugcg uaacugcaua ggggccucca cagcuauuca gcuuggacac aaaccaugca    60
guccagaucg agca                                                     74

<210> SEQ ID NO 26
<211> LENGTH: 46
<212> TYPE: RNA
<213> ORGANISM: Artificial Sequence
<220> FEATURE:
<223> OTHER INFORMATION: Synthetic Sequence - aptamer against ADAMTS5

<400> SEQUENCE: 26
ggguauaggg gccuccacag cguaagcuug gacuuaaacc auaccc                  46

<210> SEQ ID NO 27
<211> LENGTH: 40
<212> TYPE: RNA
<213> ORGANISM: Artificial Sequence
<220> FEATURE:
<223> OTHER INFORMATION: Synthetic Sequence - aptamer against ADAMTS5

<400> SEQUENCE: 27
uauaggggcc uccacagcgu aagcuuggac uuaaaccaua                         40

<210> SEQ ID NO 28
<211> LENGTH: 40
<212> TYPE: RNA
<213> ORGANISM: Artificial Sequence
<220> FEATURE:
<223> OTHER INFORMATION: Synthetic Sequence - aptamer against ADAMTS5

<400> SEQUENCE: 28
cguaggggcc uccacagcgu aagcuuggac uuaaaccacg                         40

<210> SEQ ID NO 29
<211> LENGTH: 40
<212> TYPE: RNA
<213> ORGANISM: Artificial Sequence
<220> FEATURE:
<223> OTHER INFORMATION: Synthetic Sequence - aptamer against ADAMTS5

<400> SEQUENCE: 29
cguaggggcc uccacagcau ucgcuuggac acaaaccacg                         40

<210> SEQ ID NO 30
<211> LENGTH: 46
<212> TYPE: RNA
<213> ORGANISM: Artificial Sequence
```

<220> FEATURE:
<223> OTHER INFORMATION: Synthetic Sequence - aptamer against ADAMTS5

<400> SEQUENCE: 30
ggguauuggg gccuccacaa uagauaaaug gacuaaacca acucga            46

<210> SEQ ID NO 31
<211> LENGTH: 47
<212> TYPE: RNA
<213> ORGANISM: Artificial Sequence
<220> FEATURE:
<223> OTHER INFORMATION: Synthetic Sequence - aptamer against ADAMTS5

<400> SEQUENCE: 31
ggguauuggg gccuccacag uugaagcuug gacuaaacca aucucga           47

<210> SEQ ID NO 32
<211> LENGTH: 47
<212> TYPE: RNA
<213> ORGANISM: Artificial Sequence
<220> FEATURE:
<223> OTHER INFORMATION: Synthetic Sequence - aptamer against ADAMTS5

<400> SEQUENCE: 32
ggguauuggg gccuccacag aaaaaucuug gacuaaacca aucucga           47

<210> SEQ ID NO 33
<211> LENGTH: 47
<212> TYPE: RNA
<213> ORGANISM: Artificial Sequence
<220> FEATURE:
<223> OTHER INFORMATION: Synthetic Sequence - aptamer against ADAMTS5

<400> SEQUENCE: 33
ggguauuggg gccuccacag ccgaggcuug gacuaaacca aucucga           47

<210> SEQ ID NO 34
<211> LENGTH: 46
<212> TYPE: RNA
<213> ORGANISM: Artificial Sequence
<220> FEATURE:
<223> OTHER INFORMATION: Synthetic Sequence - aptamer against ADAMTS5

<400> SEQUENCE: 34
ggguauuggg gccuccacag aaaaaacuug gacuaaacca acucga            46

<210> SEQ ID NO 35
<211> LENGTH: 46
<212> TYPE: RNA
<213> ORGANISM: Artificial Sequence
<220> FEATURE:
<223> OTHER INFORMATION: Synthetic Sequence - aptamer against ADAMTS5

<400> SEQUENCE: 35
ggguauuggg gccuccacag uaagcacuug gacuaaacca gcucga            46

<210> SEQ ID NO 36
<211> LENGTH: 46
<212> TYPE: RNA
<213> ORGANISM: Artificial Sequence
<220> FEATURE:
<223> OTHER INFORMATION: Synthetic Sequence - aptamer against ADAMTS5

<400> SEQUENCE: 36
ggguauuggg gccuccacag uuuaaacuug gacuaaacca acucga            46

```
<210> SEQ ID NO 37
<211> LENGTH: 46
<212> TYPE: RNA
<213> ORGANISM: Artificial Sequence
<220> FEATURE:
<223> OTHER INFORMATION: Synthetic Sequence - aptamer against ADAMTS5

<400> SEQUENCE: 37
ggguauuggg gccuccacag uaaauucuug gacuaaacca acucga                    46

<210> SEQ ID NO 38
<211> LENGTH: 46
<212> TYPE: RNA
<213> ORGANISM: Artificial Sequence
<220> FEATURE:
<223> OTHER INFORMATION: Synthetic Sequence - aptamer against ADAMTS5

<400> SEQUENCE: 38
ggguauuggg gccuccacgc uagaaggcug gacuaaacca acucga                    46

<210> SEQ ID NO 39
<211> LENGTH: 46
<212> TYPE: RNA
<213> ORGANISM: Artificial Sequence
<220> FEATURE:
<223> OTHER INFORMATION: Synthetic Sequence - aptamer against ADAMTS5

<400> SEQUENCE: 39
ggguauuggg gccuccacgu aacuaaacug gacuaaacca acucga                    46

<210> SEQ ID NO 40
<211> LENGTH: 46
<212> TYPE: RNA
<213> ORGANISM: Artificial Sequence
<220> FEATURE:
<223> OTHER INFORMATION: Synthetic Sequence - aptamer against ADAMTS5

<400> SEQUENCE: 40
ggguauuggg gccuccacgc aauggugcug gacuaaacca acucga                    46

<210> SEQ ID NO 41
<211> LENGTH: 46
<212> TYPE: RNA
<213> ORGANISM: Artificial Sequence
<220> FEATURE:
<223> OTHER INFORMATION: Synthetic Sequence - aptamer against ADAMTS5

<400> SEQUENCE: 41
ggguauuggg gccuccacau ggauacauug gacuaaacca acucga                    46

<210> SEQ ID NO 42
<211> LENGTH: 46
<212> TYPE: RNA
<213> ORGANISM: Artificial Sequence
<220> FEATURE:
<223> OTHER INFORMATION: Synthetic Sequence - aptamer against ADAMTS5

<400> SEQUENCE: 42
ggguauuggg gccuccacag auaauucuug gacuaaacca acucga                    46

<210> SEQ ID NO 43
<211> LENGTH: 46
<212> TYPE: RNA
<213> ORGANISM: Artificial Sequence
<220> FEATURE:
<223> OTHER INFORMATION: Synthetic Sequence - aptamer against ADAMTS5
```

<400> SEQUENCE: 43
ggguauuggg gccuccacag aaaauucuug gacuaaacca acucga          46

<210> SEQ ID NO 44
<211> LENGTH: 46
<212> TYPE: RNA
<213> ORGANISM: Artificial Sequence
<220> FEATURE:
<223> OTHER INFORMATION: Synthetic Sequence - aptamer against ADAMTS5

<400> SEQUENCE: 44
ggguauuggg gccuccacag aacuuucuug gacuaaacca acucga          46

<210> SEQ ID NO 45
<211> LENGTH: 46
<212> TYPE: RNA
<213> ORGANISM: Artificial Sequence
<220> FEATURE:
<223> OTHER INFORMATION: Synthetic Sequence - aptamer against ADAMTS5

<400> SEQUENCE: 45
ggguauuggg gccuccacag aaaagucuug gacuaaacca acucga          46

<210> SEQ ID NO 46
<211> LENGTH: 80
<212> TYPE: DNA
<213> ORGANISM: Artificial Sequence
<220> FEATURE:
<223> OTHER INFORMATION: Synthetic Sequence - DNA template
<220> FEATURE:
<221> NAME/KEY: misc_feature
<222> LOCATION: (21)..(60)
<223> OTHER INFORMATION: n is a, c, g, or t

<400> SEQUENCE: 46
gtacgctagg cgttagtctc nnnnnnnnnn nnnnnnnnnn nnnnnnnnnn nnnnnnnnnn          60
atcgtacgac ggtcgtaccc          80

<210> SEQ ID NO 47
<211> LENGTH: 37
<212> TYPE: DNA
<213> ORGANISM: Artificial Sequence
<220> FEATURE:
<223> OTHER INFORMATION: Synthetic Sequence - primer Fwd

<400> SEQUENCE: 47
taatacgact cactataggg tacgaccgtc gtacgat          37

<210> SEQ ID NO 48
<211> LENGTH: 20
<212> TYPE: DNA
<213> ORGANISM: Artificial Sequence
<220> FEATURE:
<223> OTHER INFORMATION: Synthetic Sequence - primer Rev

<400> SEQUENCE: 48
gtacgctagg cgttagtctc          20

<210> SEQ ID NO 49
<211> LENGTH: 74
<212> TYPE: DNA
<213> ORGANISM: Artificial Sequence
<220> FEATURE:
<223> OTHER INFORMATION: Synthetic Sequence - DNA template

<400> SEQUENCE: 49
tgctcgatct ggactggatt ggtttagtcc aagctgagca gctgtggagg ccccaatcca    60
gttacgcatg tccc    74

<210> SEQ ID NO 50
<211> LENGTH: 32
<212> TYPE: DNA
<213> ORGANISM: Artificial Sequence
<220> FEATURE:
<223> OTHER INFORMATION: Synthetic Sequence - primer Fwd

<400> SEQUENCE: 50
taatacgact cactataggg acatgcgtaa ct    32

<210> SEQ ID NO 51
<211> LENGTH: 15
<212> TYPE: DNA
<213> ORGANISM: Artificial Sequence
<220> FEATURE:
<223> OTHER INFORMATION: Synthetic Sequence - primer Rev

<400> SEQUENCE: 51
tgctcgatct ggact    15

<210> SEQ ID NO 52
<211> LENGTH: 82
<212> TYPE: DNA
<213> ORGANISM: Artificial Sequence
<220> FEATURE:
<223> OTHER INFORMATION: Synthetic Sequence - DNA template
<220> FEATURE:
<221> NAME/KEY: misc_feature
<222> LOCATION: (38)..(47)
<223> OTHER INFORMATION: n is  a, c, g, or t

<400> SEQUENCE: 52
atatcttttg cttattctcg agaattggtt tagtccannn nnnnnnngtg gaggccccaa    60
taccctatag tgagtcgtat ta    82

<210> SEQ ID NO 53
<211> LENGTH: 21
<212> TYPE: DNA
<213> ORGANISM: Artificial Sequence
<220> FEATURE:
<223> OTHER INFORMATION: Synthetic Sequence - primer Fwd

<400> SEQUENCE: 53
taatacgact cactataggg t    21

<210> SEQ ID NO 54
<211> LENGTH: 22
<212> TYPE: DNA
<213> ORGANISM: Artificial Sequence
<220> FEATURE:
<223> OTHER INFORMATION: Synthetic Sequence - primer Rev

<400> SEQUENCE: 54
atatcttttg cttattctcg ag    22

<210> SEQ ID NO 55
<211> LENGTH: 43
<212> TYPE: RNA
<213> ORGANISM: Artificial Sequence
<220> FEATURE:
<223> OTHER INFORMATION: Synthetic Sequence

```
<220> FEATURE:
<221> NAME/KEY: misc_feature
<222> LOCATION: (10)..(13)
<223> OTHER INFORMATION: n can be any nucleotide
<220> FEATURE:
<221> NAME/KEY: misc_feature
<222> LOCATION: (14)..(33)
<223> OTHER INFORMATION: n can be any or no nucleotide

<400> SEQUENCE: 55
ggggccuccn nnnnnnnnnn nnnnnnnnnn nnnggacyaa acc          43

<210> SEQ ID NO 56
<211> LENGTH: 44
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (10)..(13)
<223> OTHER INFORMATION: n can be any nucleotide
<220> FEATURE:
<221> NAME/KEY: misc_feature
<222> LOCATION: (14)..(33)
<223> OTHER INFORMATION: n can be any or no nucleotide

<400> SEQUENCE: 56
ggggccuccn nnnnnnnnnn nnnnnnnnnn nnnggacwya aacc         44

<210> SEQ ID NO 57
<211> LENGTH: 24
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (1)..(1)
<223> OTHER INFORMATION: n is any combination of A/U bases or G/C bases
<220> FEATURE:
<221> NAME/KEY: misc_feature
<222> LOCATION: (6)..(8)
<223> OTHER INFORMATION: n can be any nucleotide
<220> FEATURE:
<221> NAME/KEY: misc_feature
<222> LOCATION: (9)..(20)
<223> OTHER INFORMATION: n can be any or no nucleotide
<220> FEATURE:
<221> NAME/KEY: misc_feature
<222> LOCATION: (24)..(24)
<223> OTHER INFORMATION: n is any combination of A/U bases or G/C bases

<400> SEQUENCE: 57 ncagcnnnn nnnnnnnnnnn gcun                               24

<210> SEQ ID NO 58
<211> LENGTH: 11
<212> TYPE: DNA
<213> ORGANISM: Artificial Sequence
<220> FEATURE:
<223> OTHER INFORMATION: Synthetic Sequence

<400> SEQUENCE: 58
ggacwyaaac c                                             11
```

```
<210> SEQ ID NO 59
<211> LENGTH: 11
<212> TYPE: DNA
<213> ORGANISM: Artificial Sequence
<220> FEATURE:
<223> OTHER INFORMATION: Synthetic Sequence

<400> SEQUENCE: 59
ggacwyaaac c                                                    11
```